United States Patent
Oberboersch et al.

(10) Patent No.: US 7,348,347 B2
(45) Date of Patent: Mar. 25, 2008

(54) SUBSTITUTED 4,5,6,7-TETRAHYDROBENZTHIAZOL-2-YLAMINE COMPOUNDS

(75) Inventors: Stefan Oberboersch, Aachen (DE); Corinna Sundermann, Aachen (DE); Bernd Sundermann, Aachen (DE); Edward Bijsterveld, Nijmegen (NL)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 11/502,456

(22) Filed: Aug. 11, 2006

(65) Prior Publication Data
US 2007/0027315 A1 Feb. 1, 2007

Related U.S. Application Data

(63) Continuation of application No. PCT/EP2005/001369, filed on Feb. 11, 2005.

(30) Foreign Application Priority Data
Feb. 11, 2004 (DE) .................. 10 2004 006 808

(51) Int. Cl.
- A61K 31/428 (2006.01)
- A61K 31/497 (2006.01)
- A61K 31/4025 (2006.01)
- A61K 31/5513 (2006.01)
- C07D 277/60 (2006.01)
- C07D 243/06 (2006.01)
- C07D 207/04 (2006.01)

(52) U.S. Cl. ............ 514/367; 514/254.04; 514/252.13; 514/218; 514/422; 544/367; 544/135; 544/368; 540/553; 548/163; 548/180; 548/161; 548/518

(58) Field of Classification Search ................ 548/161, 548/180, 163, 518; 549/505; 514/367, 254.04, 514/252.13, 218, 422; 544/135, 368; 540/553
See application file for complete search history.

(56) References Cited

U.S. PATENT DOCUMENTS

| 5,286,735 A | 2/1994 | Bonnaud et al. |
| 6,825,355 B2 * | 11/2004 | Das et al. .................. 548/161 |

FOREIGN PATENT DOCUMENTS

| EP | 0 186 087 A1 | 7/1986 |
| EP | 0 445 026 A1 | 9/1991 |
| WO | WO 94/13287 A1 | 6/1994 |
| WO | WO 01/43740 A1 | 6/2001 |

OTHER PUBLICATIONS

A. N. Nitu et al, "Emerging Trends in the Pharmacotherapy of Chronic Pain", Expert OPIN. Investig. Drugs, Bd. 12, Nr. 4, 2003, pp. 545-559.

Gray, E.G., et al., "The Isolation of Nerve Endings from Brain: An Electron-Microscopic Study of Cell Fragments Derived by Homogenization and Centrifugation", Journal Anatomy, 1962, pp. 79-88, vol. 96, Cambridge.

Frink, M.C., et al., "Influence of Tramadol on Neurotransmitter Systems of the Rat Brain", Arzneim.-Forsch./Drug Res., 1996, pp. 1029-1036, vol. 46 (II), 11, Germany.

Lowry, O.H., "Protein Measurement with the Folin Phenol Reagent", The Journal of Bioogical Chemistry, 1951, pp. 265-275, Missouri.

International Preliminary Report on Patentability dated Oct. 4, 2006, including English translation and PCT/ISA/237 (Written Opinion of the International Searching Authority) (four (4) pages).

* cited by examiner

*Primary Examiner*—Kamal A Saeed
*Assistant Examiner*—Yong Chu
(74) *Attorney, Agent, or Firm*—Crowell & Moring LLP

(57) ABSTRACT

Substituted 4,5,6,7-tetrahydrobenzothiazol-2-ylamine compounds, a method for their production; pharmaceutical compositions comprising them, and methods of use for modulating biological functions and/or treating or inhibiting various medical conditions such as, e.g., depression and pain.

39 Claims, No Drawings

SUBSTITUTED 4,5,6,7-TETRAHYDROBENZTHIAZOL-2-YLAMINE COMPOUNDS

CROSS REFERENCE TO RELATED APPLICATIONS

This application is a continuation of International patent application No. PCT/EP2005/001369, filed Feb. 11, 2005, designating the United States of America and published in German as WO 2005/077924 A1, the entire disclosure of which is incorporated herein by reference. Priority is claimed based on Federal Republic of Germany patent application No. DE 10 2004 006 808.9, filed Feb. 11, 2004.

FIELD OF THE INVENTION

The present invention relates to substituted 4,5,6,7-tetrahydrobenzthiazol-2-ylamine compounds, to a process for the preparation thereof, to pharmaceutical compositions containing said compounds and to the use of said compounds for modulating biological functions and/or treating or inhibiting various medical conditions.

BACKGROUND OF THE INVENTION

Depression is an affectivity disorder in which a depressive syndrome is conspicuous, "depressive" being understood to refer to a state of dejection or melancholia. The antidepressants used for therapy are also important adjuvants for pain therapy (Tzschentke, N A and 5-HT Reuptake inhibitor and α2 agonist, in Analgesics: From Chemistry and Pharmacology to Clinical Application, Pages 265 to 284, Wiley 2002), particularly with chronic states of pain, since the constant pain can lead to a depressive mood in the patients. This is very frequently the case with cancer patients suffering pain (Berard, INT. MED—J. 1996, 3/4, 257-259). Since no analgesics are as yet known which contain a clinically relevant active antidepressant component, the antidepressants must be added as supplementary medication over and above the administration of analgesic. Since patients chronically in pain frequently require a large number of various pharmaceutical preparations, an additional dose of antidepressant will lead to a further strain on the organism. For this reason and also to improve the compliance, there is a high demand for a pharmacological active substance that preferably also has an active antidepressant component in addition to its analgesic action. The basis for such an antidepressant action in a pharmacological active substance is its capability to inhibit the reuptake of serotonin.

SUMMARY OF THE INVENTION

It is thus an object of the present invention to provide compounds that are particularly suitable as pharmaceutically active substances in pharmaceutical compositions, preferably in pharmaceutical compositions preferably for the simultaneous therapy of pain and depression. Moreover, the pharmaceutical compositions should also be suitable for regulation of 5-HT receptors and noradrenaline receptors, for the treatment of abuse of alcohol and/or of drugs and/or of medicines, for the inhibition and/or treatment of addiction to alcohol and/or to drugs and/or to medicines, for the inhibition and/or treatment of inflammations, for the inhibition and/or treatment of lethargy, for the inhibition and/or treatment of disturbances in food intake, preferably those selected from the group consisting of bulimia, anorexia, obesity, and ataxia, for the inhibition and/or treatment of catalepsy, for vigilance enhancement, for libido enhancement or for anxiolysis.

This object has been achieved by the provision of substituted 4,5,6,7-tetrahydrobenzthiazol-2-ylamine compounds of the general formula I given below.

It has now been found, surprisingly, that these compounds have an affinity to 5-HT receptors and noradrenaline receptors and lead to the inhibition of noradrenaline uptake (noradrenaline reuptake) and also the inhibition of 5-hydroxytryptamine (5-HT) uptake (5-HT reuptake).

The substituted 4,5,6,7-tetrahydrobenzthiazol-2-ylamine compounds of the invention of the general formula I given below are thus particularly suitable for use as pharmaceutically active substances in pharmaceutical compositions, preferably in those used for the inhibition and/or treatment of states of depression, for the treatment of abuse of alcohol and/or of drugs and/or of medicines, for the inhibition and/or treatment of addiction to alcohol and/or to drugs and/or to medicines, for the inhibition and/or treatment of inflammations, for the inhibition and/or treatment of lethargy, for the inhibition and/or treatment of disturbances in food intake, preferably selected from the group consisting of bulimia, anorexia, obesity, and cachexia, for the inhibition and/or treatment of catalepsy, for vigilance enhancement, for libido enhancement or for anxiolysis. Furthermore, the compounds of the invention also show a pronounced analgesic activity such that appropriate pharmaceutical compositions are also particularly suitable for the simultaneous therapy of pain and depression.

The present invention relates to substituted 4,5,6,7-tetrahydrobenzthiazol-2-ylamine compounds of the general formula I:

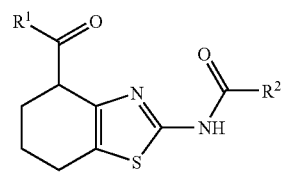

in which

R¹ represents an —NR³R⁴ group or an —NR⁵R⁶ group,

R² represents a linear or branched, saturated or unsaturated, optionally at least monosubstituted aliphatic radical, or a saturated or unsaturated, optionally at least monosubstituted cycloaliphatic radical, which optionally comprises at least one heteroatom as ring member and which can be bonded via an optionally at least monosubstituted alkylene group, alkenylene group, or alkynylene group, which groups optionally comprise at least one heteroatom as link, or an optionally at least monosubstituted aryl radical or heteroaryl radical which can be bonded via an optionally at least monosubstituted alkylene group, alkenylene group, or alkynylene group, optionally comprising at least one heteroatom as link, R³ represents a hydrogen atom, a linear or branched, saturated or unsaturated, optionally at least monosubstituted aliphatic radical, or a saturated or unsaturated, optionally at least monosubstituted, cycloaliphatic radical which optionally comprises at least one heteroatom as ring member and which can be bonded via an optionally at least monosubstituted alkylene group, alkenylene group, or alkynylene group, optionally comprising at least one heteroatom as link, or an optionally at least monosubstituted aryl radical or heteroaryl radical which can be bonded via an optionally at least monosubstituted alkylene group, alkenylene group, or alkynylene group, which groups optionally comprise at least one heteroatom as link, $R^4$ represents a hydrogen atom, or a linear or branched, saturated or unsaturated, optionally at least monosubstituted aliphatic radical, or a saturated or unsaturated, optionally at least monosubstituted cycloaliphatic radical which optionally comprises at least one heteroatom as ring member and which can be bonded via an optionally at least monosubstituted alkylene group, alkenylene group, or alkynylene group, which groups optionally comprise at least one heteroatom as link, or an optionally at least monosubstituted aryl radical or heteroaryl radical which can be bonded via an optionally at least monosubstituted alkylene group, alkenylene group, or alkynylene group, which groups optionally comprise at least one heteroatom as link, $R^5$ and $R^6$ together with the nitrogen atom to which they are attached form a saturated, unsaturated, or aromatic, optionally at least monosubstituted heterocyclic radical optionally comprising at least one further heteroatom as ring member, optionally in the form of their pure stereoisomers, particularly enantiomers or diastereoisomers, or in the form of their racemates or in the form of mixtures of the stereoisomers, particularly the enantiomers and/or diastereoisomers, in an arbitrary mixture ratio, or optionally in the form of appropriate salts or optionally in the form of appropriate solvates, in each case.

If one of the radicals $R^1$ to $R^6$ represents an aliphatic radical or comprises an aliphatic radical, this aliphatic radical—unless otherwise specified—can be monosubstituted or polysubstituted, for example, monosubstituted, disubstituted, trisubstituted, tetrasubstituted, or pentasubstituted, which substituents can be independently preferably selected from the group consisting of F, Cl, Br, $C_{1-6}$ alkoxy, hydroxy, CN, and $CF_3$, $CHF_3$, $CH_2F$, unsubstituted phenyl and —$NR^aR^b$, in which $R^a$ and $R^b$ can be selected independently from the group consisting of H, $C_{1-3}$ alkyl and unsubstituted phenyl.

Suitable aliphatic radicals, which can be monsubstituted or polysubstituted, for example, monosubstituted, disubstituted, trisubstituted, tetrasubstituted, or pentasubstituted, can, for example, be selected from the group consisting of methyl, ethyl, n-propyl, isopropyl, n-butyl, isobutyl, sec-butyl, tert-butyl, n-pentyl, 2,2-dimethylpropyl, penta-1,3-dienyl, n-hexyl, n-heptyl, n-octyl, n-nonyl, n-decyl, and vinyl, ethynyl, propenyl, propynyl, butenyl and butynyl.

If one of the radicals $R^1$ to $R^6$ represents a cycloaliphatic radical or comprises a cycloaliphatic radical, this cycloaliphatic radical can—unless otherwise specified—be monosubstituted or polysubstituted, for example, monosubstituted, disubstituted, trisubstituted, tetrasubstituted, or pentasubstituted, and the substituents may be independently preferably selected from the group consisting of F, Cl, Br, $C_{1-6}$ alkoxy, $C_{1-6}$ alkyl, hydroxy, and CN, $CF_3$, $CHF_3$, $CH_2F$, unsubstituted phenyl, —$NR^aR^b$ in which $R^a$ and $R^b$ are independently selected from the group consisting of H, $C_{1-3}$ alkyl and unsubstituted phenyl, and a phenyl radical or benzofuranyl radical optionally bonded via a methylene group, which may be monosubstituted or polysubstituted, for example, monosubstituted, disubstituted, trisubstituted, tetrasubstituted, or pentasubstituted by substituents selected from the group consisting of F, Cl, Br, $CF_3$, $CHF_2$, $CH_2F$, phenoxy, benzyloxy, phenyl, $C_{1-4}$ alkoxy, $C_{1-4}$ alkyl, and $C_{1-4}$ alkylthio.

Suitable cycloaliphatic radicals which may be monosubstituted or polysubstituted, for example, monosubstituted, disubstituted, trisubstituted, tetrasubstituted, or pentasubstituted, can, for example, be selected from the group consisting of cyclopropyl, cyclobutyl, cyclopentyl, cyclohexyl, cycloheptyl, cyclooctyl, cyclopentenyl, cyclohexenyl, cycloheptenyl, and cyclooctenyl.

If one of the radicals $R^1$ to $R^6$ represents an aryl radical or heteroaryl radical or comprises an aryl radical or heteroaryl radical, this aryl radical or heteroaryl radical can—unless otherwise specified—be monosubstituted or polysubstituted, for example, monosubstituted, disubstituted, trisubstituted, tetrasubstituted, or pentasubstituted, and the substituents may be independently preferably selected from the group consisting of F, Cl, Br, CF alkoxy, $C_{1-6}$ alkyl, hydroxy, CN, $CF_3$, $CHF_3$, $CH_2F$, unsubstituted phenyl, unsubstituted morpholynyl and —$NR^aR^b$ in which $R^a$ and $R^b$ may be independently selected from group consisting of H, $C_{1-3}$ alkyl and unsubstituted phenyl.

Suitable aryl groups that may be monosubstituted or polysubstituted, for example, monosubstituted, disubstituted, trisubstituted, tetrasubstituted, or pentasubstituted are particularly phenyl or naphthyl. Particularly suitable heteroaryl groups can be selected from the group consisting of pyridyl, furanyl, and thiophenyl.

If the radicals $R^5$ and $R^6$ form, together with the bridging nitrogen atom as ring member, a saturated, unsaturated, or aromatic heterocyclic radical which optionally comprises at least one further heteroatom as ring member, which heterocyclic radical is monosubstituted or polysubstituted, for example, monosubstituted, disubstituted, trisubstituted, tetrasubstituted, or pentasubstituted, the substituents may preferably be selected from the group consisting of a linear or branched, saturated or unsaturated, optionally at least monosubstituted aliphatic $C_{1-6}$ radical, a saturated or unsaturated, optionally at least monosubstituted five-membered, six-membered, or seven-membered cycloaliphatic radical optionally bonded via an optionally at least monosubstituted, $C_{1-6}$ alkylene group, $C_{2-6}$ alkenylene group, or $C_{2-6}$ alkynylene group, which groups optionally comprise at least one heteroatom or optionally at least one carbonyl group (C=O) as link, which cycloaliphatic radical optionally comprises at least one heteroatom as ring member and can be condensed with an optionally at least monosubstituted, for example, monosubstituted, disubstituted, trisubstituted, tetrasubstituted, or pentasubstituted, monocyclic or polycyclic ring system, and an optionally at least monosubstituted five-membered or six-membered aryl radical or heteroaryl radical bonded via an optionally at least monosubstituted, $C_{1-6}$ alkylene group, $C_{2-6}$ alkenylene group, or $C_{2-6}$ alkynylene group, which groups optionally comprise at least one heteroatom as link and can be condensed with an optionally at least monosubstituted, for example, monosubstituted, disubstituted, trisubstituted, tetrasubstituted, or pentasubstituted, monocyclic or polycyclic ring system. If the heterocycle formed by $R^5$ and $R^6$ comprises one or more further heteroatoms, for example, 1, 2, or 3, heteroatoms, the latter may be preferably selected from the group consisting of oxygen, nitrogen, and sulfur.

For the purposes of the present invention, a monocyclic or polycyclic ring system is to be understood as meaning monocyclic or polycyclic hydrocarbon groups, which are saturated, unsaturated, or aromatic and can optionally comprise one or more, for example, 1, 2, or 3, heteroatoms as ring members. Such a monocyclic or polycyclic ring system can be condensed with, ie anellated or bonded to, for example, a cycloaliphatic radical, an aryl radical, or a heteroaryl radical.

If a polycyclic ring system is present, the different rings can independently exhibit a different degree of saturation, ie they can be saturated, unsaturated, or aromatic. The heteroatoms can in each case be preferably selected from the group consisting of oxygen, nitrogen, and sulfur. Preferably, the respective rings of the ring system are five-membered or six-membered.

If one of the radicals $R_1$ to $R^6$ comprises an alkylene group, alkenylene group, or alkynylene group, these can in each case be branched or unbranched and optionally monosubstituted or polysubstituted, for example, monosubstituted, disubstituted, trisubstituted, tetrasubstituted, or pentasubstituted, and the substituents can be independently selected preferably from the group consisting of F, Cl, Br, $C_{1-6}$ alkoxy, hydroxy, CN, and $CF_3$, $CHF_2$, $CH_2F$, unsubstituted phenyl and —$NR^aR^b$ in which $R^a$ and $R^b$ can be independently selected from the group consisting of H, $C_{1-3}$ alkyl and unsubstituted phenyl.

If one of the radicals $R^1$ to $R^6$ represents a cycloaliphatic radical comprising at least one heteroatom or a heteroaryl group or comprises an alkylene group, alkenylene group, or alkynylene group containing at least one heteroatom as link or $R^5$ and $R^6$ form, together with the bridging nitrogen atom, a heterocycle, which exhibits one or more other heteroatoms, the respective heteroatoms can be preferably selected from the group consisting of oxygen, nitrogen, and sulfur.

Preferably, the aforementioned radicals can comprise 1, 2, or 3 heteroatoms as ring member(s) or link(s) which can be independently selected from the group consisting of oxygen, nitrogen, and sulfur.

Preferred substituted 4,5,6,7-tetrahydrobenzthiazol-2-ylamine compounds of the general formula I are those in which $R^2$ represents:

a linear or branched, saturated or unsaturated, optionally at least monosubstituted aliphatic $C_1$-$C_{10}$ radical, or a saturated or unsaturated, optionally at least monosubstituted cycloaliphatic radical, which optionally comprises at least one heteroatom as ring member and which can be bonded via an optionally at least monosubstituted $C_1$-$C_{10}$ alkylene group, $C_2$-$C_{10}$ alkenylene group, or $C_2$-$C_{10}$ alkynylene group, which groups optionally comprise at least one heteroatom as link, or an optionally at least monosubstituted five-membered to twelve-membered aryl radical or heteroaryl radical which can be bonded via an optionally at least monosubstituted $C_1$-$C_{10}$ alkylene group, $C_2$-$C_{10}$ alkenylene group, or $C_2$-$C_{10}$ alkynylene group, optionally comprising an at least monosubstituted heteroatom as link, preferably a linear or branched $C_1$-$C_{10}$ alkyl radical, a linear or branched $C_2$-$C_{10}$ alkenyl radical, or a saturated or unsaturated, optionally at least monosubstituted five-membered or six-membered cycloaliphatic radical, optionally comprising at least one heteroatom as ring member, which cycloaliphatic radical can be bonded via an optionally at least monosubstituted $C_1$-$C_5$ alkylene group or $C_1$-$C_2$ alkenylene group, which groups optionally comprise at least one heteroatom as link, or a phenyl group, 1-naphthyl group, 2-naphthyl group, 2-furanyl(2-furyl) group, 3-furanyl(3-furyl) group, 2-thiophenyl(2-thienyl) group, or 3-thiophenyl (3-thienyl) group, which groups are each at least monosubstituted and/or can be bonded via an optionally at least monosubstituted $C_1$-$C_5$ alkylene group or $C_2$-$C_5$ alkenylene group, which groups optionally comprise at least one heteroatom as link;

more preferably a linear or branched $C_1$-$C_5$ alkyl radical, a linear or branched $C_2$-$C_5$ alkenyl radical, a saturated or unsaturated, optionally at least monosubstituted six-membered cycloaliphatic radical optionally comprising at least one heteroatom as ring member, which six-membered cycloaliphatic radical can be bonded via a $C_1$-$C_3$ alkylene group, or a phenyl group, 1-naphthyl group, 2-naphthyl group, 2-furanyl group, 3-furanyl group, 2-thiophenyl group or 3-thiophenyl group, which groups are in each case at least monosubstituted and/or can be bonded via an optionally at least monosubstituted $C_1$-$C_5$ alkylene group or $C_2$-$C_5$ alkenylene group, which groups optionally comprise at least one heteroatom as link, and each of the remaining radicals $R^1$ and $R^3$ to $R^6$ has the meanings specified above, optionally in the form of their pure stereoisomers, particularly enantiomers or diastereoisomers, their racemates or in the form of mixtures of the stereoisomers, particularly the enantiomers and/or diastereoisomers, in an arbitrary mixture ratio, or optionally in the form of appropriate salts or in each case in the form of appropriate solvates.

Preference is also given to substituted 4,5,6,7-tetrahydrobenzthiazol-2-ylamine compounds of the general formula I, in which $R^3$ represents:

a hydrogen atom, a linear or branched, saturated or unsaturated, optionally at least monosubstituted aliphatic $C_1$-$C_{10}$ radical, or a saturated or unsaturated, optionally at least monosubstituted three-membered to seven-membered cycloaliphatic radical optionally comprising at least one heteroatom as ring member, which cycloaliphatic radical can be bonded via an optionally at least monosubstituted $C_1$-$C_{10}$ alkylene group, $C_2$-$C_{10}$ alkenylene group, or $C_2$-$C_{10}$ alkynylene group, which groups optionally comprise at least one heteroatom as link, or an optionally at least monosubstituted five-membered to twelve-membered aryl radical or heteroaryl radical, which can be bonded via an optionally at least monosubstituted $C_1$-$C_{10}$ alkylene group, $C_2$-$C_{10}$ alkenylene group, or $C_2$-$C_{10}$ alkynylene group, which groups optionally comprise at least one heteroatom as link;

preferably a hydrogen atom, or a linear or branched, optionally at least monosubstituted $C_1$-$C_{10}$ alkyl radical, or a saturated or unsaturated, optionally at least monosubstituted five-membered, six-membered, or seven-membered cycloaliphatic radical optionally comprising at least one heteroatom as ring member, which cycloaliphatic radical can be bonded via an optionally at least monosubstituted $C_1$-$C_{10}$ alkylene group, $C_2$-$C_{10}$ alkenylene group, or $C_2$-$C_{10}$ alkynylene group, which groups optionally comprise at least one heteroatom as link, or an optionally at least monosubstituted five-membered to twelve-membered aryl radical or heteroaryl radical, which can be bonded via an optionally at least monosubstituted $C_1$-$C_{10}$ alkylene group, $C_2$-$C_{10}$ alkenylene group, or $C_2$-$C_{10}$ alkynylene group, which groups optionally comprise at least one heteroatom as link, more preferably a hydrogen atom, or a linear or branched, optionally at least monosubstituted $C_{1-3}$ alkyl radical, or a cycloaliphatic radical bonded via a $C_{1-3}$ alkylene group and selected from the group consisting of

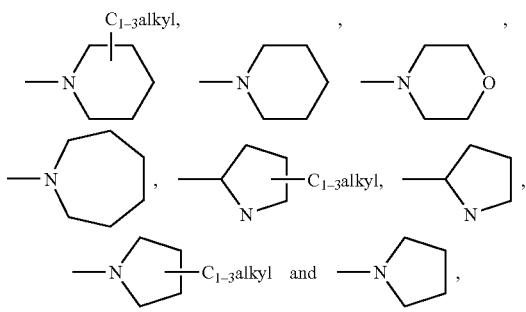

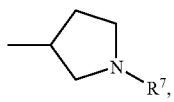

or a cycloaliphatic radical corresponding to the formula

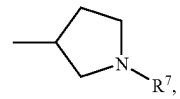

wherein
R⁷ represents a phenyl radical or benzofuranyl radical bonded via a methylene group and optionally monosubstituted or polysubstituted by the same or different substituents selected from the group consisting of F, Cl, Br, $CF_3$, $CHF_2$, $CH_2F$, phenoxy, benzyloxy, phenyl, $C_{1-4}$ alkoxy and $C_{1-4}$ alkylthio, or $R^3$ represents a phenyl radical optionally bonded via a methylene group, which phenyl radical can be monosubstituted or polysubstituted by the same or different substituents selected from the group consisting of di-($C_{1-3}$)-alkylamino, $C_{1-3}$ methoxy, and morpholynyl, and each of the radicals $R^1$, $R^2$, and $R^4$ to $R^6$ has the meanings specified above, optionally in the form of the pure stereoisomers thereof, particularly the enantiomers or diastereoisomers thereof, the racemates thereof or in the form of mixtures of the stereoisomers, particularly of the enantiomers and/or diastereoisomers, in an arbitrary mixture ratio, or optionally in the form of appropriate salts or in each case in the form of appropriate solvates.

Preference is also given to substituted 4,5,6,7-tetrahydrobenzthiazol-2-ylamine compounds of the general formula I, in which $R^4$ represents a hydrogen atom, or a linear or branched, saturated or unsaturated, optionally at least monosubstituted aliphatic $C_1$-$C_{10}$ radical, or a saturated or unsaturated, optionally at least monosubstituted three-membered to seven-membered cycloaliphatic radical which optionally comprises at least one heteroatom as ring member and which can be bonded via an optionally at least monosubstituted $C_1$-$C_{10}$ alkylene group, $C_2$-$C_{10}$ alkenylene group, or $C_2$-$C_{10}$ alkynylene group, which groups optionally comprise at least one heteroatom as link, or an optionally at least monosubstituted five-membered to twelve-membered aryl radical or heteroaryl radical which can be bonded via an optionally at least monosubstituted $C_1$-$C_{10}$ alkylene group, $C_2$-$C_{10}$ alkenylene group, or $C_2$-$C_{10}$ alkynylene group, which groups optionally comprise at least one heteroatom as link, preferably a hydrogen atom, or a linear or branched, optionally at least monosubstituted $C_1$-$C_{10}$alkyl radical, or a saturated or unsaturated, optionally at least monosubstituted five-membered, six-membered, or seven-membered cycloaliphatic radical which optionally comprises at least one heteroatom as ring member and which can be bonded via an optionally at least monosubstituted $C_1$-$C_{10}$alkylene group, $C_2$-$C_{10}$alkenylene group, or $C_2$-$C_{10}$alkynylene group, which groups optionally comprise at least one heteroatom as link, or an optionally at least monosubstituted five-membered to twelve-membered aryl radical or heteroaryl radical which can be bonded via an optionally at least monosubstituted $C_1$-$C_{10}$ alkylene group, $C_2$-$C_{10}$alkenylene group, or $C_2$-$C_{10}$alkynylene group, which groups optionally comprise at least one heteroatom as link, more preferably a linear or branched, optionally at least monosubstituted $C_{1-3}$ alkyl radical, or a cycloaliphatic radical bonded via a $C_{1-3}$ alkylene group and selected from the group consisting of

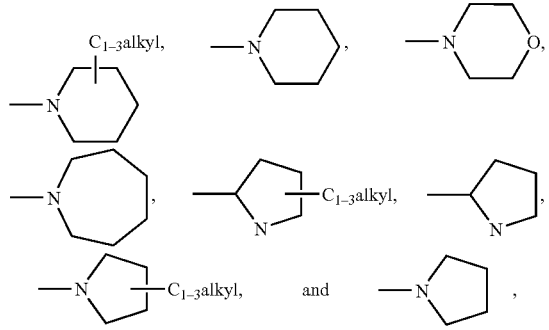

or a cycloaliphatic radical

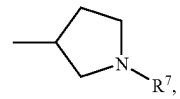

wherein
R⁷ represents a phenyl radical or benzofuranyl radical which is bonded via a methylene group and which can be monosubstituted or polysubstituted by the same or different substituents selected from the group consisting of F, Cl, Br, $CF_3$, $CHF_2$, $CH_2F$, phenoxy, benzyloxy, phenyl, $C_{1-4}$ alkoxy, or $C_{1-4}$ alkylthio, or $R^4$ represents a phenyl radical optionally bonded via a methylene group, which phenyl radical can be monosubstituted or polysubstituted by the same or different substituents selected from the group consisting of di-($C_{1-3}$)-alkylamino, $C_{1-3}$ methoxy, and morpholynyl, and $R^1$ to $R^3$, $R^5$, and $R^6$ have the meanings specified above, optionally in the form of the pure stereoisomers thereof, particularly the enantiomers or diastereoisomers thereof, the racemates thereof or in the form of mixtures of the stereoisomers, particularly of the enantiomers and/or diastereoisomers, in an arbitrary mixture ratio, or optionally in the form of appropriate salts or in each case in the form of appropriate solvates.

Preferred substituted 4,5,6,7-tetrahydrobenzthiazol-2-ylamine compounds of the general formula I are also those in which $R^5$ and $R^6$ together with the nitrogen atom to which they are attached form a saturated, unsaturated or aromatic, optionally at least monosubstituted five-membered, six-membered or seven-membered heterocyclic radical optionally comprising at least one further heteroatom as ring member, or or preferably together with the nitrogen atom to which they are attached form a radical selected from the group consisting of

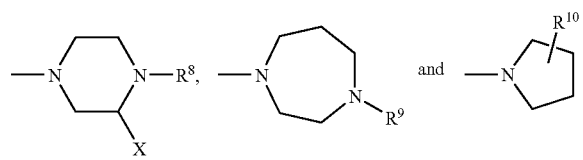

wherein

X represents hydrogen or a $C_{1-3}$ alkyl radical and preferably hydrogen or a methyl radical, $R^8$, $R^9$, and $R^{10}$ independently represent a linear or branched, saturated or unsaturated, optionally at least monosubstituted aliphatic $C_{1-6}$ radical, or a saturated or unsaturated, optionally at least monosubstituted five-membered, six-membered or seven-membered cycloaliphatic radical optionally comprising at least one heteroatom as ring member and optionally bonded via an optionally at least monosubstituted, $C_{1-6}$ alkylene group, $C_{2-6}$ alkenylene group, or $C_{2-6}$ alkynylene group, which groups optionally comprise at least one heteroatom or optionally at least one carbonyl group (C=O) as link, which cycloaliphatic radical can be condensed with an optionally at least monosubstituted, monocyclic or polycyclic ring system, or an optionally at least monosubstituted five-membered or six-membered aryl radical or heteroaryl radical optionally bonded via an optionally at least monosubstituted $C_{1-6}$ alkylene group, $C_{2-6}$ alkenylene group, or $C_{2-6}$ alkynylene group, which groups optionally comprise at least one heteroatom as link, which aryl or heteroaryl radical can be condensed with an optionally at least monosubstituted, monocyclic or polycyclic ring system, and preferably $R^8$ represents a $C_{1-3}$ alkyl radical optionally substituted by a di-($C_{1-3}$ alkyl)amino group, or an optionally at least monosubstituted phenyl radical, or an optionally at least monosubstituted naphthyl radical, or an optionally at least monosubstituted pyridynyl radical, or an optionally at least monosubstituted furanyl radical, or an optionally at least monosubstituted thiophenyl radical, or an optionally at least monosubstituted pyrroldynyl radical, or an optionally at least monosubstituted benzo[1,3]dioxolyl radical, or an optionally at least monosubstituted benzofuranyl radical, which cyclic radicals can be independently bonded via a $C_{1-3}$ alkylene group or a $C_{2-3}$ alkenylene group, which groups optionally comprise a carbonyl group (C=O) as link, and/or said radical may be monosubstituted or polysubstituted by the same or different substituents selected from the group consisting of —(C=O)—$C_{1-3}$ alkyl, $C_{1-3}$ alkoxy, $C_{1-3}$ alkyl, F, Cl, Br, —CN, $CF_3$, $CF_2H$, and $CFH_2$, $R^9$ represents a linear or branched $C_{1-3}$ alkyl radical, and $R^{10}$ represents a pyrrolidynyl radical bonded via a $C_{1-2}$ alkylene group, and each of the remaining radicals $R^1$ to $R^4$ has the meanings specified above, optionally in the form of the pure stereoisomers thereof, particularly the enantiomers or diastereoisomers thereof, the racemates thereof or in the form of mixtures of the stereoisomers, particularly of the enantiomers and/or diastereoisomers, in an arbitrary mixture ratio, or optionally in the form of appropriate salts or in each case in the form of appropriate solvates.

Special preference is given to substituted 4,5,6,7-tetrahydrobenzthiazol-2-ylamine compounds of the general formula I

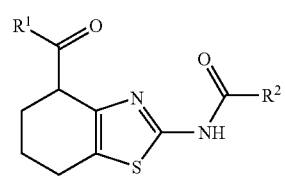

in which $R^1$ represents an —$NR^3R^4$ group or an —$NR^5R^6$ group, $R^2$ represents a linear or branched $C_{1-5}$ alkyl radical, or a linear or branched $C_{2-5}$ alkenyl radical, or a cyclohexyl radical optionally bonded via a —($CH_2$) group, a 1-naphthyl radical or 2-naphthyl radical optionally bonded via a —($CH_2$) group or —(CH=CH) group, or a 2-furanyl radical or 3-furanyl radical optionally bonded via a —($CH_2$) group or —(CH=CH) group, or a 2-thienyl radical or 3-thienyl radical optionally bonded via a —($CH_2$) group or —(CH=CH) group, or an unsubstituted or at least monosubstituted phenyl radical optionally bonded via a —($CH_2$) group, —($CH_2$)$_2$ group, —C(H)—($CH_3$) group or —($CH_2$)—O group, substituents therein being preferably independently selected from the group consisting of —F, —Cl, —Br, —$OCH_3$, —$OC_2H_5$, $CH_3$, and $C_2H_5$, $R^3$ represents a hydrogen atom or a methyl group, $R^4$ represents a linear or branched, optionally at least monosubstituted ($C_{1-3}$ alkyl radical, or a cycloaliphatic radical bonded via a $C_{1-3}$ alkylene group selected from the group consisting of

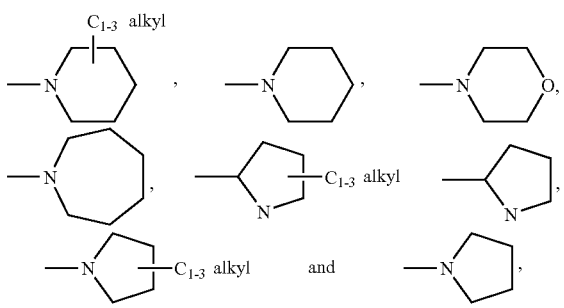

or a cycloaliphatic radical corresponding to the formula

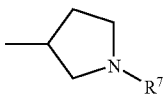

wherein

R⁷ represents a phenyl radical or benzofuranyl radical bonded via a methylene group and optionally independently monosubstituted or polysubstituted by the same or different substituents selected from the group consisting of F, Cl, Br, CF₃, CHF₂, CH₂F, phenoxy, benzyloxy, phenyl, C₁₋₄ alkoxy and C₁₋₄ alkylthio, or R⁴ represents a phenyl radical optionally bonded via a methylene group, which phenyl radical can be monosubstituted or polysubstituted by the same or different substituent selected from the group consisting of di-(C₁₋₃) alkylamino, C₁₋₃ methoxy, and morpholynyl, R⁵ and R⁶ together with the nitrogen atom to which they are attached form a radical selected from the group consisting of

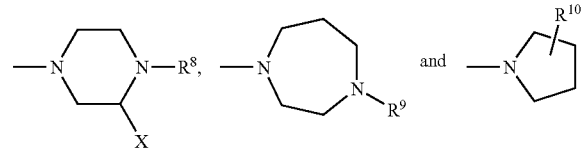

wherein

X represents a hydrogen atom or a methyl radical,

R⁸ represents a linear or branched C₁₋₃ alkyl radical optionally substituted by a dimethylamino group, or an optionally at least monosubstituted phenyl group, or an optionally at least monosubstituted naphthyl radical, or an optionally at least monosubstituted pyridynyl radical, or an optionally at least monosubstituted furanyl radical, or an optionally at least monosubstituted thiophenyl radical, or an optionally at least monosubstituted pyrroldynyl radical, or an optionally at least monosubstituted benzo[1,3]dioxolyl radical, or an optionally at least monosubstituted benzofuranyl radical, which cyclic radicals are independently bonded via a C₁₋₃ alkylene group or a C₂₋₃ alkenylene group, which groups optionally comprise a carbonyl group (C=O) as link, and/or said radical can be monosubstituted or polysubstituted by the same or different substituents selected from the group consisting of —(C=O)C₁₋₃ alkyl, C₁₋₃ alkoxy, F, Cl, Br, —CN, CF₃, CF₂H, and CFH₂, R⁹ represents a methyl radical or ethyl radical, and R¹⁰ represents a pyrrolidynyl radical bonded via a —(CH₂) group, optionally in the form of the pure stereoisomers thereof, particularly the enantiomers or diastereoisomers thereof, the racemates thereof or in the form of mixtures of the stereoisomers, particularly of the enantiomers and/or diastereoisomers, in an arbitrary mixture ratio, or in each case optionally in the form of appropriate salts or in each case optionally in the form of appropriate solvates.

The present invention also relates to substituted 4,5,6,7-tetrahydrobenzthiazol-2-ylamine compounds corresponding to formula I in which:

R¹ represents an —NR³R⁴ group or an —NR⁵R⁶ group,

R² represents a linear or branched, saturated or unsaturated, optionally substituted C₁₋₁₀ aliphatic radical; or an unsaturated or saturated, optionally substituted 3-membered, 4-membered, 5-membered, 6-membered, 7-membered, 8-membered, or 9-membered cycloaliphatic radical, which can be bonded via a linear or branched, optionally substituted C₁₋₅ alkylene group, C₂₋₅ alkenylene group or C₂₋₅ alkynylene group, each of these groups optionally comprising 1 or 2 heteroatom(s) as link(s), or an optionally substituted 5-membered to 14-membered aryl radical or heteroaryl radical, which can be bonded via a linear or branched, optionally substituted C₁₋₅ alkylene group, C₂₋₅ alkenylene group, or C₂₋₅ alkynylene group, which groups optionally comprise 1 or 2 heteroatom(s) as link(s);

R³ represents a hydrogen atom; or a linear or branched, saturated or unsaturated, optionally substituted C₁₋₁₀ aliphatic radical; or an unsaturated or saturated, optionally substituted three-membered, four-membered, five-membered, six-membered, seven-membered, eight-membered, or nine-membered cycloaliphatic radical, which can be bonded via a linear or branched, optionally substituted C₁₋₅ alkylene group, C₂₋₅ alkenylene group or C₂₋₅ alkynylene group which groups optionally comprise 1 or 2 heteroatom(s) as link(s), or an optionally substituted five-membered to fourteen-membered aryl radical or heteroaryl radical, which can be bonded via a linear or branched, optionally substituted C₁₋₅ alkylene group, C₂₋₅ alkenylene group or C₂₋₅ alkynylene group which groups optionally comprise 1 or 2 heteroatom(s) as link(s);

R⁵ and R⁶ together with the nitrogen atom to which they are attached form a saturated or unsaturated, optionally substituted four-membered, five-membered, six-membered, seven-membered, eight-membered or nine-membered heterocycloaliphatic radical, and each of said heterocycloaliphatic radicals can be substituted by a radical R⁸ and optionally by a radical X or a radical R⁹ or a radical R¹⁰ and/or can have further 1, 2, or 3 heteroatom(s) selected independently from the group consisting of oxygen, nitrogen, and sulfur as ring member(s);

X represents a linear or branched, saturated or unsaturated C₁₋₁₀ aliphatic radical;

R⁸, R⁹, and R¹⁰ independently represent a linear or branched, saturated or unsaturated, optionally substituted C₁₋₁₀ aliphatic racial, or an unsaturated or saturated, optionally substituted three-membered, four-membered, five-membered, six-membered, seven-membered, eight-membered or nine-membered cycloaliphatic radical, which radical can be bonded via a linear or branched, optionally substituted C₁₋₅ alkylene group, C₂₋₅ alkenylene group or C₂₋₅ alkynylene group, which groups optionally comprise 1 or 2 heteroatom(s) as link(s) and/or optionally comprise a carbonyl group (C=O) as link, and/or which radical can be condensed with a saturated, unsaturated or aromatic, optionally substituted mono or polycyclic ring system, or an optionally substituted five-membered to fourteen-membered aryl radical or heteroaryl radical, which radical can be bonded via a linear or branched, optionally substituted C₁₋₅ alkylene group, C₂₋₅ alkenylene group, or C₂₋₅ alkynylene group, which groups optionally comprise 1 or 2 heteroatom(s) as link(s) and/or optionally comprise a carbonyl group (C=O) as link, and/or which radical can be condensed with a saturated or unsaturated, optionally substituted monocyclic or polycyclic ring system;

wherein the aforementioned $C_{1-10}$ aliphatic radicals can in each case be substituted by 1, 2, 3, 4, or 5 substituents independently selected from the group consisting of F, Cl, Br, —CN, —NO$_2$, hydroxy, $C_{1-6}$ alkoxy, —NH$_2$, —NH—($C_{1-3}$ alkyl), —N($C_{1-3}$ alkyl)-($C_{1-3}$ alkyl), —NH-phenyl, —N($C_{1-3}$ alkyl)-phenyl, and —N(phenyl)$_2$;

the aforementioned cycloaliphatic radicals can in each case be substituted by 1, 2, 3, 4, or 5 substituents independently selected from the group consisting of F, Cl, Br, —CN, —CF$_3$, —CHF$_2$, —CH$_2$F, hydroxy, —$C_{1-6}$ alkoxy, —NH$_2$, —NH—($C_{1-3}$ alkyl), —N($C_{1-3}$ alkyl)-($C_{1-3}$ alkyl), —NH-phenyl, —N($C_{1-3}$ alkyl)-phenyl, —N(phenyl)$_2$, SH, —$C_{1-6}$ alkylthio, —$C_{1-6}$ alkyl, —(CH$_2$)benzo[b]furanyl, phenoxy, benzyloxy, phenyl, and benzyl, and in each case the cyclic moiety of the radicals phenoxy, benzyloxy, phenyl, —(CH$_2$)benzo[b]furanyl and benzyl can be substituted by 1, 2, 3, 4, or 5 substituents independently selected from the group consisting of F, Cl, Br, —$C_{1-4}$ alkyl, —CF$_3$, —CHF$_2$, —CH$_2$F, —$C_{1-4}$ alkoxy, —$C_{1-4}$ alkylthio, phenoxy, phenyl, and benzyloxy;

the aforementioned cycloaliphatic radicals can in each case comprise 1, 2, or 3 heteroatom(s) independently selected from the group consisting of oxygen, nitrogen, and sulfur;

the aforementioned $C_{1-5}$ alkylene groups, $C_{2-5}$ alkenylene groups or $C_{2-5}$ alkynylene groups can in each case be substituted by 1, 2, 3, 4, or 5 substituents independently selected from the group consisting of F, Cl, Br, —CN, —NO$_2$, hydroxy, $C_{1-6}$ alkoxy, —NH$_2$, —NH—($C_{1-3}$ alkyl), —N($C_{1-3}$ alkyl)-($C_{1-3}$ alkyl), —NH-phenyl, —N($C_{1-3}$ alkyl)-phenyl, N(phenyl)$_2$, and phenyl, and the aforementioned $C_{1-5}$ alkylene groups, $C_{2-5}$ alkenylene groups or $C_{2-5}$ alkynylene groups can in each case comprise 1 or 2 heteroatom(s) independently selected from the group consisting of oxygen, nitrogen, and sulfur;

the aforementioned aryl radical or heteroaryl radicals can in each case be substituted by 1, 2, 3, 4, or 5 substituents independently selected from the group consisting of F, Cl, Br, —CN, —CF$_3$, —CHF$_2$)—CH$_2$F, hydroxy, —$C_{1-6}$ alkoxy, —O—CF$_3$, —S—CF$_3$, SH, —$C_{1-6}$ alkylthio, —$C_{1-6}$ alkyl, —NH$_2$, —NH—($C_{1-3}$ alkyl), —N($C_{1-3}$ alkyl)-($C_{1-3}$ alkyl), —NH-phenyl, —N($C_{1-3}$ alkyl)-phenyl, N(phenyl)$_2$, phenoxy, benzyloxy, phenyl, benzyl, and morpholynyl, and in each case the cyclic moiety of the radicals phenoxy, benzyloxy, phenyl, and benzyl can be substituted by 1, 2, 3, 4, or 5 substituents independently selected from the group consisting of F, Cl, Br, hydroxy, —CF$_3$, —SF$_5$, —CN, —NO$_2$, —$C_{1-6}$ alkoxy, —O—CF$_3$, —S—CF$_3$, phenyl, and benzyloxy;

the aforementioned heteroaryl groups can in each case comprise 1, 2, 3, 4, or 5 heteroatom(s) as ring member(s) independently selected from the group consisting of oxygen, nitrogen, and sulfur;

the rings of the aforementioned monocyclic or polycyclic ring systems can optionally in each case be substituted by 1, 2, 3, 4, or 5 substituents independently selected from the group consisting of F, Cl, Br, —CN, —CF$_3$, —CHF$_2$, —CH$_2$F, hydroxy, —$C_{1-6}$ alkoxy, —O—CF$_3$, —S—CF$_3$, SH, —$C_{1-6}$ alkylthio, —$C_{1-6}$ alkyl, —NH$_2$, —NH—($C_{1-3}$ alkyl), —N($C_{1-3}$ alkyl)-($C_{1-3}$ alkyl), —NH-phenyl, —N($C_{1-3}$ alkyl)-phenyl, N(phenyl)$_2$, phenoxy, benzyloxy, phenyl, benzyl, and morpholynyl, and in each case the cyclic moiety of the radicals phenoxy, benzyloxy, phenyl, and benzyl can be substituted by 1, 2, 3, 4, or 5 substituents independently selected from the group consisting of F, Cl, Br, hydroxy, —CF$_3$, —SF$_5$, —CN, —NO$_2$, —$C_{1-6}$ alkoxy, —O—CF$_3$, —S—CF$_3$, phenyl, and benzyloxy, and the rings of the aforementioned monocyclic or polycyclic ring systems are each five-membered, six-membered, or seven-membered rings and can in each case comprise 1, 2, 3, 4, or 5 heteroatom(s) as ring member(s) which are independently selected from the group consisting of oxygen, nitrogen, and sulfur;

in each case optionally in the form of pure stereoisomers thereof particularly enantiomers or diastereoisomers, the racemates thereof or in the form of a mixture of stereoisomers, particularly the enantiomers and/or diastereoisomers, in an arbitrary mixture ratio, or in each case in the form of appropriate salts, or in each case in the form of appropriate solvates.

Preference is also given to substituted 4,5,6,7-tetrahydrobenzthiazol-2-ylamine compounds of the general formula I, in which $R^2$ represents an alkyl radical selected from the group consisting of methyl, ethyl, n-propyl, isopropyl, n-butyl, sec-butyl, isobutyl, tert-butyl, n-pentyl, sec-pentyl, (1,1)-dimethylpropyl, and n-hexyl, and the alkyl radical can in each case be substituted by 1, 2, 3, 4, or 5 substituents independently selected from the group consisting of F, Cl, Br, —CN, —NO$_2$, hydroxy, $C_{1-6}$ alkoxy, —NH$_2$, —NH—($C_{1-3}$ alkyl), —N($C_{1-3}$ alkyl)-($C_{1-13}$ alkyl), —NH-phenyl, —N($C_{1-3}$ alkyl)-phenyl, and —N(phenyl)$_2$; or an alkenyl radical selected from the group consisting of vinyl, 1-propenyl, 2-propenyl, 1-butenyl, 2-butenyl, 3-butenyl, 1-pentenyl, 2-pentenyl, and pent-1,3-dienyl, and the alkenyl radical can in each case be substituted by 1, 2, 3, 4, or 5 substituents independently selected from the group consisting of F, Cl, Br, —CN, —NO$_2$, hydroxy, $C_{1-6}$ alkoxy, —NH$_2$, —NH—($C_{1-3}$ alkyl), —N($C_{1-3}$ alkyl)-($C_{1-3}$ alkyl), —NH-phenyl, —N($C_{1-3}$ alkyl)-phenyl, and —N(phenyl)$_2$; or a (hetero)cycloaliphatic radical selected from the group consisting of cyclopropyl, cyclobutyl, cyclopentyl, cyclohexyl, cycloheptyl, cyclopentenyl, cyclohexenyl, cycloheptenyl, imidazolidynyl, tetrahydrofuranyl, tetrahydrothiophenyl, pyrrolidynyl, piperidynyl, morpholynyl, piperazynyl, thiomorpholynyl, tetrahydropyranyl, azepanyl, diazepanyl, and dithiolanyl, and the said (hetero)cycloaliphatic radical can in each case be bonded via a linear or branched, unsubstituted $C_{1-5}$ alkylene group and/or be substituted by 1, 2, 3, 4, or 5 substituents independently selected from the group consisting of F, Cl, Br, —CN, —CF$_3$, —CHF$_2$, —CH$_2$F, hydroxy, —$C_{1-6}$ alkoxy, —NH$_2$, —NH—($C_{1-3}$ alkyl), —N($C_{1-3}$ alkyl)-($C_{1-3}$ alkyl), —NH-phenyl, —N($C_{1-3}$ alkyl)-phenyl, —N(phenyl)$_2$, SH, —$C_{1-6}$ alkylthio, —$C_{1-6}$ alkyl, —(CH$_2$)benzo[b]furanyl, phenoxy, benzyloxy, phenyl, and benzyl, and in each case the cyclic moiety of the radicals phenoxy, benzyloxy, phenyl, —(CH$_2$)benzo[b]furanyl, and benzyl can be substituted by 1, 2, 3, 4, or 5 substituents independently selected from the group consisting of F, Cl, Br, —$C_{1-4}$ alkyl, —CF$_3$, —CHF$_2$, —CH$_2$F, —$C_{1-4}$ alkoxy, —$C_{1-4}$ alkylthio, phenoxy, phenyl, and benzyloxy; or a radical selected from the group consisting of phenyl, naphthyl, thiophenyl, furanyl, pyrrolyl, pyrazolyl, pyrazynyl, pyranyl, triazolyl, pyridynyl, imidazolyl, indolyl, isoindolyl, benzo[b]furanyl, benzo[b]thiophenyl, thiazolyl, oxazolyl, isoxazolyl, pyridazynyl, pyrazynyl, pyrimidynyl, indazolyl, quinazolynyl, quinolynyl, and isoquinolynyl, and the radical can in each case be bonded via a linear or branched, unsubstituted, $C_{1-5}$ alkylene group or $C_{2-5}$ alkenylene group, which groups optionally comprise an oxygen atom as link, and/or said radical can be substituted by 1, 2, 3, 4, or 5 substituents independently selected from the group consisting of F, Cl, Br, —CN, —$CF_3$, —$CHF_2$, —$CH_2F$, hydroxy, —$C_{1-6}$ alkoxy, —O—$CF_3$, —S—$CF_3$, SH, —$C_{1-6}$ alkylthio, —$C_{1-6}$ alkyl, —$NH_2$, —NH—($C_{1-3}$ alkyl), —N($C_{1-3}$ alkyl)-($C_{1-3}$ alkyl), —NH-phenyl, —N($C_{1-3}$ alkyl)-phenyl, N(phenyl)$_2$, phenoxy, benzyloxy, phenyl, benzyl, and morpholynyl, and in each case the cyclic moiety of the radicals phenoxy, benzyloxy, phenyl, and benzyl can be substituted by 1, 2, 3, 4, or 5 substituents independently selected from the group consisting of F, Cl, Br, hydroxy, —$CF_3$, —$SF_5$, —CN, —$NO_2$, —$C_{1-6}$ alkoxy, —O—$CF_3$, —S—$CF_3$, phenyl, and benzyloxy;

and preferably $R^2$ represents:
 an alkyl radical selected from the group consisting of methyl, ethyl, n-propyl, isopropyl, n-butyl, sec-butyl, isobutyl, tert-butyl, n-pentyl, sec-pentyl, (1,1)-dimethylpropyl, and n-hexyl; or
 an alkenyl radical selected from the group consisting of vinyl, 1-propenyl, 2-propenyl, 1-butenyl, 2-butenyl, 3-butenyl, 1-pentenyl, 2-pentenyl, and pent-1,3-dienyl; or
 a cycloaliphatic radical selected from the group consisting of cyclopropyl, cyclobutyl, cyclopentyl, cyclohexyl, cycloheptyl, cyclopentenyl, cyclohexenyl, and cycloheptenyl, which can be bonded via a —($CH_2$) group, —($CH_2$)$_2$ group, —CH($CH_3$) group, or —($CH_2$)$_3$ group and/or can be substituted by 1, 2, 3, 4, or 5 substituents independently selected from the group consisting of F, Cl, Br, —CN, —$CF_3$, —$CHF_2$, —$CH_2F$, hydroxy, —O—$CH_3$, —O—$C_2H_5$, —O—$C_3H_7$, —$NH_2$, —NH—$CH_3$, —NH—$C_2H_5$, —N—($CH_3$)$_2$, —N($C_2H_5$)$_2$, —N($CH_3$)—($C_2H_5$), —NH-phenyl, —N($CH_3$)-phenyl, —N($C_2H_5$)-phenyl, —N(phenyl)$_2$, SH, —S—$CH_3$, —S—$C_2H_5$, —S—$C_3H_7$, —S—C($CH_3$)$_3$, methyl, ethyl, n-propyl, isopropyl, n-butyl, sec-butyl, and tert-butyl; or
 a radical selected from the group consisting of phenyl, 1-naphthyl, 2-naphthyl, 2-furanyl, 3-furanyl, 2-thiophenyl, or 3-thiophenyl, which can be bonded via a —($CH_2$) group, —($CH_2$)$_2$ group, —($CH_2$)—O group, —CH($CH_3$) group, —(CH=CH) group, or —($CH_2$)$_3$ group and/or can be substituted by 1, 2, 3, 4, or 5 substituents independently selected from the group consisting of F, Cl, Br, —CN, —$CF_3$, —$CHF_2$, —$CH_2F$, hydroxy, —O—$CH_3$, —O—$C_2H_5$, —O—$C_3H_7$, —O—$CF_3$, —S—$CF_3$, —SH, —S—$CH_3$, —S—$C_2H_5$, —S—$C_3H_7$, —S—C($CH_3$)$_3$, methyl, ethyl, n-propyl, isopropyl, n-butyl, sec-butyl, tert-butyl, —$NH_2$, —NH—$CH_3$, —NH—$C_2H_5$, —N—($CH_3$)$_2$, —N($C_2H_5$)$_2$, —N($CH_3$)—($C_2H_5$), —NH-phenyl, —N($CH_3$)-phenyl, —N($C_2H_5$)-phenyl, —N(phenyl)$_2$, phenoxy, benzyloxy, phenyl, benzyl, and morpholynyl;

and more preferably $R^2$ represents:
 an alkyl radical selected from the group consisting of n-propyl, isopropyl, n-butyl, sec-butyl, isobutyl, tert-butyl, n-pentyl, sec-pentyl, and (1,1)-dimethylpropyl; or
 an alkenyl radical selected from the group consisting of 1-pentenyl, 2-pentenyl and pent-1,3-dienyl; or
 a cycloaliphatic radical selected from the group consisting of cyclopentyl, cyclohexyl, and cycloheptyl, which is bonded via a —($CH_2$) group; or
 a radical selected from the group consisting of phenyl, 1-naphthyl, 2-naphthyl, 2-furanyl, 3-furanyl, 2-thiophenyl, and 3-thiophenyl, which can be bonded via a —($CH_2$) group, —($CH_2$)$_2$ group, —($CH_2$)—O group, —CH($CH_3$) group, —(CH=CH) group, or —($CH_2$)$_3$ group and/or can be substituted by 1, 2, or 3 substituents independently selected from the group consisting of F, Cl, Br, —O—$CH_3$, —O—$C_2H_5$, methyl, ethyl, n-propyl, and isopropyl;

and each of the remaining radicals $R^1$, $R^3$ to $R^6$, X and $R^8$ to $R^{10}$ have the meanings specified above, optionally in the form of the pure stereoisomers thereof, particularly the enantiomers or diastereoisomers thereof, the racemates thereof or in the form of mixtures of the stereoisomers, particularly of the enantiomers and/or diastereoisomers, in an arbitrary mixture ratio, or optionally in the form of appropriate salts or in each case in the form of appropriate solvates.

Special preference is likewise given to substituted 4,5,6,7-tetrahydrobenzthiazol-2-ylamine compounds of the general formula I, in which
$R^3$ represents a hydrogen atom; or an alkyl radical selected from the group consisting of methyl, ethyl, n-propyl, isopropyl, n-butyl, sec-butyl, isobutyl, tert-butyl, n-pentyl, sec-pentyl, (1,1)-dimethylpropyl, and n-hexyl, and the alkyl radical can in each case be substituted by 1, 2, 3, 4, or 5 substituents independently selected from the group consisting of F, Cl, Br, —CN, —$NO_2$, hydroxy, $C_{1-6}$ alkoxy, —$NH_2$, —NH—($C_{1-3}$ alkyl), —N($C_{1-3}$ alkyl)-($C_{1-3}$ alkyl), —NH-phenyl, —N($C_{1-3}$ alkyl)-phenyl, and —N(phenyl)$_2$; or
 a (hetero)cycloaliphatic radical selected from the group consisting of cyclopropyl, cyclobutyl, cyclopentyl, cyclohexyl, cycloheptyl, cyclopentenyl, cyclohexenyl, cycloheptenyl, imidazolidynyl, tetrahydrofuranyl, tetrahydrothiophenyl, pyrrolidynyl, piperidynyl, morpholynyl, piperazynyl, thiomorpholynyl, tetrahydropyranyl, azepanyl, diazepanyl, and dithiolanyl, and the (hetero)cycloaliphatic radical can in each case be bonded via a linear or branched, unsubstituted $C_{1-5}$ alkylene group and/or can be substituted by 1, 2, 3, 4, or 5 substituents independently selected from the group consisting of F, Cl, Br, —CN, —$CF_3$, —$CHF_2$, —$CH_2F$, hydroxy, —$C_{1-6}$ alkoxy, —$NH_2$, —NH—($C_{1-3}$ alkyl), —N($C_{1-3}$ alkyl)-($C_{1-3}$ alkyl), —NH-phenyl, —N($C_{1-3}$ alkyl)-phenyl, —N(phenyl)$_2$, —SH, —$C_{1-6}$ alkylthio, —$C_{1-6}$ alkyl, —($CH_2$)benzo[b]furanyl, phenoxy, benzyloxy, phenyl, and benzyl, and in each case the cyclic moiety of the radicals phenoxy, benzyloxy, phenyl, —($CH_2$)benzo[b]furanyl and benzyl can be substituted by 1, 2, 3, 4, or 5 substituents independently selected from the group consisting of F, Cl, Br, —$C_{1-4}$ alkyl, —$CF_3$, —$CHF_2$, —$CH_2F$, —$C_{1-4}$ alkoxy, —$C_{1-4}$ alkylthio, phenoxy, phenyl, and benzyloxy; or
 a radical selected from the group consisting of phenyl, naphthyl, thiophenyl, furanyl, pyrrolyl, pyrazolyl, pyrazynyl, pyranyl, triazolyl, pyridynyl, imidazolyl, indolyl, isoindolyl, benzo[b]furanyl, benzo[b]thiophenyl, thiazolyl, oxazolyl, isoxazolyl, pyridazynyl, pyrazynyl, pyrimidynyl, indazolyl, quinazolynyl, quinolynyl, and isoquinolynyl, and the radical can in each case be bonded via a linear or branched, unsubstituted, $C_{1-5}$ alkylene group or $C_{2-5}$ alkenylene group, which groups optionally comprise an oxygen atom as link, and/or said radical can be substituted by 1, 2, 3, 4, or 5 substituents independently selected from the group consisting of F, Cl, Br, —CN, —$CF_3$, —$CHF_2$, —$CH_2F$, hydroxy, —$C_{1-6}$ alkoxy, —O—$CF_3$, —S—$CF_3$, —SH, —$C_{1-6}$ alkylthio, —$C_{1-6}$ alkyl, —$NH_2$, —NH—($C_{1-3}$ alkyl), —N($C_{1-3}$ alkyl)-($C_{1-3}$ alkyl), —NH-phenyl, —N($C_{1-3}$ alkyl)-phenyl, N(phenyl)$_2$, phenoxy, benzyloxy, phenyl, benzyl, and morpholynyl, and in each case the cyclic moiety of the radicals phenoxy, benzyloxy, phenyl, and benzyl can be substituted by 1, 2, 3, 4, or 5 substituents independently selected from the group consisting of F, Cl, Br, hydroxy, —$CF_3$, —$SF_5$, —CN, —$NO_2$, —$C_{1-6}$ alkoxy, —O—$CF_3$, —S—$CF_3$) phenyl, and benzyloxy;

preferably $R^3$ represents:

a hydrogen atom; or an alkyl radical selected from the group consisting of methyl, ethyl, n-propyl, n-butyl and n-pentyl, and the alkyl radical can in each case be substituted by 1 or 2 substituents independently selected from the group consisting of $NH_2$, —NH—$CH_3$, —NH—$C_2H_5$, —N—($CH_3$)$_2$, —N($C_2H_5$)$_2$, —N($CH_3$)($C_2H_5$), —NH-phenyl, —N($CH_3$)-phenyl, —N($C_2H_5$)-phenyl, and —N(phenyl)$_2$; or a radical selected from the group consisting of

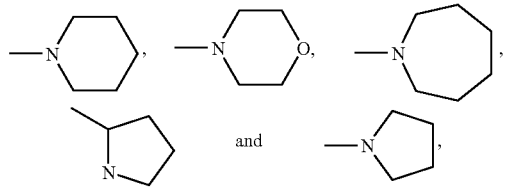

which can be bonded via a —($CH_2$) group, —($CH_2$)$_2$ group, —($CH_2$)—O group, —CH($CH_3$) group, —(CH=CH) group, or —($CH_2$)$_3$ group and/or can be substituted by 1, 2, or 3 substituents independently selected from the group consisting of methyl, ethyl, and n-propyl; or a radical corresponding to the formula:

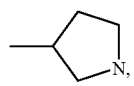

which can be substituted on the nitrogen atom by a substituent selected from the group consisting of —($CH_2$)benzo[b]furanyl and benzyl, and in each case the cyclic moiety of the radicals —($CH_2$)benzo[b]furanyl and benzyl can be substituted by 1, 2, 3, 4 or 5 substituents independently selected from the group consisting of F, Cl, Br, —$C_{1-4}$ alkyl, —$CF_3$, —$CHF_2$, —$CH_2F$, —$C_{1-4}$ alkoxy, —$C_{1-4}$ alkylthio, phenoxy, phenyl, and benzyloxy; or a radical selected from the group consisting of phenyl and naphthyl, which radical can in each case be bonded via a —($CH_2$) group, —($CH_2$)$_2$ group, or —($CH_2$)$_3$ group and/or can be substituted by 1, 2, or 3 substituents independently selected from the group consisting of —$C_{1-6}$ alkoxy, —$C_{1-6}$ alkyl, —$NH_2$, —NH—($C_{1-3}$ alkyl), —N($C_{1-3}$ alkyl)-($C_{1-3}$ alkyl), —NH-phenyl, —N($C_{1-3}$ alkyl)-phenyl, N(phenyl)$_2$, and morpholynyl;

more preferably $R^3$ represents:

a hydrogen atom; or a radical selected from the group consisting of methyl, ethyl, n-propyl, —($CH_2$)—N($CH_3$)$_2$, —($CH_2$)—($CH_2$)—N($CH_3$)$_2$, —($CH_2$)—($CH_2$)—($CH_2$)—N($CH_3$)$_2$, —($CH_2$)—($CH_2$)—N($C_2H_5$)$_2$, —($CH_2$)—($CH_2$)—($CH_2$)—N($C_2H_5$)$_2$, —($CH_2$)—($CH_2$)—N($CH_3$)-(phenyl), and —($CH_2$)—($CH_2$)—($CH_2$)—N($CH_3$)-(phenyl); or a radical selected from the group consisting of

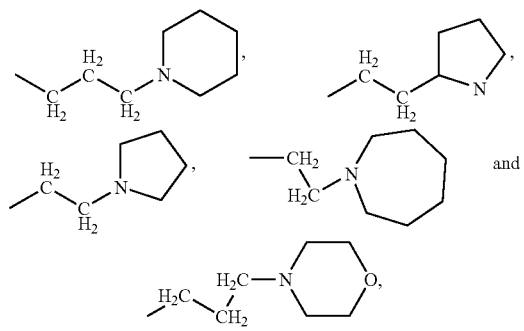

which optionally can be substituted by a methyl group; or a radical corresponding to the formula

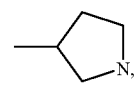

which optionally can be substituted on the nitrogen atom by a substituent selected from the group consisting of —($CH_2$)benzo[b]furanyl and benzyl, and in each case the cyclic moiety of the radicals —($CH_2$)benzo[b]furanyl and benzyl can be substituted by 1, 2, or 3 substituents independently selected from the group consisting of F, Cl, Br, —O—$CH_3$, —O—$C_2H_5$, —O—$C_3H_7$, —S—$CH_3$, —S—$C_2H_5$, —S—$C_3H_7$, —S—C($CH_3$)$_3$, methyl, ethyl, n-propyl, isopropyl, n-butyl, phenoxy and benzyloxy; or a radical selected from the group consisting of phenyl and benzyl, and the cyclic moiety of the radicals phenyl and benzyl can be substituted by 1, 2, or 3 substituents independently selected from the group consisting of —O—$CH_3$, —O—$C_2H_5$, —O—$C_3H_7$, —N—($CH_3$)$_2$, —N($C_2H_5$)$_2$ and morpholynyl;

most preferably $R^3$ represents a hydrogen atom or a methyl radical; and each of the remaining radicals $R^1$, $R^2$, $R^4$ to $R^6$, X and $R^8$ to $R^{10}$ have the meanings specified above, optionally in the form of the pure stereoisomers thereof, particularly the enantiomers or diastereoisomers thereof, the racemates thereof or in the form of mixtures of the stereoisomers, particularly of the enantiomers and/or diastereoisomers, in an arbitrary mixture ratio, or optionally in the form of appropriate salts or in each case in the form of appropriate solvates.

Preference is also given to substituted 4,5,6,7-tetrahydrobenzthiazol-2-ylamine compounds of the general formula I, in which $R^4$ represents a hydrogen atom; or an alkyl radical selected from the group consisting of methyl, ethyl, n-propyl, isopropyl, n-butyl, sec-butyl, isobutyl, tert-butyl, n-pentyl, sec-pentyl, (1,1)-dimethylpropyl, and n-hexyl, and the alkyl radical can in each case be substituted by 1, 2, 3, 4 or 5 substituents independently selected from the group consisting of F, Cl, Br, —CN, —NO$_2$, hydroxy, $C_{1-6}$ alkoxy, —NH$_2$, —NH—($C_{1-3}$ alkyl), —N($C_{1-3}$ alkyl)-($C_{1-3}$ alkyl), —NH-phenyl, —N($C_{1-3}$ alkyl)-phenyl, and —N(phenyl)$_2$; or an alkenyl radical selected from the group consisting of vinyl, 1-propenyl, 2-propenyl, 1-butenyl, 2-butenyl, 3-butenyl, 1-pentenyl, 2-pentenyl, and pent-1,3-dienyl, and the alkenyl radical can in each case be substituted by 1, 2, 3, 4, or 5 substituents independently selected from the group consisting of F, Cl, Br, —CN, —NO$_2$, hydroxy, $C_{1-6}$ alkoxy, —NH$_2$, —NH—($C_{1-3}$ alkyl), —N($C_{1-3}$ alkyl)-($C_{1-3}$ alkyl), —NH-phenyl, —N($C_{1-3}$ alkyl)phenyl, and —N(phenyl)$_2$; or a (hetero)cycloaliphatic radical selected from the group consisting of cyclopropyl, cyclobutyl, cyclopentyl, cyclohexyl, cycloheptyl, cyclopentenyl, cyclohexenyl, cycloheptenyl, imidazolidynyl, tetrahydrofuranyl, tetrahydrothiophenyl, pyrrolidynyl, piperidynyl, morpholynyl, piperazynyl, thiomorpholynyl, tetrahydropyranyl, azepanyl, diazepanyl, and dithiolanyl, and the (hetero)cycloaliphatic radical can in each case be bonded via a linear or branched, unsubstituted $C_{1-5}$ alkylene group and/or can be substituted by 1, 2, 3, 4, or 5 substituents independently selected from the group consisting of F, Cl, Br, —CN, —CF$_3$, —CHF$_2$, —CH$_2$F, hydroxy, —$C_{1-6}$ alkoxy, —NH$_2$, —NH—($C_{1-3}$ alkyl), —N($C_{1-3}$ alkyl)-($C_{1-3}$ alkyl), —NH-phenyl, —N($C_{1-3}$ alkyl), phenyl, —N(phenyl)$_2$, —SH, —$C_{1-6}$ alkylthio, —$C_{1-6}$ alkyl, —(CH$_2$)benzo[b]furanyl, phenoxy, benzyloxy, phenyl, and benzyl, and in each case the cyclic moiety of the radicals phenoxy, benzyloxy, phenyl, —(CH$_2$)benzo[b]furanyl, and benzyl can be substituted by 1, 2, 3, 4, or 5 substituents independently selected from the group consisting of F, Cl, Br, —$C_{1-4}$ alkyl, —CF$_3$, —CHF$_2$, —CH$_2$F, —$C_{1-4}$ alkoxy, —$C_{1-4}$ alkylthio, phenoxy, phenyl, and benzyloxy; or a radical selected from the group consisting of phenyl, naphthyl, thiophenyl, furanyl, pyrrolyl, pyrazolyl, pyrazynyl, pyranyl, triazolyl, pyridynyl, imidazolyl, indolyl, isoindolyl, benzo[b]furanyl, benzo[b]thiophenyl, thiazolyl, oxazolyl, isoxazolyl, pyridazynyl, pyrazynyl, pyrimidynyl, indazolyl, quinazolynyl, quinolynyl, and isoquinolynyl, and the radical can in each case be bonded via a linear or branched, unsubstituted $C_{1-5}$ alkylene group or $C_{2-5}$ alkenylene group, which groups optionally comprise an oxygen atom as link, and/or said radical can be substituted by 1, 2, 3, 4, or 5 substituents independently selected from the group consisting of F, Cl, Br, —CN, —CF$_3$, —CHF$_2$, —CH$_2$F, hydroxy, —$C_{1-6}$ alkoxy, —O—CF$_3$, —S—CF$_3$, —SH, —$C_{1-6}$ alkylthio, —$C_{1-6}$ alkyl, —NH$_2$, —NH—($C_{1-3}$ alkyl), —N($C_{1-3}$ alkyl)-($C_{1-3}$ alkyl), —NH-phenyl, —N($C_{1-3}$ alkyl)-phenyl, N(phenyl)$_2$, phenoxy, benzyloxy, phenyl, benzyl, and morpholynyl, and in each case the cyclic moiety of the radicals phenoxy, benzyloxy, phenyl, and benzyl can be substituted by 1, 2, 3, 4, or 5 substituents independently selected from the group consisting of F, Cl, Br, hydroxy, —CF$_3$, —SF$_5$, —CN, —NO$_2$, —$C_{1-6}$ alkoxy, —O—CF$_3$, —S—CF$_3$, phenyl, and benzyloxy;

preferably $R^4$ represents a hydrogen atom; or an alkyl radical selected from the group consisting of methyl, ethyl, n-propyl, n-butyl, and n-pentyl, which alkyl radical can in each case be substituted by 1 or 2 substituents independently selected from the group consisting of NH$_2$, —NH—CH$_3$, —NH—C$_2$H$_5$, —N—(CH$_3$)$_2$, —N(C$_2$H$_5$)$_2$, —N(CH$_3$) (C$_2$H$_5$), —NH-phenyl, —N(CH$_3$)-phenyl, —N(C$_2$H$_5$)-phenyl, and —N(phenyl)$_2$, or a radical selected from the group consisting of

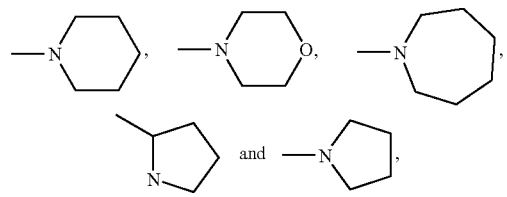

which optionally can be bonded via a —(CH$_2$) group, —(CH$_2$)$_2$ group, —(CH$_2$)—O group, —CH(CH$_3$) group, —(CH═CH) group, or —(CH$_2$)$_3$ group and/or can be substituted by 1, 2, or 3 substituents independently selected from the group consisting of methyl, ethyl, and n-propyl; or a radical corresponding to the formula

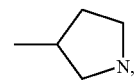

which optionally can be substituted by a substituent selected from the group consisting of —(CH$_2$)benzo[b]furanyl and benzyl, and in each case the cyclic moiety of the radicals —(CH$_2$)benzo[b]furanyl and benzyl can be substituted by 1, 2, 3, 4 or 5 substituents independently selected from the group consisting of F, Cl, Br, —$C_{1-4}$ alkyl, —CF$_3$, —CHF$_2$, —CH$_2$F, —$C_{1-4}$ alkoxy, —$C_{1-4}$ alkylthio, phenoxy, phenyl, and benzyloxy; or a radical selected from the group consisting of phenyl and naphthyl, and the radical can in each case be bonded via a —(CH$_2$) group, —(CH$_2$)$_2$ group, or —(CH$_2$)$_3$ group and/or can be substituted by 1, 2, or 3 substituents independently selected from the group consisting of —$C_{1-6}$ alkoxy, —$C_{1-6}$ alkyl, —NH$_2$, —NH—($C_{1-3}$ alkyl), —N($C_{1-3}$ alkyl)-($C_{1-3}$ alkyl), —NH-phenyl, —N($C_{1-3}$ alkyl)-phenyl, N(phenyl)$_2$, and morpholynyl;

more preferably $R^4$ represents:

a radical selected from the group consisting of methyl, ethyl, n-propyl, —(CH$_2$)—N(CH$_3$)$_2$, —(CH$_2$)—(CH$_2$)—N(CH$_3$)$_2$, —(CH$_2$)—(CH$_2$)—(CH$_2$)—N(CH$_3$)$_2$, —(CH$_2$)—(CH$_2$)—N(C$_2$H$_5$)$_2$, —(CH$_2$)—(CH$_2$)—N(C$_2$H$_5$)$_2$, —(CH$_2$)—(CH$_2$)—N(CH$_3$)-(phenyl), and —(CH$_2$)—(CH$_2$)—(CH$_2$)—N(CH$_3$)-(phenyl); or a radical selected from the group consisting of

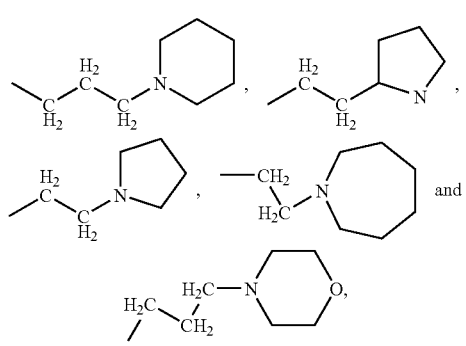

which optionally can be substituted by a methyl group; or
a radical corresponding to the formula

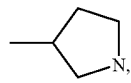

which optionally can be substituted on the nitrogen atom by a substituent selected from the group consisting of —(CH$_2$)benzo[b]furanyl and benzyl, and in each case the cyclic moiety of the radicals —(CH$_2$)benzo[b]furanyl and benzyl can be substituted by 1, 2, or 3 substituents independently selected from the group consisting of F, Cl, Br, —O—CH$_3$, —O—C$_2$H$_5$, —O—C$_3$H$_7$, —S—CH$_3$, —S—C$_2$H$_5$, —S—C$_3$H$_7$, —S—C(CH$_3$)$_3$, methyl, ethyl, n-propyl, isopropyl, n-butyl, phenoxy and benzyloxy; or a radical selected from the group consisting of phenyl and benzyl, and the cyclic moiety of the radicals phenyl and benzyl can be substituted by 1, 2, or 3 substituents independently selected from the group consisting of —O—CH$_3$, —O—C$_2$H$_5$, —O—C$_3$H$_7$, —N—(CH$_3$)$_2$, —N(C$_2$H$_5$)$_2$, and morpholynyl;

and each of the remaining radicals R$^1$ to R$^3$, R$^5$ and R$^6$, X, and R$^8$ to R$^{10}$ has the meanings specified above, optionally in the form of the pure stereoisomers thereof, particularly the enantiomers or diastereoisomers thereof, the racemates thereof or in the form of mixtures of the stereoisomers, particularly of the enantiomers and/or diastereoisomers, in an arbitrary mixture ratio, or optionally in the form of appropriate salts or in each case in the form of appropriate solvates.

Preference is also given to substituted 4,5,6,7-tetrahydrobenzthiazol-2-ylamine compounds of the general formula I, in which R$^5$ and R$^6$ together with the nitrogen atom to which they are attached form a heterocycloaliphatic radical selected from the group consisting of piperazynyl, morpholynyl, thiomorpholynyl, pyrrolidynyl, azepanyl, diazepanyl, and piperidynyl, and the heterocycloaliphatic radicals can be substituted by a radical R$^8$ and optionally a radical X or a radical R$^9$ or a radical R$^{10}$;

more preferably R$^5$ and R$^6$ together with the nitrogen atom to which they are attached form one of the following radicals

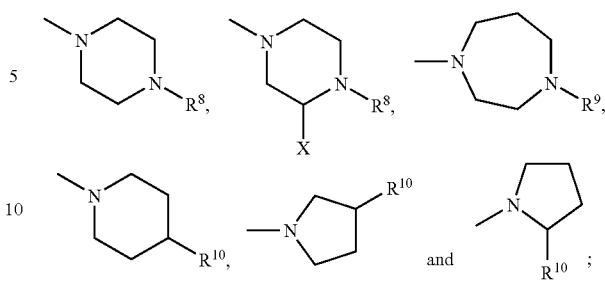

and each of the remaining radicals R$^1$ to R$^4$, X and R$^8$ to R$^{10}$ has the meanings specified above, optionally in the form of the pure stereoisomers thereof, particularly the enantiomers or diastereoisomers thereof, the racemates thereof or in the form of mixtures of the stereoisomers, particularly of the enantiomers and/or diastereoisomers, in an arbitrary mixture ratio, or optionally in the form of appropriate salts or in each case in the form of appropriate solvates.

Preference is also given to substituted 4,5,6,7-tetrahydrobenzthiazol-2-ylamine compounds of the general formula I, in which X represents an alkyl radical selected from the group consisting of methyl, ethyl, n-propyl, isopropyl, n-butyl, sec-butyl, isobutyl, tert-butyl, n-pentyl, sec-pentyl, (1,1)-dimethylpropyl, and n-hexyl; preferably X represents a methyl group; and each of the remaining radicals R$^1$ to R$^6$ and R$^8$ to R$^{10}$ has the meanings specified above, optionally in the form of the pure stereoisomers thereof, particularly the enantiomers or diastereoisomers thereof, the racemates thereof or in the form of mixtures of the stereoisomers, particularly of the enantiomers and/or diastereoisomers, in an arbitrary mixture ratio, or optionally in the form of appropriate salts or in each case in the form of appropriate solvates.

Preference is also given to substituted 4,5,6,7-tetrahydrobenzthiazol-2-ylamine compounds of the general formula I, in which R$^8$, R$^9$, and R$^{10}$ each independently represent an alkyl radical selected from the group consisting of methyl, ethyl, n-propyl, isopropyl, n-butyl, sec-butyl, isobutyl, tert-butyl, n-pentyl, sec-pentyl, (1,1)-dimethylpropyl, and n-hexyl, and the alkyl radical can in each case be substituted by 1, 2, 3, 4, or 5 substituents independently selected from the group consisting of F, Cl, Br, —CN, —NO$_2$, hydroxy, C$_{1-6}$ alkoxy, —NH$_2$, —NH—(C$_{1-3}$ alkyl), —N(C$_{1-3}$ alkyl)-(C$_{1-3}$ alkyl), —NH-phenyl, —N(C$_{1-3}$ alkyl)-phenyl, and —N(phenyl)$_2$; or an alkenyl radical selected from the group consisting of vinyl, 1-propenyl, 2-propenyl, 1-butenyl, 2-butenyl, 3-butenyl, 1-pentenyl, 2-pentenyl, and pent-1,3-dienyl, and the alkenyl radical can in each case be substituted by 1, 2, 3, 4, or 5 substituents independently selected from the group consisting of F, Cl, Br, —CN, —NO$_2$, hydroxy, C$_{1-6}$ alkoxy, —NH$_2$, —NH—(C$_{1-3}$ alkyl), —N(C$_{1-3}$ alkyl)-(C$_{1-3}$ alkyl), —NH-phenyl, —N(C$_{1-3}$ alkyl)-phenyl, and —N(phenyl)$_2$; or a (hetero)cycloaliphatic radical selected from the group consisting of cyclopropyl, cyclobutyl, cyclopentyl, cyclohexyl, cycloheptyl, cyclopentenyl, cyclohexenyl, cycloheptenyl, imidazolidynyl, tetrahydrofuranyl, tetrahydrothiophenyl, pyrrolidynyl, piperidynyl, morpholynyl, piperazynyl, thiomorpholynyl, tetrahydropyranyl, azepanyl, diazepanyl, and dithiolanyl, which (hetero)cycloaliphatic radical can in each case be bonded via a linear or branched $C_{1-5}$ alkylene group optionally comprising a carbonyl group (C=O) as link and/or can be substituted by 1, 2, 3, 4, or 5 substituents independently selected from the group consisting of F, Cl, Br, —CN, —CF$_3$, —CHF$_2$, —CH$_2$F, hydroxy, —C$_{1-6}$ alkoxy, —NH$_2$, —NH—(C$_{1-3}$ alkyl), —N(C$_{1-3}$ alkyl)-(C$_{1-3}$ alkyl), —NH-phenyl, —N(C$_{1-3}$ alkyl)-phenyl, —N(phenyl)$_2$, —SH, —C$_{1-6}$ alkylthio, —C$_{1-6}$ alkyl, —(CH$_2$)benzo[b]furanyl, phenoxy, benzyloxy, phenyl, and benzyl, and in each case the cyclic moiety of the radicals phenoxy, benzyloxy, phenyl, —(CH$_2$)benzo[b]furanyl, and benzyl can be substituted by 1, 2, 3, 4, or 5 substituents independently selected from the group consisting of F, Cl, Br, —C$_{1-4}$ alkyl, —CF$_3$, —CHF$_2$, —CH$_2$F, —C$_{1-4}$ alkoxy, —C$_{1-4}$ alkylthio, phenoxy, phenyl, and benzyloxy; or a radical selected from the group consisting of phenyl, naphthyl, (1,3)benzodioxolyl, (1,4)benzodioxanyl, thiophenyl, furanyl, pyrrolyl, pyrazolyl, pyrazynyl, pyranyl, triazolyl, pyridynyl, imidazolyl, indolyl, isoindolyl, benzo[b]furanyl, benzo[b]thiophenyl, thiazolyl, oxazolyl, isoxazolyl, pyridazynyl, pyrazynyl, pyrimidynyl, indazolyl, quinazolinyl, quinolynyl, and isoquinolynyl, which radical can in each case be bonded via a linear or branched $C_{1-5}$ alkylene group or $C_{2-5}$ alkenylene group, optionally substituted by a phenyl radical and optionally comprising a carbonyl group (C=O) as link and/or can be substituted by 1, 2, 3, 4, or 5 substituents independently selected from the group consisting of F, Cl, Br, —CN, —CF$_3$, —CHF$_2$, —CH$_2$F, hydroxy, —C$_{1-6}$ alkoxy, —O—CF$_3$, —S—CF$_3$, —SH, —C$_{1-6}$ alkylthio, —C$_1$-G alkyl, —NH$_2$, —NH—(C$_{1-3}$ alkyl), —N(C$_{1-3}$ alkyl)-(C$_{1-3}$ alkyl), —NH-phenyl, —N(C$_{1-3}$ alkyl)-phenyl, N(phenyl)$_2$, phenoxy, benzyloxy, phenyl, benzyl, and morpholynyl, and in each case the cyclic moiety of the radicals phenoxy, benzyloxy, phenyl, and benzyl can be substituted by 1, 2, 3, 4, or 5 substituents independently selected from the group consisting of F, Cl, Br, hydroxy, —CF$_3$, —SF$_5$, —CN, —NO$_2$, —C$_{1-6}$ alkoxy, —O—CF$_3$, —S—CF$_3$, phenyl, and benzyloxy;

preferably $R^8$ represents an alkyl radical selected from the group consisting of methyl, ethyl, n-propyl, isopropyl, n-butyl, tert-butyl, and n-pentyl, and the alkyl radical can in each case be substituted by 1 or 2 substituents independently selected from the group consisting of NH$_2$, —NH—CH$_3$, —NH—C$_2$H$_5$, —N—(CH$_3$)$_2$, —N(C$_2$H$_5$)$_2$, —N(CH$_3$) (C$_2$H$_5$), —NH-phenyl, —N(CH$_3$)-phenyl, —N(C$_2$H$_5$)-phenyl, and —N(phenyl)$_2$; or a cycloaliphatic radical selected from the group consisting of pyrrolidynyl and piperidynyl, which cycloaliphatic radical can be bonded via a —(C=O) group or a —(CH$_2$)—(C=O) group and/or can be substituted by 1, 2, 3, 4, or 5 substituents independently selected from the group consisting of F, Cl, Br, —CN, —CF$_3$, —CHF$_2$, —CH$_2$F, hydroxy, —O—CH$_3$, —O—C$_2$H$_5$, —O—C$_3$H$_7$, —NH$_2$, —NH—CH$_3$, —NH—C$_2$H$_5$, —N—(CH$_3$)$_2$, —N(C$_2$H$_5$)$_2$, —N(CH$_3$)(C$_2$H$_5$), —NH-phenyl, —N(CH$_3$)-phenyl, —N(C$_2$H$_5$)-phenyl, —N(phenyl)$_2$, —SH, —S—CH$_3$, —S—C$_2$H$_5$, —S—C$_3$H$_7$, —S—C(CH$_3$)$_3$, methyl, ethyl, n-propyl, isopropyl, n-butyl, sec-butyl, and tert-butyl; or a radical selected from the group consisting of phenyl, 1-naphthyl, 2-naphthyl, 2-furanyl, 3-furanyl, 2-thiophenyl, 3-thiophenyl, 1-pyridynyl, 2-pyridynyl, 3-pyridynyl, benzo[b]furanyl, (1,3)benzodioxolyl, and (1,4)benzodioxanyl, which radical can be bonded via a —(C=O) group, —(CH$_2$) group, —(CH$_2$)$_2$ group, —CH(CH$_3$) group, —(CH=CH) group, —(CH$_2$)—(C=O) group, —(CH$_2$)—(CH=CH) group, or —(CH$_2$)$_3$ group and/or can be substituted by 1, 2, 3, 4, or 5 substituents independently selected from the group consisting of F, Cl, Br, —CN, —CF$_3$, —CHF$_2$, —CH$_2$F, hydroxy, —O—CH$_3$, —O—C$_2$H$_5$, —O—C$_3$H$_7$, —O—CF$_3$, —S—CF$_3$, —SH, —S—CH$_3$, —S—C$_2$H$_5$, —S—C$_3$H$_7$, —S—C(CH$_3$)$_3$, methyl, ethyl, n-propyl, isopropyl, n-butyl, sec-butyl, tert-butyl, —NH$_2$, —NH—CH$_3$, —NH—C$_2$H$_5$, —N—(CH$_3$)$_2$, —N(C$_2$H$_5$)$_2$, —N(CH$_3$)—(C$_2$H$_5$), —NH-phenyl, —N(CH$_3$)-phenyl, —N(C$_2$H$_5$)-phenyl, —N(phenyl)$_2$, phenoxy, benzyloxy, phenyl, benzyl, and morpholynyl;

$R^9$ represents an alkyl radical selected from the group consisting of methyl, ethyl, n-propyl, isopropyl, n-butyl, sec-butyl, isobutyl, tert-butyl, n-pentyl, sec-pentyl, (1,1)-dimethylpropyl, and n-hexyl, and $R^{10}$ represents a cycloaliphatic radical selected from the group consisting of pyrrolidynyl and piperidynyl, which cycloaliphatic radical can be bonded via a —(CH$_2$) group, —(CH$_2$)$_2$ group, —CH(CH$_3$) group, or —(CH$_2$)$_3$ group and/or can be substituted by 1, 2, 3, 4, or 5 substituents independently selected from the group consisting of F, Cl, Br, —CN, —CF$_3$, —CHF$_2$, —CH$_2$F, hydroxy, —O—CH$_3$, —O—C$_2$H$_5$, —O—C$_3$H$_7$, —NH$_2$, —NH—CH$_3$, —NH—C$_2$H$_5$, —N—(CH$_3$)$_2$, —N(C$_2$H$_5$)$_2$, —N(CH$_3$)—(C$_2$H$_5$), —NH-phenyl, —N(CH$_3$)phenyl, —N(C$_2$H$_5$)phenyl, —N(phenyl)$_2$, —SH, —S—CH$_3$, —S—C$_2$H$_5$, —S—C$_3$H$_7$, —S—C(CH$_3$)$_3$, methyl, ethyl, n-propyl, isopropyl, n-butyl, sec-butyl, and tert-butyl; or a radical selected from the group consisting of phenyl, 1-naphthyl, and 2-naphthyl, which radical can be bonded via a —(CH$_2$) group, —[(CH)phenyl] group, —(CH$_2$)$_2$ group, and —(CH$_2$)$_3$ group and/or can be substituted by 1, 2, 3, 4, or 5 substituents independently selected from the group consisting of F, Cl, Br, —CN, —CF$_3$, —CHF$_2$, —CH$_2$F, hydroxy, —O—CH$_3$, —O—C$_2$H$_5$, —O—C$_3$H$_7$, —O—CF$_3$, —S—CF$_3$, —SH, —S—CH$_3$, —S—C$_2$H$_5$, —S—C$_3$H$_7$, —S—C(CH$_3$)$_3$, methyl, ethyl, n-propyl, isopropyl, n-butyl, sec-butyl, tert-butyl, —NH$_2$, —NH—CH$_3$, —NH—C$_2$H$_5$, —N—(CH$_3$)$_2$, —N(C$_2$H$_5$)$_2$, —N(CH$_3$)(C$_2$H$_5$), —NH-phenyl, —N(CH$_3$)-phenyl, —N(C$_2$H$_5$)-phenyl, —N(phenyl)$_2$, phenoxy, benzyloxy, phenyl, benzyl, and morpholynyl;

more preferably $R^8$ represents a radical selected from the group consisting of methyl, ethyl, n-propyl, isopropyl, and —(CH$_2$)—(CH$_2$)—N(CH$_3$)$_2$, or a pyrrolidynyl radical which is bonded via a —(CH$_2$)—(C=O) group, or a radical selected from the group consisting of phenyl, 1-naphthyl, 2-naphthyl, 2-thiophenyl, 3-thiophenyl, 1-pyridynyl, 2-pyridynyl, 3-pyridynyl, benzo[b]furanyl, (1,3)benzodioxolyl, and (1,4)benzodioxanyl, which radical can be bonded via a —(C=O) group, —(CH$_2$) group, —(CH$_2$)$_2$ group, —CH(CH$_3$) group, —(CH=CH) group, —(CH$_2$)—(C=O) group, —(CH$_2$)—(CH=CH) group, or —(CH$_2$)$_3$ group and/or can be substituted by 1, 2, or 3 substituents independently selected from the group consisting of F, Cl, Br, —CN, —CF$_3$, —CHF$_2$, —CH$_2$F, —O—CH$_3$, and —O—C$_2$H$_5$, $R^9$ represents a methyl group or an ethyl group, and
$R^{10}$ represents a pyrrolidynyl radical, which is bonded via a —(CH$_2$) group, or a benzyhydryl radical;

and the remaining radicals $R^1$ to $R^6$ and X each have the meanings specified above, optionally in the form of the pure stereoisomers thereof, particularly the enantiomers or diastereoisomers thereof, the racemates thereof or in the form of mixtures of the stereoisomers, particularly of the enantiomers and/or diastereoisomers, in an arbitrary mixture ratio, or optionally in the form of appropriate salts or in each case in the form of appropriate solvates.

Special preference is given to substituted 4,5,6,7-tetrahydrobenzthiazol-2-ylamine compounds of the general formula I, in which $R^1$ represents an —NR$^3$R$^4$ group or an —NR$^5$R$^6$ group;
$R^2$ represents an alkyl radical selected from the group consisting of n-propyl, isopropyl, n-butyl, sec-butyl, isobutyl, tert-butyl, n-pentyl, sec-pentyl, and (1,1)-dimethylpropyl; or
an alkenyl radical selected from the group consisting of 1-pentenyl, 2-pentenyl and pent-1,3-dienyl; or
a cycloaliphatic radical selected from the group consisting of cyclopentyl, cyclohexyl, and cycloheptyl, which is bonded via a —(CH$_2$) group; or
a radical selected from the group consisting of phenyl, 1-naphthyl, 2-naphthyl, 2-furanyl, 3-furanyl, 2-thiophenyl, or 3-thiophenyl, which radical can be bonded via a —(CH$_2$) group, —(CH$_2$)$_2$ group, —(CH$_2$)—O group, —CH(CH$_3$) group, —(CH=CH) group, or —(CH$_2$)$_3$ group and/or can be substituted by 1, 2, or 3 substituents independently selected from the group consisting of F, Cl, Br, —O—CH$_3$, —O—C$_2$H$_5$, methyl, ethyl, n-propyl, and isopropyl;
$R^3$ represents a hydrogen atom or a methyl group;
$R^4$ represents a radical selected from the group consisting of methyl, ethyl, n-propyl, —(CH$_2$)—N(CH$_3$)$_2$, —(CH$_2$)—(CH$_2$)—N(CH$_3$)$_2$, —(CH$_2$)—(CH$_2$)—(CH$_2$)—N(CH$_3$)$_2$, —(CH$_2$)—(CH$_2$)—N(C$_2$H$_5$)$_2$, —(CH$_2$)—(CH$_2$)—(CH$_2$)—N(C$_2$H$_5$)$_2$, —(CH$_2$)—(CH$_2$)—N(CH$_3$)-(phenyl), and —(CH$_2$)—(CH$_2$)—(CH$_2$)—N(CH$_3$)-(phenyl); or
a radical selected from the group consisting of

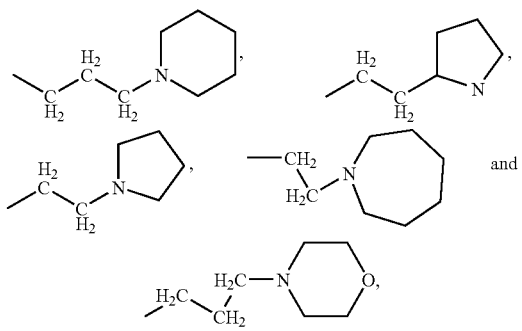

which optionally can be substituted by a methyl group; or
a radical corresponding to the formula

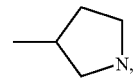

which optionally can be substituted on the nitrogen atom by a substituent selected from the group consisting of —(CH$_2$)benzo[b]furanyl and benzyl, and in each case the cyclic moiety of the radicals —(CH$_2$)benzo[b]furanyl and benzyl can be substituted by 1, 2, or 3 substituents independently selected from the group consisting of F, Cl, Br, —O—CH$_3$, —O—C$_2$H$_5$, —O—C$_3$H$_7$, —S—CH$_3$, —S—C$_2$H$_5$, —S—C$_3$H$_7$, —S—C(CH$_3$)$_3$, methyl, ethyl, n-propyl, isopropyl, n-butyl, phenoxy, and benzyloxy; or
a radical selected from the group consisting of phenyl and benzyl, and the cyclic moiety of the radicals phenyl and benzyl can be substituted by 1, 2, or 3 substituents independently selected from the group consisting of —O—CH$_3$, —O—C$_2$H$_5$, —O—C$_3$H$_7$, —N—(CH$_3$)$_2$, —N(C$_2$H$_5$)$_2$, and morpholynyl;
$R^5$ and $R^6$ together with the nitrogen atom to which they are attached form one of the following radicals

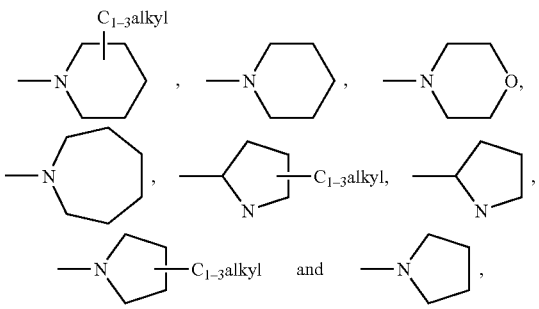

wherein
X represents a methyl group,
$R^8$ represents a radical selected from the group consisting of methyl, ethyl, n-propyl, isopropyl, and —(CH$_2$)—(CH$_2$)—N(CH$_3$)$_2$, or
a pyrrolidynyl radical which is bonded via a —(CH$_2$)—(C=O) group, or
a radical selected from the group consisting of phenyl, 1-naphthyl, 2-naphthyl, 2-thiophenyl, 3-thiophenyl, 1-pyridynyl, 2-pyridynyl, 3-pyridynyl, benzo[b]furanyl, (1,3)benzodioxolyl, and
(1,4)benzodioxanyl, which radical can be bonded via a —(C=O) group, —(CH$_2$) group, —(CH$_2$)$_2$ group, —CH(CH$_3$) group, —(CH=CH) group,
—(CH$_2$)—(C=O) group, —(CH$_2$)—(CH=CH) group, or —(CH$_2$)$_3$ group and/or can be substituted by 1, 2, or 3 substituents independently selected from the group consisting of F, Cl, Br, —CN, —CF$_3$, —CHF$_2$, —CH$_2$F, —O—CH$_3$, and —O—C$_2$H$_5$,
$R^9$ represents a methyl group or an ethyl group; and
$R^{10}$ represents a pyrrolidynyl radical, which is bonded via a —(CH$_2$) group, or a benzyhydryl radical;

in each case optionally in the form of the pure stereoisomers thereof, particularly the enantiomers or diastereoisomers thereof, the racemates thereof or in the form of mixtures of the stereoisomers, particularly of the enantiomers and/or diastereoisomers, in an arbitrary mixture ratio, or optionally in the form of appropriate salts or in each case in the form of appropriate solvates.

Very special preference is given to substituted 4,5,6,7-tetrahydrobenzthiazol-2-ylamine compounds of the general formula I selected from the group consisting of:

2-cyclohexyl-N-{4-[4-(2-dimethylaminoethyl)piperazin-1-carbonyl]-4,5,6,7-tetrahydrobenzthiazol-2-yl)-acetamide,
N-{4-[4-(7-methoxybenzo[1,3]dioxol-5-ylmethyl)piperazin-1-carbonyl]-4,5,6,7-tetrahydrobenzthiazol-2-yl}-2-(2-methoxyphenyl)acetamide,
N-{4-[4-(4-methoxyphenyl)-3-methylpiperazin-1-carbonyl]-4,5,6,7-tetrahydrobenzthiazol-2-yl}benzamide,
furan-2-carboxylic acid{4-[4-(4-acetylphenyl)piperazin-1-carbonyl]-4,5,6,7-tetrahydrobenzthiazol-2-yl}amide,
2-[(Furan-2-carbonyl)amino]-4,5,6,7-tetrahydrobenzthiazol-4-carboxylic acid[1-(2,4,6-trimethoxybenzyl)pyrrolidin-3-yl]amide,
N-[4-(4-Isopropylpiperazin-1-carbonyl)-4,5,6,7-tetrahydrobenzthiazol-2-yl]-2-phenylpropionamide,
3-Furan-2-yl-N-[4-(4-thiophen-3-ylmethylpiperazin-1-carbonyl)-4,5,6,7-tetrahydrobenzthiazol-2-yl]acrylamide,
2-(4-Methoxybenzoylamino)-4,5,6,7-tetrahydrobenzthiazol-4-carboxylic acid[1-(2-chloro-6-fluorobenzyl)pyrrolidin-3-yl]methylamide,
Hexanoic acid[4-(4-pyridin-4-ylpiperazin-1-carbonyl)-4,5,6,7-tetrahydrobenzthiazol-2-yl]amide,
2-(2-Thiophen-2-ylacetylamino)-4,5,6,7-tetrahydrobenzthiazol-4-carboxylic acid(3-morpholin-4-ylpropyl)amide,
2-(2-Phenylpropionylamino)-4,5,6,7-tetrahydrobenzthiazol-4-carboxylic acid[1-(4-phenoxybenzyl)pyrrolidin-3-yl]amide,
2-[(Furan-3-carbonyl)amino]-4,5,6,7-tetrahydrobenzthiazol-4-carboxylic acid(2-azepan-1-ylethyl)amide,
Furan-3-carboxylic acid[4-(4-benzofuran-2-ylmethylpiperazin-1-carbonyl)-4,5,6,7-tetrahydrobenzthiazol-2-yl]amide,
2-Hexanylamino-4,5,6,7-tetrahydrobenzthiazol-4-carboxylic acid[3-(2-methylpiperidin-1-yl)propyl]amide,
2-(2-Phenylpropionylamino)-4,5,6,7-tetrahydrobenzthiazol-4-carboxylic acid(2-dimethylamino-ethyl)amide,
2-Ethoxy-N-[4-(4-phenethylpiperazin-1-carbonyl)-4,5,6,7-tetrahydrobenzthiazol-2-yl]benzamide,
2-(4-Fluorophenoxy)-N-[4-(4-phenylpiperazin-1-carbonyl)-4,5,6,7-tetrahydrobenzthiazol-2-yl]acetamide,
2-(2-Phenylpropionylamino)-4,5,6,7-tetrahydrobenzthiazol-4-carboxylic acid[2-(1-methylpyrrolidin-2-yl)ethyl]amide,
2-(3-Furan-2-ylacryloylamino)-4,5,6,7-tetrahydrobenzthiazol-4-carboxylic acid[3-(2-methylpiperidin-1-yl)propyl]amide,
2-(3,3-Dimethylbutyrylamino)-4,5,6,7-tetrahydrobenzthiazol-4-carboxylic acid(3-dimethylaminopropyl)amide,
N-{4-[4-(4-chlorobenzyl)piperazin-1-carbonyl]-4,5,6,7-tetrahydrobenzthiazol-2-yl}-4-methoxybenzamide,
Naphthalene-2-carboxylic acid[4-(2-pyrrolidin-1-ylmethylpyrrolidin-1-carbonyl)-4,5,6,7-tetrahydrobenzthiazol-2-yl]amide,
N-[4-(4-Benzofuran-2-ylmethylpiperazin-1-carbonyl)-4,5,6,7-tetrahydrobenzthiazol-2-yl]butyramide,
N-{4-[4-(3-Methoxyphenyl)piperazin-1-carbonyl]-4,5,6,7-tetrahydrobenzthiazol-2-yl}benzamide,
2-Butyrylamino-4,5,6,7-tetrahydrobenzthiazol-4-carboxylic acid(1-biphenyl-4-ylmethylpyrrolidin-3-yl)methylamide,
2-(2-Phenoxyacetylamino)-4,5,6,7-tetrahydrobenzthiazol-4-carboxylic acid(2-dimethylamino-ethyl)amide,
2-Ethoxy-N-[4-(2-pyrrolidin-1-ylmethylpyrrolidin-1-carbonyl)-4,5,6,7-tetrahydrobenzthiazol-2-yl]benzamide,
Naphthalene-2-carboxylic acid{4-[4-(2-oxo-2-pyrrolidin-1-ylethyl)piperazin-1-carbonyl]-4,5,6,7-tetrahydrobenzthiazol-2-yl}amide,
2-(2-Phenylpropionylamino)-4,5,6,7-tetrahydrobenzthiazol-4-carboxylic acid[1-(2-bromo-4,5-dimethoxybenzyl)pyrrolidin-3-yl]amide,
Hexanoic acid{4-[4-(2,4,6-trimethoxybenzyl)piperazin-1-carbonyl]-4,5,6,7-tetrahydrobenzthiazol-2-yl}amide,
2-(3,5-Dimethylbenzoylamino)-4,5,6,7-tetrahydrobenzthiazol-4-carboxylic acid[1-(2-tert-butylsulfanylbenzyl)pyrrolidin-3-yl]amide,
2-(2-Phenylpropionylamino)-4,5,6,7-tetrahydrobenzthiazol-4-carboxylic acid[1-(2-benzyloxybenzyl)pyrrolidin-3-yl]methylamide,
2-Hexa-2,4-dienoylamino-4,5,6,7-tetrahydrobenzthiazol-4-carboxylic acid(1-biphenyl-4-ylmethylpyrrolidin-3-yl)methylamide,
2-(3-Phenylpropionylamino)-4,5,6,7-tetrahydrobenzthiazol-4-carboxylic acid(2-diethylamino-ethyl)amide,
2-(2-Thiophen-2-ylacetylamino)-4,5,6,7-tetrahydrobenzthiazol-4-carboxylic acid(2-azepan-1-ylethyl)amide,
2-(2-Thiophen-2-ylacetylamino)-4,5,6,7-tetrahydrobenzthiazol-4-carboxylic acid[1-(2-ethoxybenzyl)pyrrolidin-3-yl]methylamide,
2-Hexanylamino-4,5,6,7-tetrahydrobenzthiazol-4-carboxylic acid(1-benzofuran-2-ylmethylpyrrolidin-3-yl)methylamide,
2-(2-Phenoxyacetylamino)-4,5,6,7-tetrahydrobenzthiazol-4-carboxylic acid[3-(2-methylpiperidin-1-yl)propyl]amide,
2-[(Naphthalene-2-carbonyl)amino]-4,5,6,7-tetrahydrobenzthiazol-4-carboxylic acid(2-pyrrolidin-1-ylethyl)amide,
2-[2-(3,5-Difluorophenyl)acetylamino]-4,5,6,7-tetrahydrobenzthiazol-4-carboxylic acid[1-(2-ethoxybenzyl)pyrrolidin-3-yl]methylamide,
2-[(Naphthalene-2-carbonyl)amino]-4,5,6,7-tetrahydrobenzthiazol-4-carboxylic acid 4-dimethylamino-benzylamide,
2-[2-(4-Fluorophenoxy)acetylamino]-4,5,6,7-tetrahydrobenzthiazol-4-carboxylic acid[2-(1-methylpyrrolidin-2-yl)ethyl]amide,
Furan-2-carboxylic acid{4-[4-(2-cyano-phenyl)piperazin-1-carbonyl]-4,5,6,7-tetrahydrobenzthiazol-2-yl}amide,
2-(3-Phenylpropionylamino)-4,5,6,7-tetrahydrobenzthiazol-4-carboxylic acid(1-benzofuran-2-ylmethylpyrrolidin-3-yl)methylamide,
2-Hexa-2,4-dienoylamino-4,5,6,7-tetrahydrobenzthiazol-4-carboxylic acid[1-(2,6-dichlorobenzyl)pyrrolidin-3-yl]methylamide,
2-[(Furan-2-carbonyl)amino]-4,5,6,7-tetrahydrobenzthiazol-4-carboxylic acid[1-(5-bromo-2-ethoxybenzyl)pyrrolidin-3-yl]amide,
2-(2-Phenoxyacetylamino)-4,5,6,7-tetrahydrobenzthiazol-4-carboxylic acid[1-(2-ethoxybenzyl)pyrrolidin-3-yl]methylamide,
Hexanoic acid{4-[4-(2-fluorophenyl)piperazin-1-carbonyl]-4,5,6,7-tetrahydrobenzthiazol-2-yl}amide,
Naphthalene-2-carboxylic acid{4-[4-(2-fluorobenzyl)piperazin-1-carbonyl]-4,5,6,7-tetrahydrobenzthiazol-2-yl}amide,
2-(2-Phenoxyacetylamino)-4,5,6,7-tetrahydrobenzthiazol-4-carboxylic acid methyl-[1-(2-trifluoromethylbenzyl)pyrrolidin-3-yl]amide, 2-(3-Phenylpropionylamino)-4,5,6,7-tetrahydrobenzthiazol-4-carboxylic acid(1-biphenyl-4-ylmethylpyrrolidin-3-yl)methylamide, 2-[2-(2-Methoxyphenyl)acetylamino]-4,5,6,7-tetrahydrobenzthiazol-4-carboxylic acid(1-benzofuran-2-ylmethylpyrrolidin-3-yl)methylamide, 2-(3,5-Difluorophenyl)-N-[4-(2-pyrrolidin-1-ylmethylpyrrolidin-1-carbonyl)-4,5,6,7-tetrahydrobenzthiazol-2-yl]acetamide, 2-[(Furan-2-carbonyl)amino]-4,5,6,7-tetrahydrobenzthiazol-4-carboxylic acid 4-dimethylamino-benzylamide, Hexanoic acid{4-[4-(3-fluoro-4-methoxybenzyl)piperazin-1-carbonyl]-4,5,6,7-tetrahydrobenzthiazol-2-yl}amide, N-{4-[4-(4-Methoxyphenyl)-3-methylpiperazin-1-carbonyl]-4,5,6,7-tetrahydrobenzthiazol-2-yl}-2-phenylpropionamide, 2-Hexa-2,4-dienoylamino-4,5,6,7-tetrahydrobenzthiazol-4-carboxylic acid [1-(2-chloro-6-fluorobenzyl)pyrrolidin-3-yl]methylamide, 2-[2-(3,5-Difluorophenyl)acetylamino]-4,5,6,7-tetrahydrobenzthiazol-4-carboxylic acid[1-(2,6-dichlorobenzyl)pyrrolidin-3-yl]methylamide, 2-[2-(4-fluorophenoxy)acetylamino]-4,5,6,7-tetrahydrobenzthiazol-4-carboxylic acid [1-(2-ethoxybenzyl)pyrrolidin-3-yl]methylamide, Furan-3-carboxylic acid[4-(4-pyridin-2-ylpiperazin-1-carbonyl)-4,5,6,7-tetrahydrobenzthiazol-2-yl]amide, Hexanoic acid[4-(4-benzofuran-2-ylmethylpiperazin-1-carbonyl)-4,5,6,7-tetrahydrobenzthiazol-2-yl]amide, 2-Phenoxy-N-{4-[4-(1-phenylethyl)piperazin-1-carbonyl]-4,5,6,7-tetrahydrobenzthiazol-2-yl}acetamide, 2-(2-Cyclohexylacetylamino)-4,5,6,7-tetrahydrobenzthiazol-4-carboxylic acid[1-(2,6-dichlorobenzyl)pyrrolidin-3-yl]methylamide, 2-(2-Cyclohexylacetylamino)-4,5,6,7-tetrahydrobenzthiazol-4-carboxylic acid[3-(methylphenyl-amino)propyl]amide, 2-(2-Ethoxybenzoylamino)-4,5,6,7-tetrahydrobenzthiazol-4-carboxylic acid[3-(methylphenylamino)propyl]amide, 3-Phenyl-N-{4-[4-(5-trifluoromethylpyridin-2-yl)piperazin-1-carbonyl]-4,5,6,7-tetrahydrobenzthiazol-2-yl}propionamide, Furan-3-carboxylic acid[4-(4-phenethylpiperazin-1-carbonyl)-4,5,6,7-tetrahydrobenzthiazol-2-yl]amide, 3-Phenyl-N-{4-[4-(3-trifluoromethylphenyl)piperazin-1-carbonyl]-4,5,6,7-tetrahydrobenzthiazol-2-yl}propionamide, 2-(3,3-Dimethylbutyrylamino)-4,5,6,7-tetrahydrobenzthiazol-4-carboxylic acid[1-(2-benzyloxybenzyl)pyrrolidin-3-yl]amide, 2-(3,5-Difluorophenyl)-N-{4-[4-(3-trifluoromethylphenyl)piperazin-1-carbonyl]-4,5,6,7-tetrahydrobenzthiazol-2-yl}acetamide, 2-Ethoxy-N-{4-[4-(1-phenylethyl)piperazin-1-carbonyl]-4,5,6,7-tetrahydrobenzthiazol-2-yl}benzamide, 3-Furan-2-yl-N-{4-[4-(3-trifluoromethylphenyl)piperazin-1-carbonyl]-4,5,6,7-tetrahydrobenzthiazol-2-yl}acrylamide, N-{4-[4-(2-Cyano-phenyl)piperazin-1-carbonyl]-4,5,6,7-tetrahydrobenzthiazol-2-yl}-3-phenylpropionamide, 2-(2-Cyclohexylacetylamino)-4,5,6,7-tetrahydrobenzthiazol-4-carboxylic acid[1-(2-chloro-6-fluorobenzyl)pyrrolidin-3-yl]methylamide, N-{4-[4-(2-Methoxynaphthalene-1-ylmethyl)piperazin-1-carbonyl]-4,5,6,7-tetrahydrobenzthiazol-2-yl}-3,3-dimethylbutyramid, 2-(3,3-Dimethylbutyrylamino)-4,5,6,7-tetrahydrobenzthiazol-4-carboxylic acid (2,5-diethoxy-4-morpholin-4-ylphenyl)amide, N-{4-[4-(2-Chlorophenyl)piperazin-1-carbonyl]-4,5,6,7-tetrahydrobenzthiazol-2-yl}-2-(4-fluorophenyl)acetamide, N-[4-(4-Benzylpiperazin-1-carbonyl)-4,5,6,7-tetrahydrobenzthiazol-2-yl]-3,3-dimethylbutyramide, N-[4-(4-Benzhydrylpiperazin-1-carbonyl)-4,5,6,7-tetrahydrobenzthiazol-2-yl]-2-(3,5-difluorophenyl)acetamide, N-[4-(4-Benzhydrylpiperazin-1-carbonyl)-4,5,6,7-tetrahydrobenzthiazol-2-yl]-2-thiophen-2-ylacetamide, N-{4-[4-(2-Chlorophenyl)piperazin-1-carbonyl]-4,5,6,7-tetrahydrobenzthiazol-2-yl}-2-ethoxybenzamide, 3,3-Dimethyl-N-{4-[4-(5-trifluoromethylpyridin-2-yl)piperazin-1-carbonyl]-4,5,6,7-tetrahydrobenzthiazol-2-yl]-butyramide, 3,3-Dimethyl-N-{4-[4-(3-phenylallyl)piperazin-1-carbonyl]-4,5,6,7-tetrahydrobenzthiazol-2-yl}butyramide N-[4-(4-Benzhydrylpiperazin-1-carbonyl)-4,5,6,7-tetrahydrobenzthiazol-2-yl]-2-cyclohexylacetamide, and Furan-2-carboxylic acid[4-(4-phenylpiperazin-1-carbonyl)-4,5,6,7-tetrahydrobenzthiazol-2-yl]amide;

optionally in the form of their pure stereoisomers, particularly enantiomers or diastereoisomers, of their racemates or in the form of mixtures of the stereoisomers, particularly the enantiomers and/or diastereoisomers, in an arbitrary mixture ratio, or optionally in the form of appropriate salts or optionally in the form of appropriate solvates, in each case.

The present invention also relates to a process for the production of the substituted 4,5,6,7-tetrahydrobenzthiazol-2-ylamine compounds of the invention of the above general formula I, according to which at least one compound of formula II

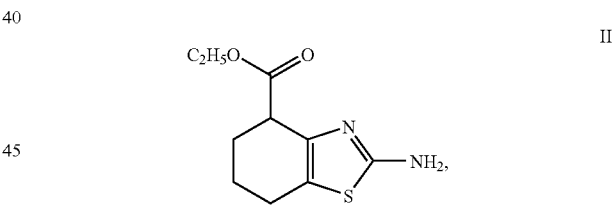

optionally in the form of a salt, is converted, by reaction with at least one acylation agent of the general formula III

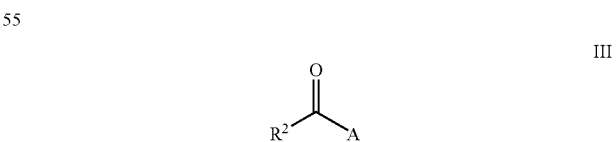

in which $R^2$ has the meanings specified above, and

A represents a group capable of dissociation from the acyl group $R^2$—(C=O)—, preferably —OH, —Cl, or —O—(C=O)—$R^2$, to a compound of the general formula IV,

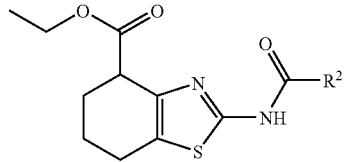

which is optionally purified by conventional methods and/or is optionally isolated, and is optionally converted, by decomposition of the ethyl ester, to a compound of the general formula V

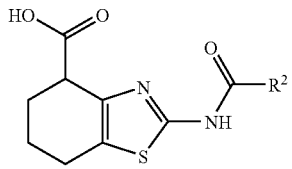

which is optionally purified by conventional methods and/or is optionally isolated, and at least one compound of the general formula IV and/or at least one compound of the general formula V by reaction with at least one compound of the general formula $R^1$—H, in which $R^1$ has the meanings defined above, is converted to a compound of the above general formula I of the invention, which compound is optionally purified by conventional methods and/or is optionally isolated.

The synthesis of the compound of formula II defined above, optionally in the form of an appropriate salt, can be carried out by conventional methods known to the person skilled in the art, for example, by reaction of ethyl 2-oxo-cyclohexanecarboxylate with halogen, preferably bromine or chlorine, under conventional conditions known to the person skilled in the art to produce a corresponding substituted ethyl 3-halo-2-oxocyclohexanecarboxylate. Preferably, the conversion is carried out in a suitable solvent such as chloroform at a temperature of $\leq 30°$ C., optionally under a blanket of inert gas such as nitrogen.

The resulting ethyl 3-halo-2-oxocyclohexanecarboxylate, and preferably ethyl 3-bromo- or 3-chloro-2-oxocyclohexanecarboxylate, can then be caused to react with thiourea by conventional methods known to the person skilled in the art to produce ethyl 2-amino-4,5,6,7-tetrahydrobenzthiazole-4-carboxyate of the general formula II, optionally in the form of a salt, preferably the hydrobromide or hydrochloride. Preferably, the conversion is carried out in a suitable solvent such as ethanol at a temperature $\leq 30°$ C. optionally under a blanket of inert gas such as nitrogen.

The reaction of ethyl 2-amino-4,5,6,7-tetrahydrobenzthiazol-4-carboxylate of the general formula II, or of an appropriate salt, with an acylation agent of the general formula III can be carried out under the usual conditions known to the person skilled in the art.

Preferably, ethyl 2-amino-4,5,6,7-tetrahydrobenzthiazole-4-carboxyate can be converted by acylation with an appropriate carboxylic acid in the presence of a dehydrating agent such as sodium sulfate or magnesium sulfate or phosphorus oxide or in the presence of coupling agents such as 1,1-carbonyldiimidazole or dicyclohexylcarbodiimide to the corresponding compound of general formula IV.

It is likewise preferred to carry out the acylation of ethyl 2-amino-4,5,6,7-tetrahydrobenzthiazol-4-carboxylate with an appropriate carboxylic chloride or an appropriate carboxylic anhydride preferably in the presence of at least one base. Suitable bases are conventional inorganic bases and/or organic bases such as diisopropylethylamine, triethylamine, or diethylamine. The acylation with an appropriate carboxylic chloride is preferably carried out in a suitable solvent such as dichloromethane at a temperature of $\leq 30°$ C.

The ethyl 2-[(acyl)amino]-4,5,6,7-tetrahydrobenzthiazole-4-carboxylate of the general formula IV can be caused to react with appropriately substituted primary or secondary amines of the general formula $R^1$—H, in which $R^1$ has the aforementioned meaning, with amidation, under conventional conditions known to the person skilled in the art to directly produce the correspondingly substituted 4,5,6,7-tetrahydrobenzthiazol-2-ylamine compounds of the general formula I of the invention.

Alternatively—and this is the preferred variant of the process of the invention—the appropriately substituted ethyl 2-[(acyl)amino]-4,5,6,7-tetrahydrobenzthiazole-4-carboxylate is first subjected to ester cleavage under the usual conditions known to the person skilled in the art. Preferably, ester cleavage can be carried out in the presence of an aqueous inorganic base such as sodium hydroxide solution (NaOH), potassium hydroxide solution (KOH) or lithium hydroxide solution (LiOH) at a temperature of $\leq 30°$ C. optionally under a blanket of inert gas to give the corresponding 2-[(acyl)amino]-4,5,6,7-tetrahydrobenzthiazol-4-carboxylic acid compound of the general formula V.

The resulting 2-[(acyl)amino]-4,5,6,7-tetrahydrobenzthiazol-4-carboxylic acid compound of the general formula V can then be caused to react, under the usual conditions known to the person skilled in the art, for example, in the presence of a dehydrating agent such as sodium sulfate or magnesium sulfate or phosphorus oxide or in the presence of coupling agents such as 1,1-carbonyldiimidazole or dicyclohexylcarbodiimide, with appropriately substituted primary or secondary amines of the general formula $R^1$—H in which $R^1$ has the meanings specified above, with amidation, to produce the substituted 4,5,6,7-tetrahydrobenzthiazol-2-ylamine compound of the general formula I of the invention. Preferably, the reaction is carried out in a suitable solvent such as dichloromethane at a temperature of $\leq 30°$ C.

The educts, reagents, and solvents involved in the aforementioned reactions are all commercially available or can be produced by conventional methods known to the person skilled in the art.

The respective intermediate products of the reactions described above and the substituted 4,5,6,7-tetrahydrobenzthiazol-2-ylamine compounds of the invention of the above general formula I themselves can—if necessary or desired—be purified and/or isolated in each case by conventional methods familiar to the person skilled in the art, for example, by chromatographic processes, recrystallization, extraction, or washing, or by combinations of at least two of these methods.

If the substituted 4,5,6,7-tetrahydrobenzthiazol-2-ylamine compounds of the invention of the above general formula I are obtained, following the production thereof, in the form of a mixture of the stereoisomers thereof, for example, in the form of the racemates thereof or other mixtures of the various enantiomers and/or diastereoisomers thereof, these products can be separated and optionally isolated by conventional methods known to the person skilled in the art. For example, mention may be made of chromatographic separation processes, particularly liquid chromatographic process under standard pressure or under elevated pressure, preferably MPLC processes and HPLC processes, and also processes involving fractional crystallization. This can, in particular, involve the separation of individual enantiomers, eg, diastereoisomeric salts formed by means of HPLC in the chiral phase or by means of crystallization with chiral acids, for example (+)-tartaric acid, (−)-tartaric acid, or (+)-10-camphorsulfonic acid.

The substituted 4,5,6,7-tetrahydrobenzthiazol-2-ylamine compounds of the invention of the above general formulas I and optionally, in each case, corresponding stereoisomers can optionally also be produced by conventional methods known to the person skilled in the art in the form of the salts thereof, preferably the physiologically acceptable salts thereof, and the pharmaceutical composition of the invention can comprise one or more physiologically acceptable salts of one or more of these compounds.

The physiologically acceptable salts of the substituted 4,5,6,7-tetrahydrobenzthiazol-2-ylamine compounds of the invention of the above general formula I can be obtained, for example, by reaction with one or more inorganic or organic acids, preferably selected from the group consisting of perchloric acid, hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, saccharinic acid, cyclohexanesulfamidic acid, aspartame, monomethylsebacic acid, 5-oxoproline, hexane-1-sulfonic acid, nicotinic acid, 2-aminobenzoic acid, 3-aminobenzoic acid, 4-aminobenzoic acid, 2,4,6-trimethylbenzoic acid, alpha lipoic acid, acetylglycine, hippuric acid, phosphoric acid, maleic acid, malonic acid, and aspartic acid.

The substituted 4,5,6,7-tetrahydrobenzthiazol-2-ylamine compounds of the invention of the above general formula I and also optionally corresponding stereoisomers and their physiologically acceptable salts can optionally be obtained by conventional methods known to the person skilled in the art in the form of their solvates, in particular their hydrates.

It has now been found, surprisingly, that these substituted 4,5,6,7-tetrahydrobenzthiazol-2-ylamine compounds of the invention exhibit an affinity to 5-HT and noradrenaline receptors and lead to inhibition of the noradrenaline uptake and also to inhibition of the 5-hydroxytryptamine (5-HT) uptake.

The substituted 4,5,6,7-tetrahydrobenzthiazol-2-ylamine compounds of the invention of the above general formula I and optionally corresponding stereoisomers and also their appropriate salts and solvates are toxicologically safe and are therefore suitable for use as pharmaceutically active substances in pharmaceutical compositions.

Thus another object of the present invention is the provision of a pharmaceutical composition containing at least one substituted 4,5,6,7-tetrahydrobenzthiazol-2-ylamine compound of the general formula I, optionally in the form of the pure stereoisomer thereof, particularly the enantiomer or diastereoisomer, or the racemate thereof or in the form of mixtures of the stereoisomers, particularly of the enantiomers and/or diastereoisomers, in an arbitrary mixture ratio, or optionally in the form of an appropriate salt or in the form of an appropriate solvate.

Preferably, the pharmaceutical composition of the invention is suitable for regulation of the noradrenaline reuptake (noradrenaline uptake), for regulation of the 5-hydroxytryptophane reuptake (5-HT uptake), for treatment of the abuse of alcohol and/or of drugs and/or of medicines, for the inhibition and/or treatment of addiction to alcohol and/or to drugs and/or to medicines, for the inhibition and/or treatment of inflammations, for the inhibition and/or treatment of depression, for the inhibition and/or treatment of lethargy, for the inhibition and/or treatment of disturbances of food intake preferably selected from the group consisting of bulimia, anorexia, obesity, and cachexia, for the inhibition and/or treatment of catalepsy, for vigilance enhancement, for libido enhancement or for anxiolysis. Furthermore, the compounds of the invention also show a pronounced analgesic action, so that the pharmaceutical compositions of the invention are extremely well suited for the simultaneous treatment of pain and depression.

The present invention also relates to the use of at least one substituted 4,5,6,7-tetrahydrobenzthiazol-2-ylamine compound of the general formula I, optionally in the form of the pure stereoisomer thereof particularly the enantiomers or diastereoisomers of the racemate thereof or in the form of mixtures of the stereoisomers, particularly of the enantiomers and/or diastereoisomers, in an arbitrary mixture ratio, or optionally in the form of an appropriate salt or in each case in the form of an appropriate solvate, for the production of a pharmaceutical composition for regulation of the noradrenaline reuptake (noradrenaline uptake), for regulation of 5-hydroxytryptophane reuptake (5-HT uptake), for treatment of alcohol abuse and/or drug abuse and/or medicine abuse, for the inhibition and/or treatment of alcohol addiction and/or drug addiction and/or medicine addiction, for the inhibition and/or treatment of inflammations, for inhibition and/or treatment of depression, for treatment of pain, for treatment of lethargy, for inhibition and/or treatment of disturbances in food intake selected from the group consisting of bulimia, anorexia, obesity, and cachexia, for inhibition and/or treatment of catalepsy, for vigilance enhancement, for libido enhancement or for anxiolysis. Particular preference is given to the use of at least one substituted 4,5,6,7-tetrahydrobenzthiazol-2-ylamine compound of the general formula I, optionally in the form of the pure stereoisomer thereof particularly enantiomer or diastereoisomer thereof, of the racemate thereof or in the form of mixtures of the stereoisomers, particularly of the enantiomers and/or diastereoisomers, in an arbitrary mixture ratio, or optionally in the form of an appropriate salt or in the form of an appropriate solvate, for the production of a pharmaceutical composition for the simultaneous treatment of pain and depression.

The pharmaceutical composition of the invention can exist as liquid, semisolid or solid pharmaceutical dosage forms, for example, in the form of injection fluids, drops, juices, syrups, sprays, suspensions, tablets, patches, capsules, plasters, suppositories, ointments, creams, lotions, gels, emulsions, aerosols, or in multiparticular form, for example, in the form of pellets or granules, optionally compressed to tablets, filled into capsules or suspended in a liquid, and can be administered as such.

In addition to one or more of the substituted 4,5,6,7-tetrahydrobenzthiazol-2-ylamine compounds of the above general formula I used in the pharmaceutical composition of the invention, optionally in the form of the pure stereoisomer thereof particularly enantiomer or diastereoisomer, or in the form of the racemate thereof or in the form of mixtures of the stereoisomers, particularly of the enantiomers or diastereoisomers, in an arbitrary mixture ratio, or optionally in the form of an appropriate salt or in each case in the form of an appropriate solvate, the pharmaceutical composition of the invention usually contains further physiologically acceptable pharmaceutical adjuvants, which can be preferably selected from the group consisting of support materials, fillers, solvents, diluents, surfactants, dyes, preservative agents, blasting agents, slip agents, lubricants, flavors, and binding agents.

The selection of the physiologically acceptable adjuvants and the amounts thereof to be used depends on whether the pharmaceutical composition is to be administered orally, subcutaneously, parenterally, intravenously, intraperitoneally, intradermally, intramuscularly, intranasally, buccally, rectally, or locally, eg, to infections of the skin, the mucous membranes, or the eyes. Preparations preferably suitable for oral administration are in the form of tablets, dragees, capsules, granules, pellets, drops, juices, and syrups, and for parenteral, topical, and inhalative administration the suitable preparations are solutions, suspensions, readily reconstructable dry preparations, and also spray.

The substituted 4,5,6,7-tetrahydrobenzthiazol-2-ylamine compounds used in the pharmaceutical composition of the invention in dissolved form in a depot or in a plaster, optionally with the addition of agents for promoting skin penetration, are suitable percutane administration forms. Formulations for oral or percutane administration may also be designed to release the respective substituted 4,5,6,7-tetrahydrobenzthiazol-2-ylamine compounds after a time lapse.

The dosage of the respective substituted 4,5,6,7-tetrahydrobenzthiazol-2-ylamine compound to be administered to the patient can vary and is dependant, for example, on the weight or age of the patient and on the method of administration and the indication and the severity of the disorder. The dosage of at least one substituted 4,5,6,7-tetrahydrobenzthiazol-2-ylamine compound is usually from 0.005 to 500 mg/kg and preferably from 0.05 to 50 mg/kg of body weight of the patient.

As follows, the pharmacological methods for determination of the analgesic action and for determination of the inhibition of noradrenaline reuptake or 5-HT reuptake by the substituted 4,5,6,7-tetrahydrobenzthiazol-2-ylamine compounds of the invention are described.

Pharmacological Methods

I. Analgesic Test Using the Writhing Test on Mice

The analysis of analgesic activity is carried out using the phenylquinone-induced writhing assay in mice, modified as described in the article by I. C. Hendershot and J. Forsaith ((1959) in J. Pharmacol. Exp. Ther. 125, 237-240. The relevant description is incorporated herein by reference and is to be regarded as part of the present disclosure.

For the present purpose, male NMRI mice are used having a weight of from 25 to 30 g. Groups of 10 animals per substance dose receive, 10 minutes after an intravenous dose of test substances, an intraperitoneal administration of 0.3 ml/mouse of a 0.02% strength aqueous solution of phenylquinone (phenylbenzoquinone, obtainable from Sigma, Deisenhofen; solution produced with the addition of 5% of ethanol and storage in a water bath at 45° C.). The animals are placed individually in observation cages. Using a push-button counter, the number of pain-induced stretching movements (so-called writhing reactions=straightening of the body accompanied by stretching of the rear extremities) was counted over a period of from 5 to 20 minutes following the administration of phenylquinone. The control is provided by animals receiving only physiological saline. All substances are tested using the standard dosage of 10 mg/kg. Percentage inhibition (% inhibition) of the writhing reaction by a substance is calculated using the following formula:

% Inhibition=100—writhing reactions of the treated animals times 100 divided by writhing reactions of the control animals For some substances, the dose-related drop in writhing reactions compared with co-examined phenylquinone control groups is used to calculate, by means of regressional analysis (evaluation program Martens EDV Service, Eckental), the $ED_{50}$ values showing a 95% confidence interval of the writhing reaction.

II. Method of Determining the Inhibition of Noradrenaline Uptake or 5-HT Uptake

For in vitro studies, synaptosomes of rat brain areas are freshly isolated, as described in the article "The isolation of nerve endings from brain" by E. G. Gray and V. P. Whittaker, J. Anatomy 96, pages 79-88, 1962. The relevant literature reference is enclosed herein by reference and is to be regarded as part of the disclosure.

The tissue (hypothalamus for the determination of the noradrenaline uptake inhibition and marrow and pons for determination of the 5-HT uptake inhibition) is homogenized in ice-cooled 0.32 M sucrose (100 mg of tissue/1 ml) in a glass homogenizer with teflon pestle by carrying out five full up-and-down strokes at 840 rpm.

The homogenate is centrifuged at 4° C. for 10 minutes at 1000 g. Following subsequent centrifugation at 17,000 g for 55 minutes, the synaptosomes (P2 fraction) are obtained, which are then resuspended in 0.32 M glucose (0.5 mL/100 mg of the original weight).

The respective uptake was measured in a 96 well microtiter plate. The volume was 250 μL and the incubation was carried out at room temperature (ca 20-25° C.) under a blanket of oxygen.

The incubation period was 7.5 minutes for [$^3$H]-NA and 5 minutes for [$^3$H]-5-HT. The 96 samples through were then filtered through a Unifilter GF/B® microtiter plate (Packard) and washed with 200 mL of incubated buffer with the aid of a "Brabdel Cell-Harvester MPXRI 96T". The Unifilter GF/B plate was dried at 55° C. over a period of 1 h. The plate was then sealed with a back seal® (Packard) and there were then added 35 μL of scintillant fluid per well (Ultima Gold, Packard). Following sealing with a top seal® (Packard) and following adjustment of the equilibrium (approximately over a period of 5 h), the radioactivity is determined in a 1450 Microbeta® (Wallac).

The following characteristic data are found for the NA transporter:

$NA$ uptake: $Km=0.32\pm0.11$ μM

The amount of protein used in the above determination corresponded to the values known from the literature, such as is described in "Protein measurement with the folin phenol reagent", Lowry et al., J. Biol. Chem., 193, 265-275, 1951.

A detailed description of the method is disclosed in the literature, for example, in M. Ch. Frink, H.-H. Hennis, W. Engelberger, M. Haurand, and B. Wilffert ((1996) Arzneim-.forsch./Drug Res. 46 (III), 11, 1029-1036. The relevant literature references are incorporated herein by reference and are to be regarded as part of the disclosure.

The invention is described below with reference to examples. These explanations are given by way of example only and the general inventive concept is not restricted thereto.

EXAMPLES

General instructions for the production of the substituted 4,5,6,7-tetrahydrobenzthiazol-2-ylamine compounds of the general formula I of the invention:

Step 1

To a solution of ethyl 2-oxocyclohexanecarboxylate (50 g, 0.29 mol) in $CHCl_3$ (150 mL) there was slowly added bromine (47 g, 0.29 mol) at 0° C. under a blanket of nitrogen as inert gas dropwise over a period of 45 minutes and the resultant mixture was stirred for a period of 6 hours at 0° C. and then for 16 hours at room temperature. Air was then passed into the reaction solution over a period of 2 hours. The organic phase was washed with aqueous saturated $NaHCO_3$ solution (2×15 mL) and aqueous saturated NaCl solution (3×20 mL). Following drying of the organic phase over $Na_2SO_4$ and filtration, the solvent was removed. The product ethyl 3-bromo-2-oxocyclohexanecarboxylate was obtained in a yield of 72.6 g (corresponding to 99% of theory).

Step 2

Ethanol (50 mL) was added to ethyl 3-bromo-2-oxocyclohexane-carboxylate (50 g, 0.20 mol) and thiourea (15.3 g, 0.20 mol) and the reaction mixture was stirred for a period of 24 hours at room temperature under a blanket of nitrogen as inert gas. Following the removal of the solvent, ether (100 mL) was added to the residue. Following stirring for a period of 2 hours at room temperature, the suspension was filtered off and the solid matter was dried in vacuo. The product ethyl 2-amino-4,5,6,7-tetrahydrobenzthiazole-4-carboxyate hydrobromide was obtained in a yield of 58.6 g (corresponding to 95% of theory).

Step 3

The respective carboxylic chloride (16.1 mmol) dissolved in $CH_2Cl_2$ (50 mL) was slowly added dropwise to a solution of ethyl 2-amino-4,5,6,7-tetrahydrobenzthiazole-4-carboxyate hydrobromide (5.0 g, 16.3 mmol) in pyridine (50 mL) at 0° C. over a period of 30 min. Following stirring for 1 hour at 0° C. and then overnight at room temperature, there were added $CH_2Cl_2$ (300 mL) and 3M HCl (300 mL). The organic phase was separated and the aqueous phase extracted with $CH_2Cl_2$ (300 mL). The combined organic phases were dried over $Na_2SO_4$. Following filtration and removal of the solvent, there was obtained the respective ethyl 2-[(acyl)amino]-4,5,6,7-tetrahydrobenzthiazole-4-carboxylate.

Step 4

Water (20 mL) and methanol (80 mL) were added to the respective ethyl 2-[(acyl)amino]-4,5,6,7-tetrahydrobenzthiazole-4-carboxylate (16 mmol) and NaOH (163 mmol), and the resultant mixture was stirred at room temperature under a blanket of nitrogen as inert gas until completion of the reaction. Following removal of the methanol, 1M HCl (250 mL) was added, and the resultant mixture was extracted with $CH_2Cl_2$ (3×20 mL). Following drying of the combined organic phases over $Na_2SO_4$ and filtration, there was obtained the respective 2-[(acyl)amino]-4,5,6,7-tetrahydrobenzthiazol-4-carboxylic acid.

Step 5

1,1-Carbonyldiimidazole (CDI, 110 mol) was added to the solution of the respective 2-[(acyl)amino]-4,5,6,7-tetrahydrobenzthiazol-4-carboxylic acid(100 mol) in $CH_2Cl_2$ (2 mL), and the resultant mixture was stirred for a period of 2 hours at room temperature. Following cooling of the suspension to 0° C., the respective amine (100 mol) dissolved in $CH_2Cl_2$ (2 mL) was added. Following stirring for 30 min at 0° C. and overnight at room temperature, water (1 mL) was added. Following filtration, separation of the organic phase, and drying, the solvent was removed and the resulting residue was purified by means of preparative HPLC, and the respective substituted 4,5,6,7-tetrahydrobenzthiazol-2-ylamine compound of the invention was obtained.

Example 24

2-(3,3-Dimethylbutyrylamino)-4,5,6,7-tetrahydrobenzthiazol-4-carboxylic acid(3-dimethylaminopropyl)amide

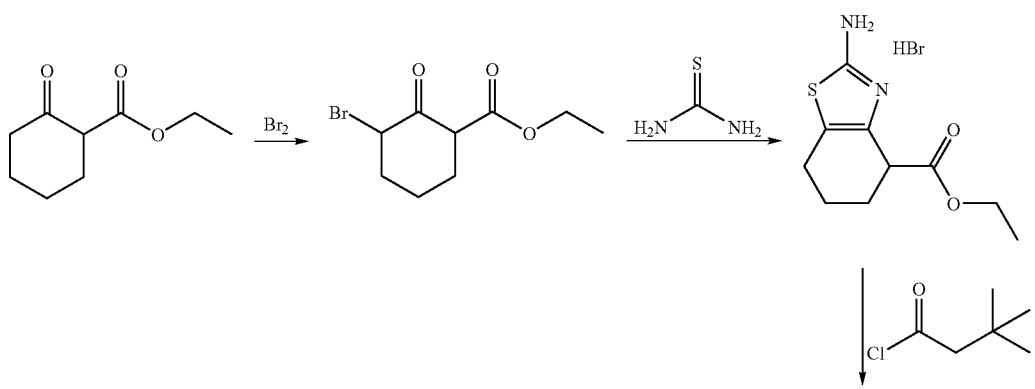

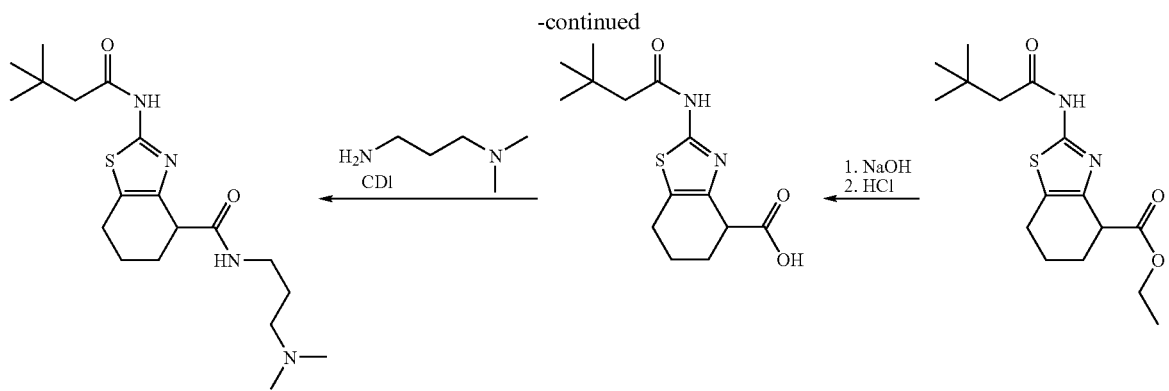

Steps 1 and 2

The synthesis of ethyl 2-amino-4,5,6,7-tetrahydrobenzthiazole-4-carboxyate hydrobromide was carried out according to the general instructions described above.

Step 3

To a solution of ethyl 2-amino-4,5,6,7-tetrahydrobenzthiazole-4-carboxyate hydrobromide (0.92 g, 0.3 mol) in acetonitrile (25 mL) there was added triethylamine (Et$_3$N, 0.41 g, 0.4 mol). Following cooling to 0° C., tert-butylacetyl chloride (0.55 g, 0.4 mol) was slowly added, and the resultant mixture was then stirred overnight at room temperature. Following removal of the solvent and purification by column chromatography, there was obtained ethyl 2-(3,3-dimethylbutyrylamino)-4,5,6,7-tetrahydrobenzthiazol-4-carboxylate in a yield of 185 mg (corresponding to 19% of theory).

Step 4

Water (2 mL) and methanol (8 mL) were added to ethyl 2-(3,3-dimethylbutyrylamino)-4,5,6,7-tetrahydrobenzthiazol-4-carboxylate (185 mg, 0.57 mmol) and NaOH (27 mg, 0.675 mmol), and the resultant mixture was stirred at room temperature under a blanket of nitrogen as inert gas. To complete the reaction, NaOH (200 mg, 5 mmol) was again added, and stirring was continued for a further 24 hours at room temperature. Following removal of MeOH, 2M HCl (10 mL) was added, and the resultant mixture was extracted with CH$_2$Cl$_2$ (3×20 mL). Following drying of the combined organic phases over Na$_2$SO$_4$ and filtration, there was obtained the product 2-(3,3-dimethylbutyrylamino)-4,5,6,7-tetrahydrobenzthiazol-4-carboxylic acid in a yield of 144 mg (corresponding to 85% of theory).

Step 5

1,1-Carbonyldiimidazole (CDI, 87 mg, 0.537 mmol) was added to a solution of 2-(3,3-dimethylbutyrylamino)-4,5,6,7-tetrahydrobenzthiazol-4-carboxylic acid (144 mg, 0.486 mmol) in CH$_2$Cl$_2$ (10 mL), and the resultant mixture was stirred for a period of 2 hours at room temperature. Following cooling of the suspension to 0° C., N,N-dimethyl-1,3-propanediamine (51 mg, 0.50 mmol), dissolved in CH$_2$Cl$_2$ (10 mL), was added dropwise over a period of 10 minutes. Following stirring for 1 hour at 0° C. and overnight at room temperature, a few drops of water were added, and the resultant mixture was extracted with CH$_2$Cl$_2$ (3×10 mL). Following drying of the organic phase over Na$_2$SO$_4$ and filtration, the solvent was removed and the residue was purified via column chromatography. The product 2-(3,3-dimethylbutyrylamino)-4,5,6,7-tetrahydrobenzthiazol-4-carboxylic acid(3-dimethylaminopropyl)amide was obtained in a yield of 125 mg (corresponding to 68% of theory).

Example 89

Furan-2-carboxylic acid[4-(4-phenylpiperazin-1-carbonyl)-4,5,6,7-tetrahydrobenzthiazol-2-yl]amide

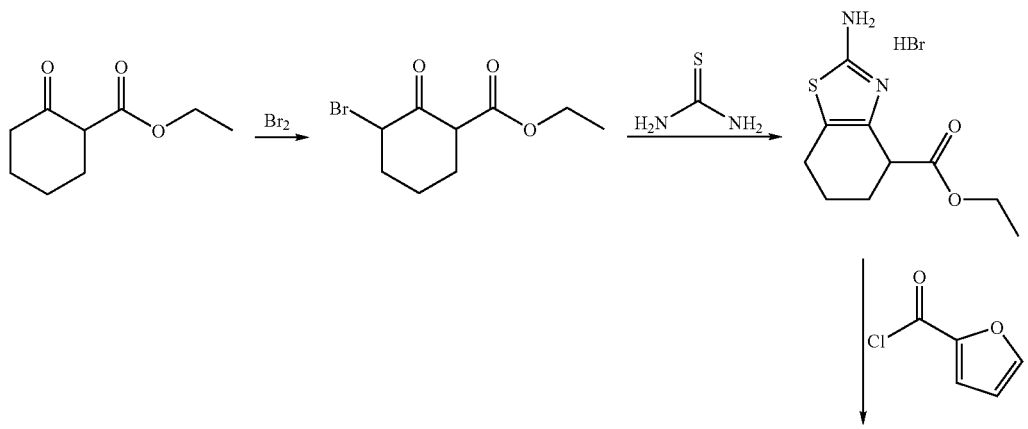

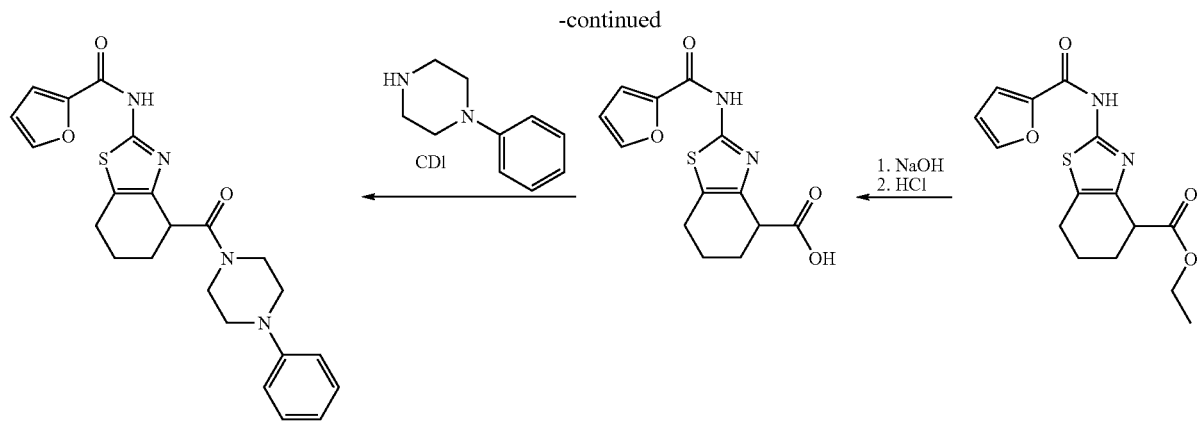

Steps 1 and 2

The synthesis of ethyl 2-amino-4,5,6,7-tetrahydrobenzthiazol-4-carboxylate hydrobromide was carried out according to the general instructions described above.

Step 3

2-Furanoyl chloride (2.1 g, 16.1 mmol) dissolved in CH$_2$Cl$_2$ (50 mL) was slowly added dropwise to a solution of ethyl 2-amino-4,5,6,7-tetrahydrobenzthiazole-4-carboxyate hydrobromide (5.0 g, 16.3 mmol) in pyridine (50 mL) at 0° C. over a period of 30 minutes.

Following stirring for 1 hour at 0° C. and then overnight at room temperature, there were added CH$_2$Cl$_2$ (300 mL) and 3M HCl (300 mL).

The organic phase was separated and the aqueous phase extracted with CH$_2$Cl$_2$ (300 mL).

The combined organic phases were dried over Na$_2$SO$_4$. Following filtration and removal of the solvent, there was obtained the crude product ethyl 2-[(furan-2-carbonyl)amino]-4,5,6,7-tetrahydrobenzthiazol-4-carboxylate in a yield of 5.3 g.

Step 4

Water (20 mL) and methanol (80 mL) were added to ethyl 2-[(furan-2-carbonyl)amino]-4,5,6,7-tetrahydrobenzthiazol-4-carboxylate (5.3 g, 16 mmol) and NaOH (6.5 g, 163 mmol), and the resultant mixture was stirred at room temperature under a blanket of nitrogen as inert gas until completion of the reaction. Following removal of the methanol, 1M HCl (250 mL) was added, and the resultant mixture was extracted with CH$_2$Cl$_2$ (3×20 mL). Following drying of the combined organic phases over Na$_2$SO$_4$ and filtration there was obtained the product 2-[(furan-2-carbonyl)amino]-4,5,6,7-tetrahydrobenzthiazol-4-carboxylic acid starting from ethyl 2-amino-4,5,6,7-tetrahydrobenzthiazole-4-carboxyate hydrobromide in a yield of 3.8 g (corresponding to 81% of the theoretical yield).

Step 5

1,1-Carbonyldiimidazole (CDI, 0.31 g, 1.9 mmol) was added to a solution of 2-[(furan-2-carbonyl)amino]-4,5,6,7-tetrahydrobenzthiazol-4-carboxylic acid (0.5 g, 1.7 mmol) in CH$_2$Cl$_2$ (10 mL), and the resultant mixture was stirred for a period of 2 hours at room temperature. Following cooling of the suspension to 0° C., N-phenylpiperazine (0.28 g, 1.73 mmol), dissolved in CH$_2$Cl$_2$ (10 mL), was added dropwise over a period of 5 minutes. After stirring for 30 min at 0° C. and overnight at room temperature, there were added a few drops of water. Following drying over Na$_2$SO$_4$ and filtration, the solvent was removed and the residue was purified via column chromatography. The product furan-2-carboxylic acid(4-(4-phenylpiperazin-1-carbonyl)-4,5,6,7-tetrahydrobenzthiazol-2-yl]amide was obtained in a yield of 514 mg (corresponding to 69% of the theoretical yield).

ABBREVIATIONS aq. aqueous
DCM dichloromethane
DIPEA diisopropylethylamine
DMF dimethylformamide
EDCl N'-(3-dimethylaminopropyl)-N-ethylcarbodiimide
EtOAc ethyl acetate
EtOH ethanol
sat. saturated
HOAt 1-hydroxy-7-azabenztriazole
MeOH methanol
RT room temperature

Example 67

2-(2-cyclohexylacetylamino)-4,5,6,7-tetrahydrobenzthiazol-4-carboxylic acid[1-(2,6-dichlorobenzyl)pyrrolidin-3-yl]methylamide

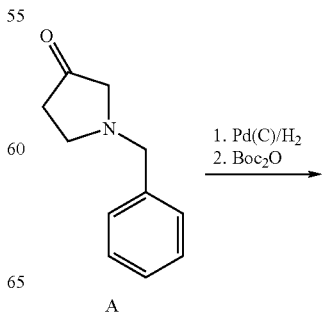

A

-continued

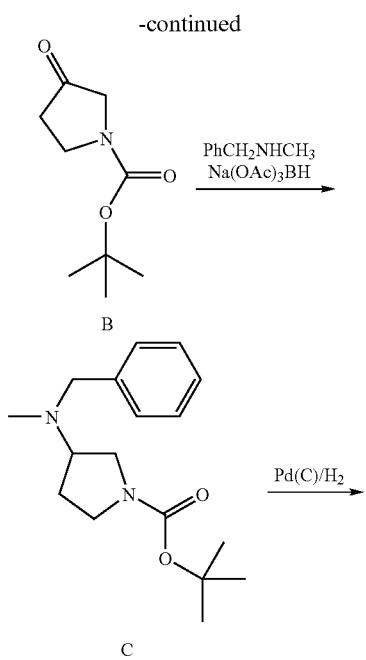

B

C

D

Step 1

A solution of 1-(phenylmethyl)-3-pyrrolidinone (A) (7.18 g, 41 mmol) and di-tert-butylpyrocarbonate (BOC anhydride) (8.94 g, 41 mmol) in dehydrated EtOH (100 mL) was purged with nitrogen. A suspension of palladium on carbon (10%, 4.36 g, 4.1 mmol) in dehydrated EtOH (50 mL) was added. The reaction mixture was exposed to a hydrogen atmosphere in a balloon flask (1 atm) and stirred overnight at RT. Following filtration over Celite and elimination of the solvent in vacuo, the crude product was obtained, which was purified by column chromatography (SiO2, EtOAc/heptane 1:2). There were obtained 5.98 g of the desired product B (corresponding to 79% of theory).

Step 2

The compound B (5.95 g, 32 mmol) was dissolved in DCM (100 mL) in a nitrogen atmosphere, and N-methylbenzylamine (4.28 g, 35 mmol) was added. Sodium triacetoxyboron hydride (10.2 g, 48 mmol) was slowly added at 0° C., and the reaction mixture was stirred over a period of 2 hours at RT. DCM (250 mL) and sat. aq. NaHCO₃ solution (250 mL) were then added. The phases were separated, and the aqueous phase was shaken out with DCM (250 mL). The combined organic phases were dried over Na₂SO₄ and the solvent was removed in vacuo. There were obtained 9.72 g of the desired product C (100% of the theoretical yield).

Step 3

A solution of compound C (9.7 g, 32 mmol) in 150 mL of dehydrated EtOH was purged with nitrogen. A suspension of palladium on carbon (10%, 3.42 g, 3.2 mmol) in dehydrated EtOH (50 mL) was added.

The reaction mixture was exposed to a hydrogen atmosphere in a balloon flask (1 atm) and stirred overnight at RT. Following filtration over Celite and removal of the solvent in vacuo there were obtained 6.74 g (corresponding to 100% of theory) of the desired product D.

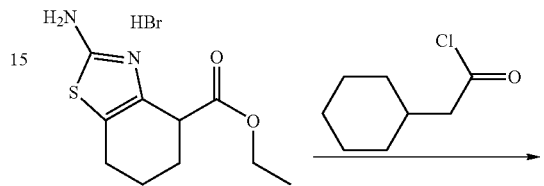

E

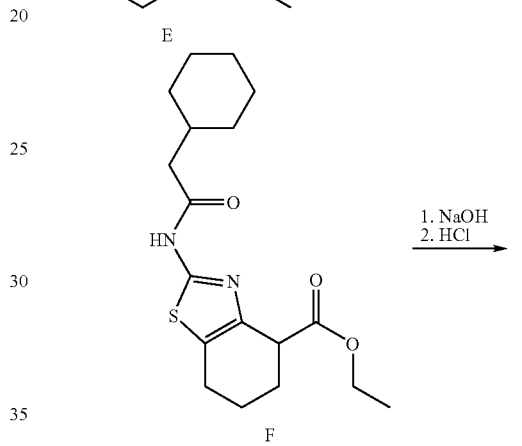

F

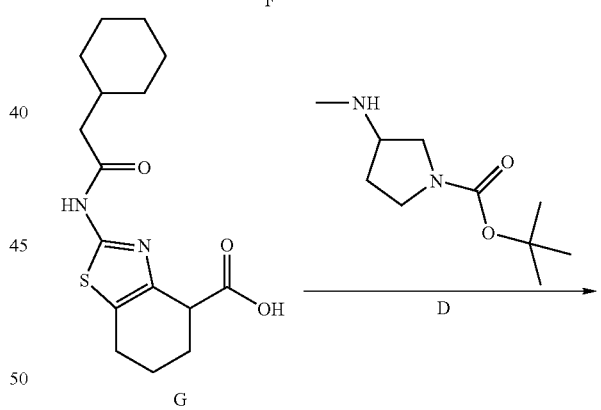

G

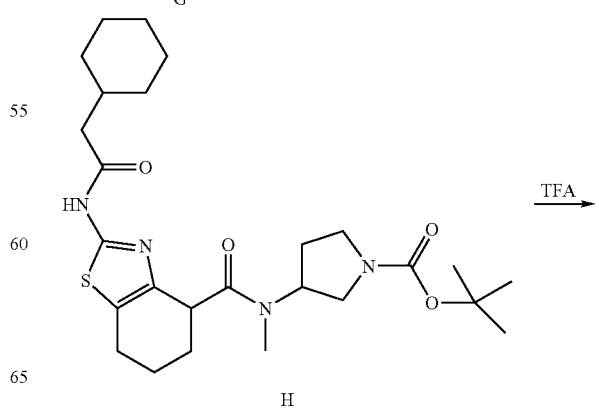

H

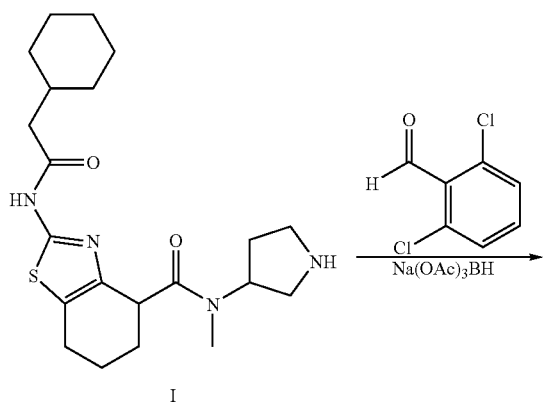

I

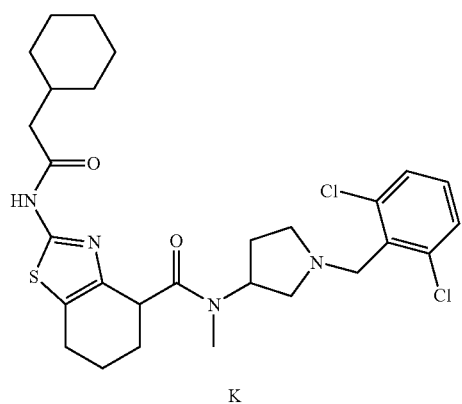

K

Step 1

Oxalyl chloride (3.10 g, 24.42 mmol) was added to a solution of cyclohexylacetic acid (2.31 g, 16.24 mmol) in DCM (10 mL). The reaction mixture was stirred over a period of two hours at RT under a blanket of nitrogen. The solvent was removed in vacuo, toluene (50 mL) was added and the solvent was again removed. The residue was dissolved in DCM (50 mL) and the resultant solution was slowly added dropwise to a solution of ethyl 2-amino-4,5,6,7-tetrahydrobenzthiazole-4-carboxyate hydrobromide (E) (5.0 g, 16.3 mmol) in pyridine (25 mL) under a blanket of nitrogen. The reaction mixture was stirred for one hour at 0° C. and then overnight at RT. DCM (300 mL) and hydrochloric acid solution (3N in water) were added, the phases were separated, and the aqueous phase was shaken out with DCM (300 mL). The combined organic phases were dried over $Na_2SO_4$ and the solvent was removed in vacuo. Following purification by column chromatography (SiO2, EtOAc/heptane 1:2), the residue yielded 4.9 g (86% of theory) of the desired product ethyl 2-(2-cyclohexylacetylamino)-4,5,6,7-tetrahydrobenzthiazol-4-carboxylate (F).

Step 2

Water (20 mL) and MeOH (80 mL) were added to ethyl 2-(2-cyclohexylacetylamino)-4,5,6,7-tetrahydrobenzthiazol-4-carboxylate (F) (4.9 g, 14 mmol) and NaOH (5.6 g, 0.14 mol), and the resultant mixture was stirred at RT under a blanket of nitrogen as inert gas until completion of the reaction. Following removal of MeOH, 2N hydrochloric acid solution in water (250 mL) and DCM (250 mL) was added. The phases were separated, and the aqueous phase was extracted a number of times with DCM. Following drying of the combined organic phases over $Na_2SO_4$ and filtration, there was obtained the product 2-(2-cyclohexylacetylamino)-4,5,6,7-tetrahydrobenzthiazol-4-carboxylic acid (G) in a yield of 3.9 g (corresponding to 87% of theory).

Step 3

The carboxylic acid 2-(2-cyclohexylacetylamino)-4,5,6,7-tetrahydrobenzthiazol-4-carboxylic acid (G) (1201 mg, 3.7 mmol) was added to a solution of the amine D (678 mg, 3.4 mmol) in DCM (15 mL). EDCl (713 mg, 3.7 mmol) and HOAt (69 mg, 0.5 mmol) were added at 0° C. The reaction mixture was stirred for one hour at 0° C. and then overnight at RT. The solvent was removed in vacuo and following purification of the residue by column chromatography (SiO2, DCM/MeOH 97:3→95:5) there were obtained 1.59 g of the desired product H (93% of theory).

Step 4

Trifluoroacetic acid (8.0 mL, 108 mmol) was slowly added to a solution of H (836 mg, 1.66 mmol) in DCM (20 mL) at RT. After an hour the solvent was removed in vacuo. The residue was taken up in toluene three times and in each case the solvent was removed in vacuo. The resulting compound 2-(2-cyclohexylacetylamino)-4,5,6,7-tetrahydrobenzthiazol-4-carboxylic acid (1-pyrrolidin-3-yl)methylamide (I) was used in stage 5 without further workup.

Step 5

Compound 2-(2-cyclohexylacetylamino)-4,5,6,7-tetrahydrobenzthiazol-4-carboxylic acid (1-pyrrolidin-3-yl)methylamide (1) (1.66 mmol) was dissolved in DCM (15 mL) under a blanket of nitrogen. 2,6-Dichlorobenzaldehyde (320 mg, 1.82 mmol) and sodium triacetoxyboron hydride (530 mg, 2.48 mmol) were added. The reaction mixture was stirred overnight at RT under a blanket of nitrogen. Following removal of the solvent in vacuo and purification by column chromatography (SiO₂, DCM/MeOH 95:5), there were obtained 623 mg (1.11 mmol, 67% of theory) of the desired product 2-(2-cyclohexylacetylamino)-4,5,6,7-tetrahydrobenzthiazol-4-carboxylic acid [1-(2,6-dichlorobenzyl)-pyrrolidin-3-yl]methylamide (K).

Example 9

2-[(Furan-2-carbonyl)amino]-4,5,6,7-tetrahydrobenzthiazol-4-carboxylic acid [1-(-2,4,6-trimethoxybenzyl)pyrrolidin-3-yl]amide

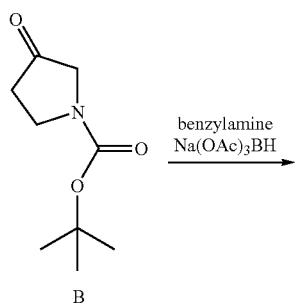

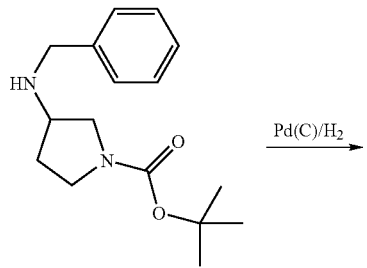

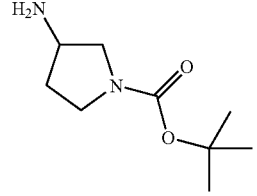

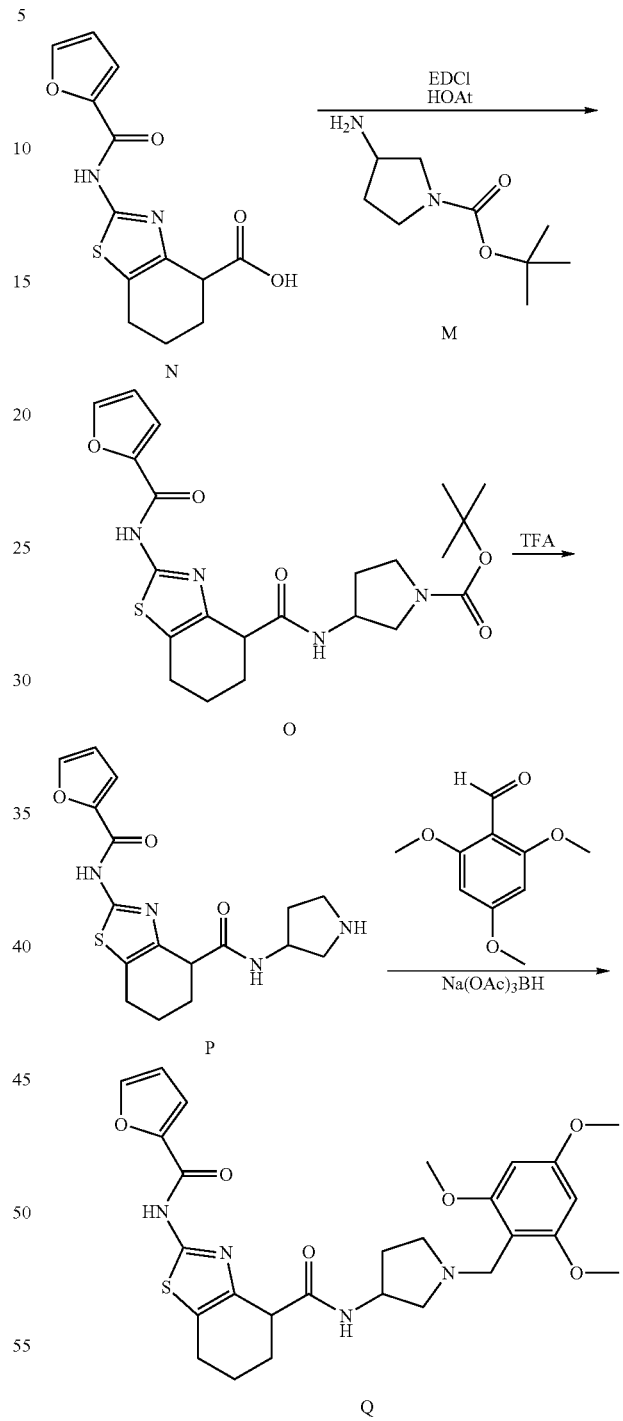

Step 1

The compound B (1.5 g, 8.1 mmol) was dissolved in DCM (25 mL) in a nitrogen atmosphere, and benzylamine (955 mg, 8.91 mmol) was added. Sodium triacetoxyboron hydride (2.58 g, 12.17 mmol) was slowly added at 0° C., and the reaction mixture was stirred over a period of 30 minutes at RT.

DCM (250 mL) and sat. aq. NaHCO$_3$ solution (250 mL) were then added.

The phases were separated, and the aqueous phase was shaken out with DCM (250 mL). The combined organic phases were dried over Na$_2$S$_{O4}$ and the solvent was removed in vacuo. There were obtained 1.8 g (80% of theory) of the desired product L.

Step 2

Nitrogen was passed over a solution of compound L (1.8 g, 6.5 mmol) in 50 mL of dehydrated EtOH over a period of 20 minutes, palladium on carbon (10%, 347 mg, 0.33 mmol) was added and nitrogen was passed over the reaction mixture for a further 10 minutes. The reaction mixture was exposed to a hydrogen atmosphere in a balloon flask (1 atm) and stirred overnight at RT. Nitrogen was passed over the reaction mixture over a period of 30 minutes. Following filtration through Celite, washing of the filter cake with DCM and removal of the solvent in vacuo there were obtained 1.45 g of the desired product M (corresponding to 100% of theory), which were used in the next reaction without further purification.

The compound 2-[(furan-2-carbonyl)amino]-4,5,6,7-tetrahydrobenzthiazol-4-carboxylic acid (N) was produced as described for the synthesis of Example 89, step 4.

Step 1

To a solution of the amine M (727 mg, 3.90 mmol) in dried DCM (5 mL) and dried DMF (5 mL) there was added the carboxylic acid 2-[(furan-2-carbonyl)amino]-4,5,6,7-tetrahydrobenzthiazol-4-carboxylic acid (N) (1.14 g, 3.9 mmol) under a blanket of nitrogen as inert gas.

EDCl (822 mg, 4.29 mmol) and HOAt (53 mg, 0.38 mmol) were added at 0° C. The reaction mixture was stirred over a period of 30 minutes at 0° C. and then overnight at RT. The solvent was removed in vacuo. The residue was taken up in toluene a number of times, and the solvent was removed in vacuo. Following purification of the residue by column chromatography (SiO₂ DCM/MeOH 95:5), there were obtained 550 mg of the desired product O (37% of theory).

Step 2

Trifluoroacetic acid (5.0 mL, 67 mmol) was slowly added to a solution of O (311 mg, 0.68 mmol) in DCM (5 mL) under a blanket of nitrogen as inert gas at RT. After an hour the solvent was removed in vacuo. The residue was taken up in toluene three times and the solvent was removed in vacuo each time. The resulting compound 2-[(furan-2-carbonyl)amino]-4,5,6,7-tetrahydrobenzthiazol-4-carboxylic acid (1-pyrrolidin-3-yl)amide (P) was used in step 3 without further workup.

Step 3

The compound 2-[(furan-2-carbonyl)amino]-4,5,6,7-tetrahydrobenzthiazol-4-carboxylic acid (1-pyrrolidin-3-yl)amide (P) (0.67 mmol) was dissolved in DCM (40 mL) under a blanket of nitrogen. 2,4,6-Trimethoxybenzaldehyde (159 mg, 0.81 mmol) and sodium triacetoxyboron hydride (215 mg, 1.01 mmol) were added. The reaction mixture was stirred overnight at RT under a blanket of nitrogen. Following filtration, removal of the solvent in vacuo, and purification by column chromatography (SiO₂, DCM/MeOH 95:5), there were obtained 233 mg (61% of theory) of the desired product 2-[(furan-2-carbonyl)amino]-4,5,6,7-tetrahydrobenzthiazol-4-carboxylic acid[1-(-2,4,6-trimethoxybenzyl)pyrrolidin-3-yl]amide (Q).

Example 15

2-(2-Phenylpropionylamino)-4,5,6,7-tetrahydrobenzthiazol-4-carboxylic acid[1-(4-phenoxybenzyl)pyrrolidin-3-yl]amide

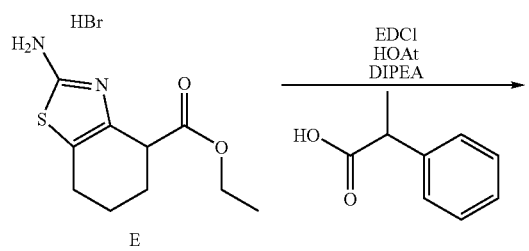

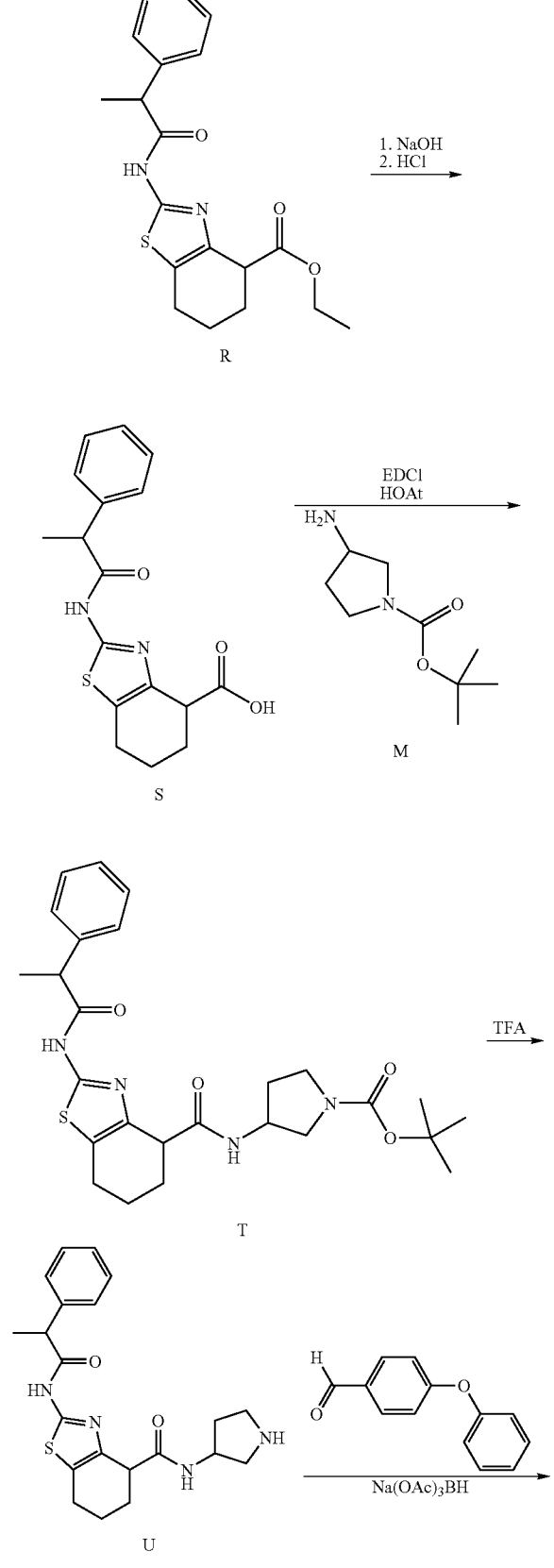

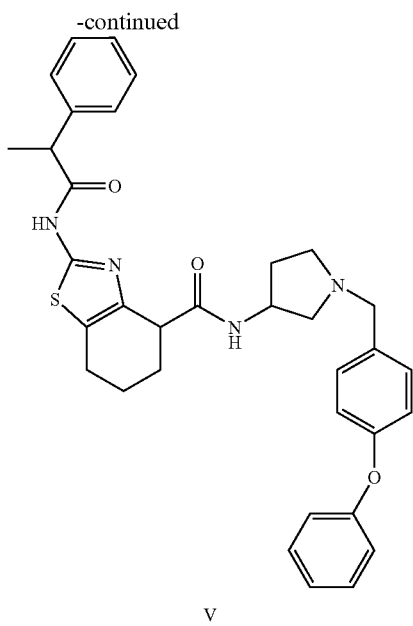

V

Step 1

Ethyl 2-amino-4,5,6,7-tetrahydrobenzthiazole-4-carboxyate hydrobromide (E) (5.0 g, 16.3 mmol), 2-phenylpropionic acid (2.44 g, 16.25 mmol) and DIPEA (2.31 g, 17.87 mmol) were treated with DCM (100 mL). The reaction mixture was cooled to 0° C. and HOAt (0.22 g, 17.87 mmol) and EDCl (3.43 g, 17.91 mmol) were added. The resultant reaction mixture was stirred over a period of 30 minutes at 0° C. and then overnight under a blanket of nitrogen at RT. A 0.5N hydrochloric acid solution in water (100 mL) was added and the aqueous phase was extracted with DCM (100 mL). Following drying of the combined organic phases over $Na_2SO_4$ and removal of the solvent in vacuo there were obtained, following purification of the residue by column chromatography ($SiO_2$, EtOAc/heptane 1:1), 4.95 g of the desired product ethyl 2-(2-phenylpropionylamino)-4,5,6,7-tetrahydrobenzthiazol-4-carboxylate (R) (85% of theory).

Step 2

Water (20 mL) and MeOH (80 mL) were added to ethyl 2-(2-phenylpropionylamino)-4,5,6,7-tetrahydrobenzthiazol-4-carboxylate (R) (4.95 g, 13.8 mmol) and NaOH (5.52 g, 0.138 mol), and the resultant mixture was stirred at RT under a blanket of nitrogen as inert gas until completion of the reaction. Following removal of MeOH, 2N hydrochloric acid solution in water (250 mL) and DCM (250 mL) were added. The phases were separated, and the aqueous phase was extracted a number of times with DCM (a total of 200 mL). Following drying of the combined organic phases over $Na_2SO_4$ and filtration, there was obtained the product 2-(2-phenylpropionylamino)-4,5,6,7-tetrahydrobenzthiazol-4-carboxylic acid (S) in a yield of 4.6 g (corresponding to 100% of theory).

Step 3

The carboxylic acid 2-(2-phenylpropionylamino)-4,5,6,7-tetrahydrobenzthiazol-4-carboxylic acid (S) (1173 mg, 3.5 mmol) was added to a solution of the amine M (603 mg, 3.2 mmol) in dried DCM (15 mL) under a blanket of nitrogen as inert gas. EDCl (682 mg, 3.56 mmol) and HOAt (66 mg, 0.5 mmol) were added at 0° C. The reaction mixture was stirred for one hour at 0° C. and then overnight at RT. The solvent was removed in vacuo and, following purification of the residue by column chromatography ($SiO_2$, DCM/MeOH 98:2 and aluminum oxide, EtOAc/heptane 1:2), there were obtained 520 mg of the desired product T (32% of theory).

Step 4

Trifluoroacetic acid (5.0 mL, 67 mmol) was slowly added to a solution of T (516 mg, 1.03 mmol) in DCM (15 mL) under a blanket of nitrogen as inert gas at RT. After two hours the solvent was removed in vacuo. Following purification of the residue by column chromatography ($SiO_2$, DCM/MeOH 95:5→9:1, in each case with 10% of triethylamine by volume) there were obtained 268 mg (65% of theory) of the desired product 2-(2-phenylpropionylamino)-4,5,6,7-tetrahydrobenzthiazol-4-carboxylic acid (1-pyrrolidin-3-yl)amide (U).

The residue was taken up in toluene three times and the solvent was removed in vacuo each time.

Step 5

The compound 2-(2-phenylpropionylamino)-4,5,6,7-tetrahydrobenzthiazol-4-carboxylic acid (1-pyrrolidin-3-yl) amide (U) (268 mg, 0.67 mmol) was dissolved in DCM (10 mL) under a blanket of nitrogen. 4-Phenoxybenzaldehyde (157 mg, 0.79 mmol) and sodium triacetoxyboron hydride (214 mg, 1.01 mmol) were added.

The reaction mixture was stirred overnight at RT under a blanket of nitrogen. Following filtration, removal of the solvent in vacuo, and purification by column chromatography ($SiO_2$, DCM/MeOH 95:5 with 10% of triethylamine by volume and then $SiO_2$, DCM/MeOH 96:4), there were obtained 210 mg (54% of theory) of the desired product 2-(2-phenylpropionylamino)-4,5,6,7-tetrahydrobenzthiazol-4-carboxylic acid[1-(-4-phenoxybenzyl)pyrrolidin-3-yl] amide (V).

The following substituted 4,5,6,7-tetrahydrobenzthiazol-2-ylamine compounds of the above examples were obtained following the general synthesis instructions described above:

[I] 2-Cyclohexyl-N-{4-[4-(2-Dimethyl aminoethyl)piperazin-1-carbonyl]-4,5,6,7-tetrahydrobenzthiazol-2-yl}acetamide,

[2] N-[4-(4-Methyl-[1,4]diazepam-1-carbonyl)-4,5,6,7-tetrahydrobenzthiazol-2-yl]-2-phenoxy acetamide,

[3] 2-(2-Phenylpropionylamino)-4,5,6,7-tetrahydrobenzthiazol-4-carboxylic acid (3-dimethylaminopropyl) amide,

[4] Naphthalene-2-carboxylic acid[4-(4-methylpiperazin-1-carbonyl)-4,5,6,7-tetrahydrobenzthiazol-2-yl]amide,

[5] N-[4-(2-Pyrrolidin-1-ylmethylpyrrolidin-1-carbonyl)-4,5,6,7-tetrahydrobenzthiazol-2-yl]-2-thiophen-2-ylacetamide,

[6] N-{4-[4-(7-Methoxybenzo[1, 3]dioxol-5-ylmethyl)piperazin-1-carbonyl]-4,5,6,7-tetrahydrobenzthiazol-2-yl}-2-(2-methoxyphenyl)acetamide,

[7] N-{4-[4-(4-Methoxyphenyl)-3-methylpiperazin-1-carbonyl]-4,5,6,7-tetrahydrobenzthiazol-2-yl]-benzamide,

[8] Furan-2-carboxylic acid{4-[4-(4-acetylphenyl)piperazin-1-carbonyl]-4,5,6,7-tetrahydrobenzthiazol-2-yl}amide,

[9] 2-[(Furan-2-carbonyl)amino]-4,5,6,7-tetrahydrobenzthiazol-4-carboxylic acid[1-(214,6-trimethoxybenzyl)pyrrolidin-3-yl]amide,

[10] N-[4-(4-Isopropylpiperazin-1-carbonyl)-4,5,6,7-tetrahydrobenzthiazol-2-yl]-2-phenylpropionamide,

[II] 3-Furan-2-yl-N-[4-(4-thiophen-3-ylmethylpiperazin-1-carbonyl)-4,5,6,7-tetrahydrobenzthiazol-2-yl]acrylamide,

[12] 2-(4-Methoxybenzoylamino)-4,5,6,7-tetrahydrobenzthiazol-4-carboxylic acid [1-(2-chloro-6-fluorobenzyl)pyrrolidin-3-yl]methylamide,

[13] Hexanoic acid[4-(4-pyridin-4-ylpiperazin-1-carbonyl)-4,5,6,7-tetrahydrobenzthiazol-2-yl]amide,

[14] 2-(2-Thiophen-2-ylacetylamino)-4,5,6,7-tetrahydrobenzthiazol-4-carboxylic acid (3-morpholin-4-ylpropyl)amid)

[15] 2-(2-Phenylpropionylamino)-4,5,6,7-tetrahydrobenzthiazol-4-carboxylic acid [1-(4-phenoxybenzyl)pyrrolidin-3-yl]amide,

[16] 2-[(Furan-3-carbonyl)amino]-4,5,6,7-tetrahydrobenzthiazol-4-carboxylic acid (2-azepan-1-ylethyl)amide,

[17] Furan-3-carboxylic acid[4-(4-benzofuran-2-ylmethylpiperazin-1-carbonyl)-4,5,6,7-tetrahydrobenzthiazol-2-yl]amide,

[18] 2-Hexanylamino-4,5,6,7-tetrahydrobenzthiazol-4-carboxylic acid[3-(2-methylpiperidin-1-yl)propyl]amide,

[19] 2-(2-Phenylpropionylamino)-4,5,6,7-tetrahydrobenzthiazol-4-carboxylic acid (2-dimethylaminoethyl)amide,

[20] 2-Ethoxy-N-[4-(4-phenethylpiperazin-1-carbonyl)-4,5,6,7-tetrahydrobenzthiazol-2-yl]benzamide,

[21] 2-(4-Fluorophenoxy)-N-[4-(4-phenylpiperazin-1-carbonyl)-4,5,6,7-tetrahydrobenzthiazol-2-yl]acetamide,

[22] 2-(2-Phenylpropionylamino)-4,5,6,7-tetrahydrobenzthiazol-4-carboxylic acid [2-(1-methylpyrrolidin-2-yl)ethyl]amide,

[23] 2-(3-Furan-2-ylacryloylamino)-4,5,6,7-tetrahydrobenzthiazol-4-carboxylic acid [3-(2-methylpiperidin-1-yl)propyl]amid,

[24] 2-(3,3-Dimethylbutyrylamino)-4,5,6,7-tetrahydrobenzthiazol-4-carboxylic acid (3-dimethylaminopropyl)amide,

[25] N-{4-[4-(4-Chlorobenzyl)piperazin-1-carbonyl]-4,5,6,7-tetrahydrobenzthiazol-2-yl}-4-methoxybenzamide,

[26] Naphthalene-2-carboxylic acid[4-(2-pyrrolidin-1-ylmethylpyrrolidin-1-carbonyl)-4,5,6,7-tetrahydrobenzthiazol-2-yl]amide,

[27] N-[4-(4-Benzofuran-2-ylmethylpiperazin-1-carbonyl)-4,5,6,7-tetrahydrobenzthiazol-2-yl]butyramide,

[28] N-{4-[4-(3-Methoxyphenyl)piperazin-1-carbonyl]-4,5,6,7-tetrahydrobenzthiazol-2-yl}benzamide,

[29] 2-Butyrylamino-4,5,6,7-tetrahydrobenzthiazol-4-carboxylic acid (1-biphenyl-4-ylmethylpyrrolidin-3-yl)methylamide,

[30] 2-(2-Phenoxyacetylamino)-4,5,6,7-tetrahydrobenzthiazol-4-carboxylic acid(2-dimethylaminoethyl)amide,

[31] 2-Ethoxy-N-[4-(2-pyrrolidin-1-ylmethylpyrrolidin-1-carbonyl)-4,5,6,7-tetrahydrobenzthiazol-2-yl]benzamide,

[32] Naphthalene-2-carboxylic acid{4-[4-(2-oxo-2-pyrrolidin-1-ylethyl)piperazin-1-carbonyl]-4,5,6,7-tetrahydrobenzthiazol-2-yl}amide,

[33] 2-(2-Phenylpropionylamino)-4,5,6,7-tetrahydrobenzthiazol-4-carboxylic acid (2-brom-4,5-dimethoxybenzyl)pyrrolidin-3-yl]amide,

[34] Hexanoic acid{4-[4-(2,4,6-trimethoxybenzyl)piperazin-1-carbonyl]-4,5,6,7-tetrahydrobenzthiazol-2-yl}amide,

[35] 2-(3)5-Dimethylbenzoylamino)-4,5,6,7-tetrahydrobenzthiazol-4-carboxylic acid [1-(2-tert-butylsulfanylbenzyl)pyrrolidin-3-yl]amide,

[36] 2-(2-Phenylpropionylamino)-4,5,6,7-tetrahydrobenzthiazol-4-carboxylic acid[1-(2-benzyloxybenzyl)pyrrolidin-3-yl]methylamide,

[37] 2-Hexa-2,4-dienoylamino-4,5,6,7-tetrahydrobenzthiazol-4-carboxylic acid (1-biphenyl-4-ylmethylpyrrolidin-3-yl)methylamide,

[38] 2-(3-Phenylpropionylamino)-4,5,6,7-tetrahydrobenzthiazol-4-carboxylic acid (2-diethylaminoethyl)amide,

[39] 2-(2-Thiophen-2-ylacetylamino)-4,5,6,7-tetrahydrobenzthiazol-4-carboxylic acid(2-azepan-1-ylethyl)amide,

[40] 2-(2-Thiophen-2-ylacetylamino)-4,5,6,7-tetrahydrobenzthiazol-4-carboxylic acid (2-ethoxybenzyl)pyrrolidin-3-yl]methylamide,

[41] 2-Hexanylamino-4,5,6,7-tetrahydrobenzthiazol-4-carboxylic acid(1-benzofuran-2-ylmethylpyrrolidin-3-yl)methylamide,

[42] 2-(2-Phenoxyacetylamino)-4,5,6,7-tetrahydrobenzthiazol-4-carboxylic acid[3-(2-methylpiperidin-1-yl)propyl]amide,

[43] 2-[(Naphthalene-2-carbonyl)amino]-4,5,6,7-tetrahydrobenzthiazol-4-carboxylic acid (2-pyrrolidin-1-ylethyl)amide,

[44] 2-[2-(3,5-Difluorophenyl)acetylamino]-4,5,6,7-tetrahydrobenzthiazol-4-carboxylic acid[1-(2-ethoxybenzyl)pyrrolidin-3-yl]methylamide,

[45] 2-[(Naphthalene-2-carbonyl)amino]-4,5,6,7-tetrahydrobenzthiazol-4-carboxylic acid 4-dimethylaminobenzylamide,

[46] 2-[2-(4-Fluorophenoxy)acetylamino]-4,5,6,7-tetrahydrobenzthiazol-4-carboxylic acid[2-(1-methylpyrrolidin-2-yl)ethyl]amide,

[47] Furan-2-carboxylic acid{4-[4-(2-cyan-phenyl)piperazin-1-carbonyl]-4,5,6,7-tetrahydrobenzthiazol-2-yl]-amide,

[48] 2-(3-Phenylpropionylamino)-4,5,6,7-tetrahydrobenzthiazol-4-carboxylic acid (1-benzofuran-2-ylmethylpyrrolidin-3-yl)methylamide,

[49] 2-Hexa-2,4-dienoylamino-4,5,6,7-tetrahydrobenzthiazol-4-carboxylic acid[1-(2,6-dichlorobenzyl)pyrrolidin-3-yl]methylamide,

[50] 2-[(Furan-2-carbonyl)amino]-4,5,6,7-tetrahydrobenzthiazol-4-carboxylic acid [1-(5-bromo-2-ethoxybenzyl)pyrrolidin-3-yl]amide,

[51] 2-(2-Phenoxyacetylamino)-4,5,6,7-tetrahydrobenzthiazol-4-carboxylic acid[1-(2-ethoxybenzyl)pyrrolidin-3-yl]methylamide,

[52] Hexanoic acid{4-[4-(2-fluorophenyl)piperazin-1-carbonyl]-4,5,6,7-tetrahydrobenzthiazol-2-yl}amide,

[53] Naphthalene-2-carboxylic acid{4-[4-(2-fluorobenzyl)piperazin-1-carbonyl]-4,5,6,7-tetrahydrobenzthiazol-2-yl}amide,

[54] 2-(2-Phenoxyacetylamino)-4,5,6,7-tetrahydrobenzthiazol-4-carboxylic acid methyl-[1-(2-trifluoromethylbenzyl)pyrrolidin-3-yl]amide,

[55] 2-(3-Phenylpropionylamino)-4,5,6,7-tetrahydrobenzthiazol-4-carboxylic acid (1-biphenyl-4-ylmethylpyrrolidin-3-yl)methylamide,

[56] 2-[2-(2-Methoxyphenyl)acetylamino]-4,5,6,7-tetrahydrobenzthiazol-4-carboxylic acid (1-benzofuran-2-ylmethylpyrrolidin-3-yl)methylamide,

[57] 2-(3,5-Difluorophenyl)-N-[4-(2-pyrrolidin-1-ylmethylpyrrolidin-1-carbonyl)-4,5,6,7-tetrahydrobenzthiazol-2-yl]acetamide,

[58] 2-[(Furan-2-carbonyl)amino]-4,5,6,7-tetrahydrobenzthiazol-4-carboxylic acid 4-dimethylaminobenzylamide,

[59] Hexanoic acid{4-[4-(3-fluoro-4-methoxybenzyl)piperazin-1-carbonyl]-4,5,6,7-tetrahydrobenzthiazol-2-yl}amide,

[60] N-{4-[4-(4-Methoxyphenyl)-3-methylpiperazin-1-carbonyl]-4,5,6,7-tetrahydrobenzthiazol-2-yl}-2-phenylpropionamide,

[61] 2-Hexa-2,4-dienoylamino-4,5,6,7-tetrahydrobenzthiazol-4-carboxylic acid[1-(2-chloro-6-fluorobenzyl)pyrrolidin-3-yl]methylamide,

[62] 2-[2-(3,5-Difluorophenyl)acetylamino]-4,5,6,7-tetrahydrobenzthiazol-4-carboxylic acid[1-(2,6-dichlorobenzyl)pyrrolidin-3-yl]methylamide,

[63] 2-[2-(4-Fluorophenoxy)acetylamino]-4,5,6,7-tetrahydrobenzthiazol-4-carboxylic acid[1-(2-ethoxybenzyl)pyrrolidin-3-yl]methylamide,

[64] Furan-3-carboxylic acid[4-(4-pyridin-2-ylpiperazin-1-carbonyl)-4,5,6,7-tetrahydrobenzthiazol-2-yl]amide,

[65] Hexanoic acid[4-(4-benzofuran-2-ylmethylpiperazin-1-carbonyl)-4,5,6,7-tetrahydrobenzthiazol-2-yl]amide,

[66] 2-Phenoxy-N-{4-[4-(1-phenylethyl)piperazin-1-carbonyl]-4,5,6,7-tetrahydrobenzthiazol-2-yl}acetamide,

[67] 2-(2-Cyclohexylacetylamino)-4,5,6,7-tetrahydrobenzthiazol-4-carboxylic acid [1-(2,6-dichlorobenzyl)pyrrolidin-3-yl]methylamide,

[68] 2-(2-Cyclohexylacetylamino)-4,5,6,7-tetrahydrobenzthiazol-4-carboxylic acid [3-(methylphenyl-amino)propyl]amide,

[69] 2-(2-Ethoxybenzoylamino)-4,5,6,7-tetrahydrobenzthiazol-4-carboxylic acid[3-(methylphenyl-amino)propyl]amide,

[70] 3-Phenyl-N-{4-[4-(5-trifluoromethylpyridin-2-yl)piperazin-1-carbonyl]-4,5,6,7-tetrahydrobenzthiazol-2-yl}propionamide,

[71] Furan-3-carboxylic acid[4-(4-phenethylpiperazin-1-carbonyl)-4,5,6,7-tetrahydrobenzthiazol-2-yl]amide,

[72] 3-Phenyl-N-{4-[4-(3-trifluoromethylphenyl)piperazin-1-carbonyl]-4,5,6,7-tetrahydrobenzthiazol-2-yl}propionamide,

[73] 2-(3,3-Dimethylbutyrylamino)-4,5,6,7-tetrahydrobenzthiazol-4-carboxylic acid [1-(2-benzyloxybenzyl)pyrrolidin-3-yl]amide,

[74] 2-(3,5-Difluorophenyl)-N-{4-[4-(3-trifluoromethylphenyl)piperazin-1-carbonyl]-4,5,6,7-tetrahydrobenzthiazol-2-yl}acetamide,

[75] 2-Ethoxy-N-{4-[4-(1-phenylethyl)piperazin-1-carbonyl]-4,5,6,7-tetrahydrobenzthiazol-2-yl}benzamide,

[76] 3-Furan-2-yl-N-{4-[4-(3-trifluoromethylphenyl)piperazin-1-carbonyl]-4,5,6,7-tetrahydrobenzthiazol-2-yl}acrylamide,

[77] N-{4-[4-(2-Cyan-phenyl)piperazin-1-carbonyl]-4,5,6,7-tetrahydrobenzthiazol-2-yl}-3-phenylpropionamide,

[78] 2-(Cyclohexylacetylamino)-4,5,6,7-tetrahydrobenzthiazol-4-carboxylic acid [1-(2-chloro-6-fluorobenzyl)pyrrolidin-3-yl]methylamide,

[79] N-{4-[4-(2-Methoxynaphthalene-1-ylmethyl)piperazin-1-carbonyl]-4,5,6,7-tetrahydrobenzthiazol-2-yl}-3,3-dimethylbutyramide,

[80] 2-(3,3-Dimethylbutyrylamino)-4,5,6,7-tetrahydrobenzthiazol-4-carboxylic acid (2,5-diethoxy-4-morpholin-4-ylphenyl)amide,

[81] N-{4-[4-(2-Chlorophenyl)piperazin-1-carbonyl]-4,5,6,7-tetrahydrobenzthiazol-2-yl}-2-(4-fluorophenyl)acetamide,

[82] N-[4-(4-Benzylpiperazin-1-carbonyl)-4,5,6,7-tetrahydrobenzthiazol-2-yl]-3,3-dimethylbutyramide,

[83] N-[4-(4-Benzhydrylpiperazin-1-carbonyl)-4,5,6,7-tetrahydrobenzthiazol-2-yl]-2-(3,5-difluorophenyl)acetamide,

[84] N-[4-(4-Benzhydrylpiperazin-1-carbonyl)-4,5,6,7-tetrahydrobenzthiazol-2-yl]-2-thiophen-2-ylacetamide,

[85] N-{4-[4-(2-Chlorophenyl)piperazin-1-carbonyl]-4,5,6,7-tetrahydrobenzthiazol-2-yl}-2-ethoxybenzamide,

[86] 3,3-Dimethyl-N-{4-[4-(5-trifluoromethylpyridin-2-yl)piperazin-1-carbonyl]-4,5,6,7-tetrahydrobenzthiazol-2-yl}butyramide,

[87] 3,3-Dimethyl-N-{4-[4-(3-phenylallyl)piperazin-1-carbonyl]-4,5,6,7-tetrahydrobenzthiazol-2-yl}butyramide,

[88] N-[4-(4-Benzhydrylpiperazin-1-carbonyl)-4,5,6,7-tetrahydrobenzthiazol-2-yl]-2-cyclohexylacetamide,

[89] Furan-2-carboxylic acid[4-(4-phenylpiperazin-1-carbonyl)-4,5,6,7-tetrahydrobenzthiazol-2-yl]amide.

Table I below lists the carboxylic chlorides and amines used in the synthesis of the compounds of the invention as defined in Examples 1 to 89 respectively.

TABLE I

| Example | Carboxylic chlorides | Amines |
|---------|----------------------|--------|
| 1 | 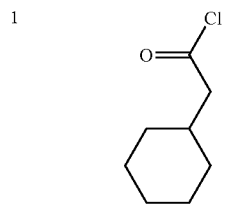 | 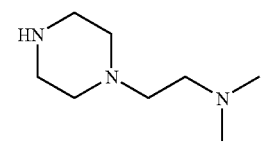 |
| 2 | 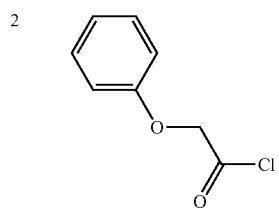 | 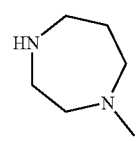 |

TABLE I-continued
| Example | Carboxylic chlorides | Amines |
|---|---|---|
| 3 | 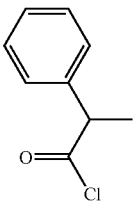 | 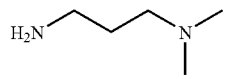 |
| 4 | 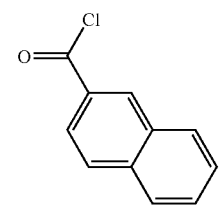 | 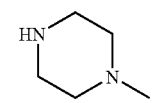 |
| 5 | 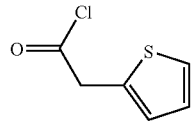 | 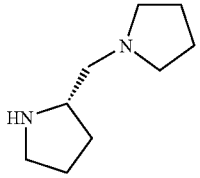 |
| 6 | 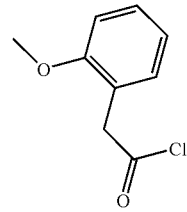 | 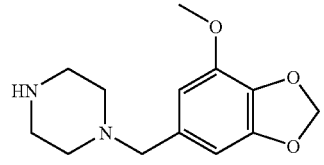 |
| 7 | 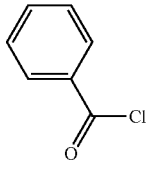 | 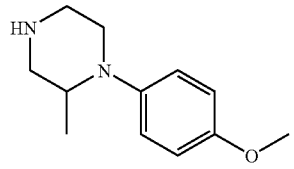 |
| 8 | 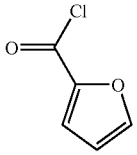 | 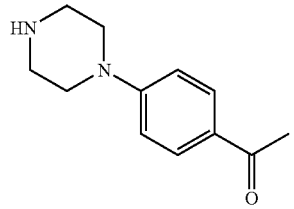 |
| 9 | 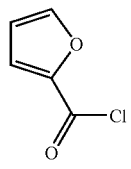 | 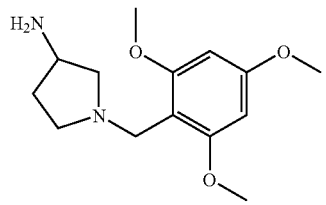 |

TABLE I-continued
| Example | Carboxylic chlorides | Amines |
|---|---|---|
| 10 | 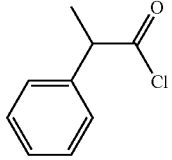 | 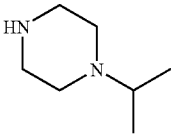 |
| 11 | 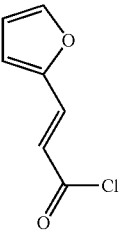 | 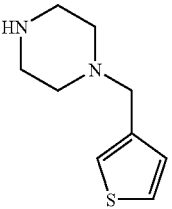 |
| 12 | 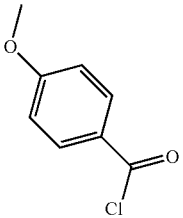 | 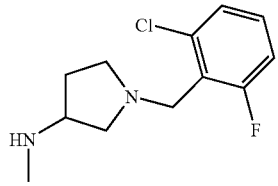 |
| 13 | 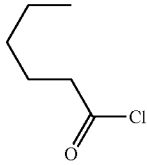 | 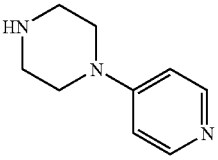 |
| 14 | 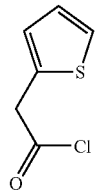 | 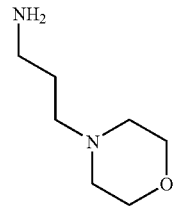 |
| 15 | 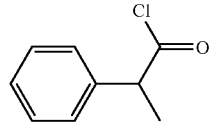 | 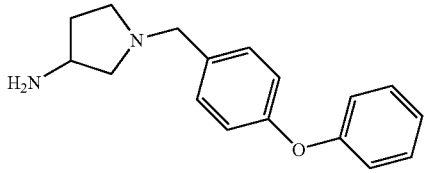 |
| 16 | 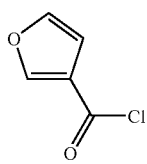 | 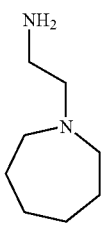 |

TABLE I-continued
| Example | Carboxylic chlorides | Amines |
|---|---|---|
| 17 | 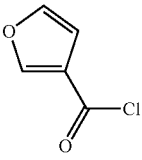 | 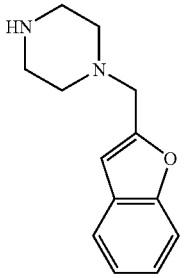 |
| 18 | 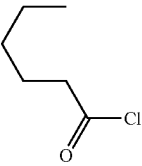 | 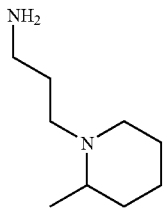 |
| 19 | 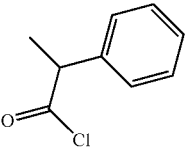 | 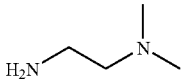 |
| 20 | 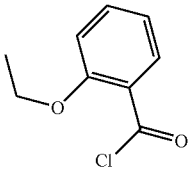 | 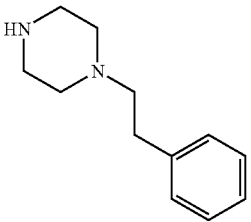 |
| 21 | 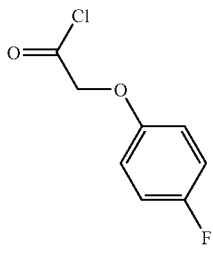 | 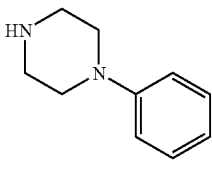 |
| 22 | 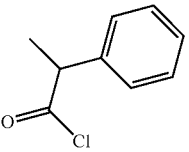 | 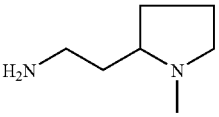 |
| 23 | 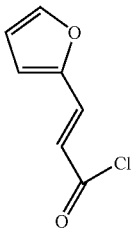 | 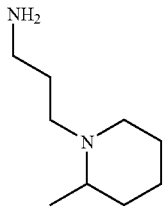 |

TABLE I-continued

| Example | Carboxylic chlorides | Amines |
| --- | --- | --- |
| 24 | 4,4-dimethyl-3-oxopentanoyl chloride | 3-(dimethylamino)propylamine |
| 25 | 4-methoxybenzoyl chloride | 1-(4-chlorobenzyl)piperazine |
| 26 | 2-naphthoyl chloride | (S)-2-(pyrrolidin-1-ylmethyl)pyrrolidine |
| 27 | butyryl chloride | 1-(benzofuran-2-ylmethyl)piperazine |
| 28 | benzoyl chloride | 1-(3-methoxyphenyl)piperazine |
| 29 | butyryl chloride | 1-([1,1'-biphenyl]-4-ylmethyl)-N-methylpyrrolidin-3-amine |

TABLE I-continued
| Example | Carboxylic chlorides | Amines |
|---|---|---|
| 30 | 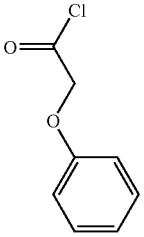 | 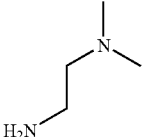 |
| 31 | 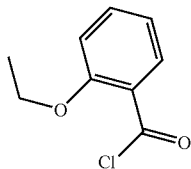 | 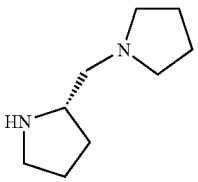 |
| 32 | 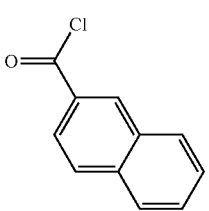 | 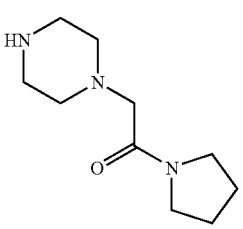 |
| 33 | 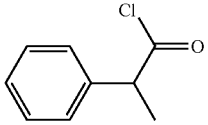 | 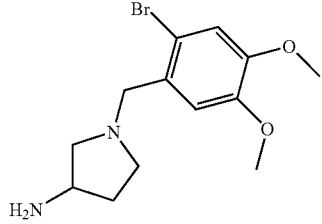 |
| 34 | 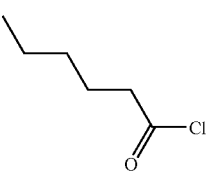 | 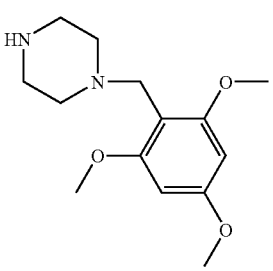 |
| 35 | 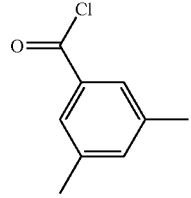 | 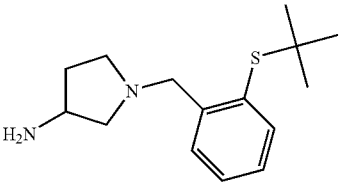 |

TABLE I-continued

| Example | Carboxylic chlorides | Amines |
|---|---|---|
| 36 | (structure) | (structure) |
| 37 | (structure) | (structure) |
| 38 | (structure) | (structure) |
| 39 | (structure) | (structure) |
| 40 | (structure) | (structure) |
| 41 | (structure) | (structure) |

TABLE I-continued

| Example | Carboxylic chlorides | Amines |
|---|---|---|
| 42 | phenoxyacetyl chloride | 3-(2-methylpiperidin-1-yl)propan-1-amine |
| 43 | 2-naphthoyl chloride | 2-(pyrrolidin-1-yl)ethan-1-amine |
| 44 | (3,5-difluorophenyl)acetyl chloride | 1-(2-ethoxybenzyl)-N-methylpyrrolidin-3-amine |
| 45 | 2-naphthoyl chloride | 4-(dimethylamino)benzylamine |
| 46 | (4-fluorophenoxy)acetyl chloride | 2-(1-methylpyrrolidin-2-yl)ethan-1-amine |
| 47 | furan-2-carbonyl chloride | 2-(piperazin-1-yl)benzonitrile |

TABLE I-continued
| Example | Carboxylic chlorides | Amines |
|---|---|---|
| 48 | 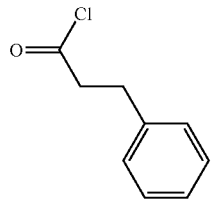 | 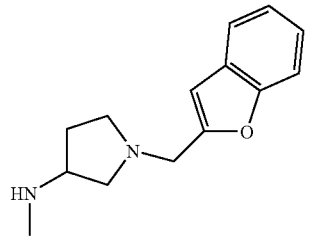 |
| 49 | 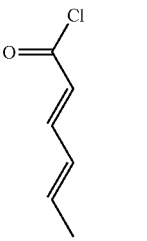 | 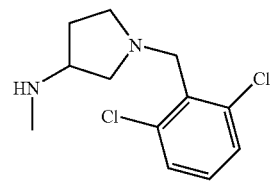 |
| 50 | 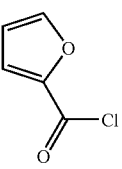 | 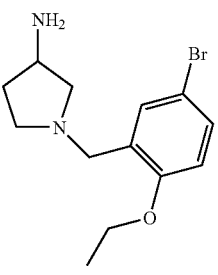 |
| 51 | 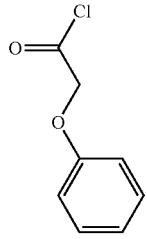 | 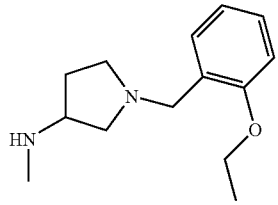 |
| 52 | 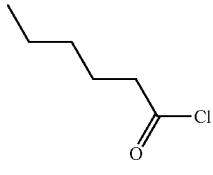 | 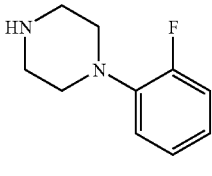 |
| 53 | 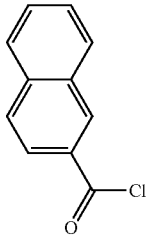 | 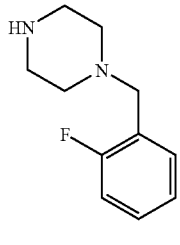 |

TABLE I-continued

| Example | Carboxylic chlorides | Amines |
| --- | --- | --- |
| 54 | phenoxyacetyl chloride | 1-(2-(trifluoromethyl)benzyl)-N-methylpyrrolidin-3-amine |
| 55 | 3-phenylpropanoyl chloride | 1-([1,1'-biphenyl]-4-ylmethyl)-N-methylpyrrolidin-3-amine |
| 56 | 2-(2-methoxyphenyl)acetyl chloride | 1-(benzofuran-2-ylmethyl)-N-methylpyrrolidin-3-amine |
| 57 | 2-(3,5-difluorophenyl)acetyl chloride | (S)-2-(pyrrolidin-1-ylmethyl)pyrrolidine |
| 58 | furan-2-carbonyl chloride | 4-(aminomethyl)-N,N-dimethylaniline |
| 59 | pentanoyl chloride | 1-(3-fluoro-4-methoxybenzyl)piperazine |

TABLE I-continued

| Example | Carboxylic chlorides | Amines |
| --- | --- | --- |
| 60 | 2-phenylpropanoyl chloride | 1-(4-methoxyphenyl)-2-methylpiperazine |
| 61 | (2E,4E)-hexa-2,4-dienoyl chloride | 1-(2-chloro-6-fluorobenzyl)-N-methylpyrrolidin-3-amine |
| 62 | 2-(3,5-difluorophenyl)acetyl chloride | 1-(2,6-dichlorobenzyl)-N-methylpyrrolidin-3-amine |
| 63 | 2-(4-fluorophenoxy)acetyl chloride | 1-(2-ethoxybenzyl)-N-methylpyrrolidin-3-amine |
| 64 | furan-3-carbonyl chloride | 1-(pyridin-2-yl)piperazine |
| 65 | hexanoyl chloride | 1-(benzofuran-2-ylmethyl)piperazine |

TABLE I-continued

| Example | Carboxylic chlorides | Amines |
|---------|---------------------|--------|
| 66 | phenoxyacetyl chloride | 1-(1-phenylethyl)piperazine |
| 67 | cyclohexylacetyl chloride | N-methyl-1-(2,6-dichlorobenzyl)pyrrolidin-3-amine |
| 68 | cyclohexylacetyl chloride | N-methyl-N-phenyl-propane-1,3-diamine |
| 69 | 2-ethoxybenzoyl chloride | N-methyl-N-phenyl-propane-1,3-diamine |
| 70 | 3-phenylpropanoyl chloride | 1-(5-trifluoromethylpyridin-2-yl)piperazine |
| 71 | furan-3-carbonyl chloride | 1-(2-phenylethyl)piperazine |
| 72 | 3-phenylpropanoyl chloride | 1-(3-trifluoromethylphenyl)piperazine |

TABLE I-continued

| Example | Carboxylic chlorides | Amines |
|---------|---------------------|--------|
| 73 | 3,3-dimethylbutanoyl chloride | 1-[(2-phenoxyphenyl)methyl]pyrrolidin-3-amine |
| 74 | (3,5-difluorophenyl)acetyl chloride | 1-[3-(trifluoromethyl)phenyl]piperazine |
| 75 | 2-ethoxybenzoyl chloride | 1-(1-phenylethyl)piperazine |
| 76 | (2E)-3-(furan-2-yl)prop-2-enoyl chloride | 1-[3-(trifluoromethyl)phenyl]piperazine |
| 77 | 3-phenylpropanoyl chloride | 2-(piperazin-1-yl)benzonitrile |
| 78 | 2-cyclohexylacetyl chloride | 1-[(2-chloro-6-fluorophenyl)methyl]-N-methylpyrrolidin-3-amine |
| 79 | 3,3-dimethylbutanoyl chloride | 1-[(2-methoxynaphthalen-1-yl)methyl]piperazine |

TABLE I-continued

| Example | Carboxylic chlorides | Amines |
|---|---|---|
| 80 | (CH₃)₃C-CH₂-C(O)Cl | 4-(4-morpholinyl)-2,5-diethoxyaniline |
| 81 | 4-fluorophenylacetyl chloride | 1-(2-chlorophenyl)piperazine |
| 82 | (CH₃)₃C-CH₂-C(O)Cl | 1-benzylpiperazine |
| 83 | 3,5-difluorophenylacetyl chloride | 4-(diphenylmethyl)piperidine |
| 84 | 2-thiopheneacetyl chloride | 4-(diphenylmethyl)piperidine |
| 85 | 2-ethoxybenzoyl chloride | 1-(2-chlorophenyl)piperazine |

TABLE I-continued

| Example | Carboxylic chlorides | Amines |
|---|---|---|
| 86 | (CH3)3C-CH2-C(=O)Cl | 1-(5-trifluoromethylpyridin-2-yl)piperazine |
| 87 | (CH3)3C-CH2-C(=O)Cl | 1-cinnamylpiperazine |
| 88 | cyclohexyl-CH2-C(=O)Cl | 4-(diphenylmethyl)piperidine |

Pharmacological Data

I. Analgesic Test Using the Writhing Test on Mice

The analgesic action of the substituted 4,5,6,7-tetrahydrobenzthiazol-2-ylamine compounds of the invention was determined as described above. In Table II below the corresponding data for the compound of Example 89 of the invention are listed:

TABLE II

| Compound according to Example | % Inhibition of writhing reactions at 10 mg/kg intravenous |
|---|---|
| 89 | 41 |

The compounds of the invention show good to very good analgesic activity.

II. Determination of the Inhibition of Noradrenaline Reuptake and Serotonine Reuptake (NA and 5-HT Uptake Inhibition)

The inhibition of noradrenaline uptake and the inhibition of 5-HT uptake by the substituted 4,5,6,7-tetrahydrobenzthiazol-2-ylamine compounds of the general formula I of the invention were determined in the manner described above. The compounds of the invention show a good to very good inhibition of NA and 5-HT reuptake.

The data of some of the compounds of the invention are listed in Table III below:

TABLE III

| Compound of | % Inhibition of 5-HT uptake [10 µM] | % Inhibition of NA uptake [10 µM] |
|---|---|---|
| Example 1 | 65 | |
| Example 2 | 58 | |
| Example 3 | 61 | 65 |
| Example 4 | 48 | |
| Example 5 | 41 | |
| Example 6 | 51 | |
| Example 7 | 51 | 48 |
| Example 8 | 89 | 78 |
| Example 9 | 53 | 98 |
| Example 10 | 42 | 64 |
| Example 11 | | 57 |
| Example 12 | 55 | 48 |
| Example 14 | 50 | 43 |
| Example 15 | | 91 |
| Example 16 | | 88 |
| Example 17 | 72 | 81 |
| Example 18 | 57 | 43 |
| Example 19 | | 71 |
| Example 20 | 64 | 77 |
| Example 21 | 47 | 55 |
| Example 22 | 44 | 60 |
| Example 23 | 57 | |
| Example 24 | 89 | |
| Example 25 | 53 | |
| Example 26 | 80 | |
| Example 27 | 61 | 47 |
| Example 28 | 48 | 60 |
| Example 29 | 55 | 73 |
| Example 30 | 64 | |
| Example 31 | 59 | |
| Example 32 | 51 | |
| Example 33 | 63 | 79 |
| Example 34 | 63 | 50 |
| Example 35 | 41 | |
| Example 36 | | 62 |
| Example 37 | 44 | |
| Example 38 | | 42 |
| Example 39 | 49 | 50 |
| Example 40 | 48 | 47 |
| Example 41 | 77 | |
| Example 42 | 42 | |

TABLE III-continued

| Compound of | % Inhibition of 5-HT uptake [10 μM] | % Inhibition of NA uptake [10 μM] |
|---|---|---|
| Example 43 | 63 | |
| Example 44 | 41 | |
| Example 45 | 42 | |
| Example 46 | 53 | |
| Example 47 | | 47 |
| Example 48 | 51 | 67 |
| Example 49 | 51 | 44 |
| Example 50 | 72 | 93 |
| Example 51 | 59 | |
| Example 52 | | 72 |
| Example 53 | 42 | |
| Example 54 | | 44 |
| Example 55 | 54 | 44 |
| Example 56 | | 49 |
| Example 57 | 72 | |
| Example 58 | | 72 |
| Example 59 | 46 | |
| Example 60 | | 41 |
| Example 61 | 46 | 45 |
| Example 62 | 53 | |
| Example 64 | 48 | 53 |
| Example 65 | 44 | |
| Example 66 | | 48 |
| Example 67 | 97 | 42 |
| Example 68 | 84 | |
| Example 69 | 80 | |
| Example 70 | 44 | |
| Example 71 | 66 | 90 |
| Example 72 | 84 | 51 |
| Example 73 | 71 | 75 |
| Example 74 | 82 | |
| Example 75 | 59 | 51 |
| Example 76 | 62 | |
| Example 77 | | 44 |
| Example 78 | 54 | 41 |
| Example 79 | | 71 |
| Example 80 | 52 | |
| Example 81 | 50 | 80 |
| Example 82 | 41 | 64 |
| Example 83 | 44 | |
| Example 84 | 53 | |
| Example 85 | 48 | |
| Example 86 | 54 | |
| Example 87 | 56 | 46 |
| Example 88 | 41 | |
| Example 89 | | 77 |

What is claimed is:

1. A compound corresponding to formula I:

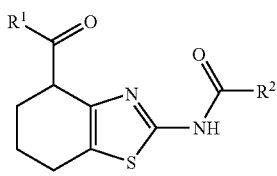

I wherein
$R^1$ represents a —$NR^3R^4$ group or a —$NR^5R^6$ group;
$R^2$ represents
a linear or branched, saturated or unsaturated, unsubstituted, monosubstituted or polysubstituted aliphatic group, or
a saturated or unsaturated, unsubstituted, monosubstituted or polysubstituted cycloaliphatic group, which optionally includes one or more heteroatoms as ring members and which can be bonded via an unsubstituted, monosubstituted or polysubstituted alkylene group, alkenylene group, or alkynylene group, which groups optionally include one or more heteroatoms as links, or
an unsubstituted, monosubstituted or polysubstituted aryl group or heteroaryl group which can be bonded via an unsubstituted, monosubstituted or polysubstituted alkylene group, alkenylene group, or alkynylene group, optionally including one or more heteroatoms as links,
$R^3$ represents
a hydrogen atom, a linear or branched, saturated or unsaturated, unsubstituted, monosubstituted or polysubstituted aliphatic group, or
a saturated or unsaturated, unsubstituted, monosubstituted or polysubstituted cycloaliphatic group which optionally includes one or more heteroatoms as ring members and which can be bonded via an unsubstituted, monosubstituted or polysubstituted alkylene group, alkenylene group, or alkynylene group, optionally including one or more heteroatoms as links, or
an unsubstituted, monosubstituted or polysubstituted aryl group or heteroaryl group which can be bonded via an unsubstituted, monosubstituted or polysubstituted alkylene group, alkenylene group, or alkynylene group, which groups optionally include one or more heteroatoms as links,
$R^4$ represents
a hydrogen atom, or
a linear or branched, saturated or unsaturated, unsubstituted, monosubstituted or polysubstituted aliphatic group, or
a saturated or unsaturated, unsubstituted, monosubstituted or polysubstituted cycloaliphatic group which optionally includes one or more heteroatoms as ring members and which can be bonded via an unsubstituted, monosubstituted or polysubstituted alkylene group, alkenylene group, or alkynylene group, which groups optionally include one or more heteroatoms as links, or
an unsubstituted, monosubstituted or polysubstituted aryl group or heteroaryl group which can be bonded via an unsubstituted, monosubstituted or polysubstituted alkylene group, alkenylene group, or alkynylene group, which groups optionally include one or more heteroatoms as links,
$R^5$ and $R^6$ together with the nitrogen atom to which they are attached form a saturated, unsaturated, or aromatic, unsubstituted, monosubstituted or polysubstituted heterocyclic group optionally including one or more further heteroatoms as ring members; or
a physiologically acceptable salt or solvate thereof.

2. A compound according to claim 1, wherein said compound is a solvate, and said solvate is a hydrate.

3. A compound according to claim 1, wherein said compound is a pure stereoisomer, and said stereoisomer is a pure enantiomer or diastereoisomer.

4. A compound according to claim 1, wherein said compound is a mixture of stereoisomers, and said mixture is a racemic mixture.

5. A compound according to claim 1, wherein $R^2$ represents
a linear or branched, saturated or unsaturated, unsubstituted, monosubstituted or polysubstituted aliphatic $C_1$-$C_{10}$ group, or saturated or unsaturated, three-membered to seven-membered, unsubstituted, monosubstituted or polysubstituted cycloaliphatic group, which optionally includes one or more heteroatoms as ring members and which can be bonded via an unsubstituted, monosubstituted or polysubstituted $C_1$-$C_{10}$ alkylene group, $C_2$-$C_{10}$ alkenylene group, or $C_2$-$C_{10}$ alkynylene group, which groups optionally include as links, or an unsubstituted, monosubstituted or polysubstituted five-membered to twelve-membered aryl group or heteroaryl group which can be bonded via an unsubstituted, monosubstituted or polysubstituted $C_1$-$C_{10}$ alkylene group, $C_2$-$C_{10}$ alkenylene group, or $C_2$-$C_{10}$ alkynylene group, optionally including an at least monosubstituted heteroatom as link.

6. A compound according to claim 5, wherein $R^2$ represents:

a linear or branched $C_1$-$C_{10}$ alkyl group, a linear or branched $C_2$-$C_{10}$ alkenyl group, or a saturated or unsaturated, unsubstituted, monosubstituted or polysubstituted five-membered or six-membered cycloaliphatic group, optionally including one or more heteroatoms as ring members, which cycloaliphatic group can be bonded via an unsubstituted, monosubstituted or polysubstituted $C_1$-$C_5$ alkylene group or $C_1$-$C_2$ alkenylene group, which groups optionally include one or more heteroatoms as links, or a phenyl group, 1-naphthyl group, 2-naphthyl group, 2-furanyl (2-furyl) group, 3-furanyl (3-furyl) group, 2-thiophenyl (2-thienyl) group, or 3-thiophenyl (3-thienyl) group, which groups are each at least monosubstituted and/or can be bonded via an unsubstituted, monosubstituted or polysubstituted $C_1$-$C_5$ alkylene group or $C_2$-$C_5$ alkenylene group, which groups optionally include one or more heteroatoms as links.

7. A compound according to claim 6, wherein $R^2$ represents:

a linear or branched $C_1$-$C_5$ alkyl group, a linear or branched $C_2$-$C_5$ alkenyl group, a saturated or unsaturated, unsubstituted, monosubstituted or polysubstituted six-membered cycloaliphatic group optionally including one or more heteroatoms as ring members, which six-membered cycloaliphatic group can be bonded via a $C_1$-$C_3$ alkylene group, or a phenyl group, 1-naphthyl group, 2-naphthyl group, 2-furanyl group, 3-furanyl group, 2-thiophenyl group or 3-thiophenyl group, which groups are in each case at least monosubstituted and/or can be bonded via an unsubstituted, monosubstituted or polysubstituted $C_1$-$C_5$ alkylene group or $C_2$-$C_5$ alkenylene group, which groups optionally include one or more oxygen atoms as links.

8. A compound according to claim 1, wherein $R^3$ represents:

a hydrogen atom, a linear or branched, saturated or unsaturated, unsubstituted, monosubstituted or polysubstituted aliphatic $C_1$-$C_{10}$ group, or a saturated or unsaturated, unsubstituted, monosubstituted or polysubstituted three-membered to seven-membered cycloaliphatic group optionally including one or more heteroatoms as ring members, which cycloaliphatic group can be bonded via an unsubstituted, monosubstituted or polysubstituted $C_1$-$C_{10}$ alkylene group, $C_2$-$C_{10}$ alkenylene group, or $C_2$-$C_{10}$ alkynylene group, which groups optionally include one or more heteroatoms as links, or an unsubstituted, monosubstituted or polysubstituted five-membered to twelve-membered aryl group or heteroaryl group, which can be bonded via an unsubstituted, monosubstituted or polysubstituted $C_1$-$C_{10}$ alkylene group, $C_2$-$C_{10}$ alkenylene group, or $C_2$-$C_{10}$ alkynylene group, which groups optionally include one or more heteroatoms as links.

9. A compound according to claim 8, wherein $R^3$ represents:

a hydrogen atom, or a linear or branched, unsubstituted, monosubstituted or polysubstituted $C_1$-$C_{10}$ alkyl group, or a saturated or unsaturated, unsubstituted, monosubstituted or polysubstituted five-membered, six-membered, or seven-membered cycloaliphatic group optionally including one or more heteroatoms as ring members, which cycloaliphatic group can be bonded via an unsubstituted, monosubstituted or polysubstituted $C_1$-$C_{10}$ alkylene group, $C_2$-$C_{10}$ alkenylene group, or $C_2$-$C_{10}$ alkynylene group, which groups optionally include one or more heteroatoms as links, or an unsubstituted, monosubstituted or polysubstituted five-membered to twelve-membered aryl group or heteroaryl group, which can be bonded via an unsubstituted, monosubstituted or polysubstituted $C_1$-$C_{10}$ alkylene group, $C_2$-$C_{10}$ alkenylene group, or $C_2$-$C_{10}$ alkynylene group, which groups optionally include one or more heteroatoms as links.

10. A compound according to claim 9, wherein $R^3$ represents:

a hydrogen atom, or a linear or branched, unsubstituted, monosubstituted or polysubstituted $C_{1-3}$ alkyl group, or a cycloaliphatic group bonded via a $C_{1-3}$ alkylene group and selected from the group consisting of

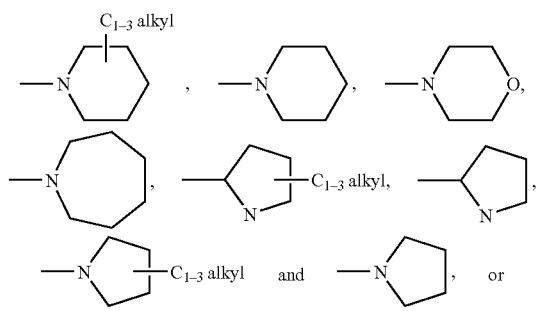

a cycloaliphatic group corresponding to the formula

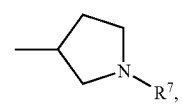

wherein $R^7$ represents a phenyl group or benzofuranyl group bonded via a methylene group and optionally monosubstituted or polysubstituted by the same or different substituents selected from the group consisting of F, Cl, Br, $CF_3$, $CHF_2$, $CH_2F$, phenoxy, benzyloxy, phenyl, $C_{1-4}$ alkoxy and $C_{1-4}$ alkylthio, or a phenyl group optionally bonded via a methylene group, which phenyl group can be monosubstituted or polysubstituted by the same or different substituents selected from the group consisting of di-($C_{1-3}$)-alkylamino, $C_{1-3}$ methoxy, and morpholynyl.

11. A compound according to claim 1, wherein $R^4$ represents:

a hydrogen atom, or a linear or branched, saturated or unsaturated, unsubstituted, monosubstituted or polysubstituted aliphatic $C_1$-$C_{10}$ group, or a saturated or unsaturated, unsubstituted, monosubstituted or polysubstituted three-membered to seven-membered cycloaliphatic group which optionally includes one or more heteroatoms as ring members and which can be bonded via an unsubstituted, monosubstituted or polysubstituted $C_1$-$C_{10}$ alkylene group, $C_2$-$C_{10}$ alkenylene group, or $C_2$-$C_{10}$ alkynylene group, which groups optionally include one or more heteroatoms as links, or an unsubstituted, monosubstituted or polysubstituted five-membered to twelve-membered aryl group or heteroaryl group which can be bonded via an unsubstituted, monosubstituted or polysubstituted $C_1$-$C_{10}$ alkylene group, $C_2$-$C_{10}$ alkenylene group, or $C_2$-$C_{10}$ alkynylene group, which groups optionally include one or more heteroatoms as links.

12. A compound according to claim 11, wherein R4 represents:

a hydrogen atom, or a linear or branched, unsubstituted, monosubstituted or polysubstituted $C_1$-$C_{10}$ alkyl group, or a saturated or unsaturated, unsubstituted, monosubstituted or polysubstituted five-membered, six-membered, or seven-membered cycloaliphatic group which optionally includes one or more heteroatoms as ring members and which can be bonded via an unsubstituted, monosubstituted or polysubstituted $C_1$-$C_{10}$ alkylene group, $C_2$-$C_{10}$ alkenylene group, or $C_2$-$C_{10}$ alkynylene group, which groups optionally include one or more heteroatoms as links, or an unsubstituted, monosubstituted or polysubstituted five-membered to twelve-membered aryl group or heteroaryl group which can be bonded via an unsubstituted, monosubstituted or polysubstituted $C_1$-$C_{10}$ alkylene group, $C_2$-$C_{10}$ alkenylene group, or $C_2$-$C_{10}$ alkynylene group, which groups optionally include one or more heteroatoms as links.

13. A compound according to claim 12, wherein $R^4$ represents:

a linear or branched, unsubstituted, monosubstituted or polysubstituted $C_{1-3}$ alkyl group, or a cycloaliphatic group bonded via a $C_{1-3}$ alkylene group and selected from the group consisting of:

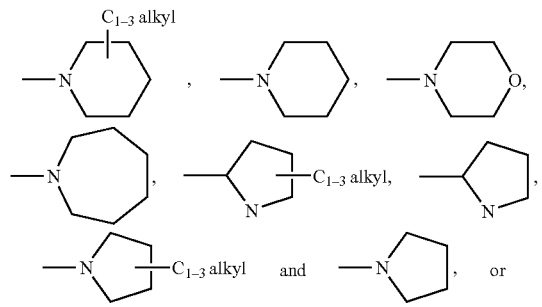

a cycloaliphatic group corresponding to the formula

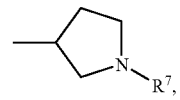

wherein $R^7$ represents a phenyl group or benzofuranyl group which is bonded via a methylene group and which can be monosubstituted or polysubstituted by the same or different substituents selected from the group consisting of F, Cl, Br, $CF_3$, $CHF_2$, $CH_2F$, phenoxy, benzyloxy, phenyl, $C_{1-4}$ alkoxy, or $C_{1-4}$ alkylthio, or a phenyl group optionally bonded via a methylene group, which phenyl group can be monosubstituted or polysubstituted by the same or different substituents selected from the group consisting of di-($C_{1-3}$)-alkylamino, $C_{1-3}$ methoxy, and morpholynyl.

14. A compound according to claim 1, wherein $R^5$ and $R^6$ together with the nitrogen atom to which they are bound form a saturated, unsaturated or aromatic, unsubstituted, monosubstituted or polysubstituted five-membered, six-membered or seven-membered heterocyclic group optionally including one or more further heteroatoms as ring members.

15. A compound according to claim 14, wherein $R^5$ and $R^6$ together with the nitrogen atom to which they are bound form:

a group selected from the group consisting of

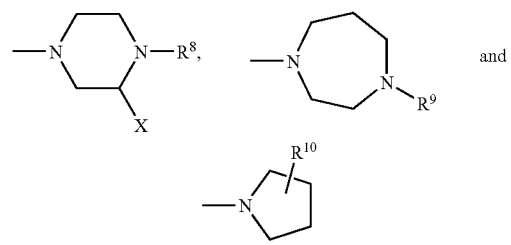

wherein
X represents hydrogen or a linear or branched $C_{1-3}$ alkyl group, and
$R^8$, $R^9$, and $R^{10}$ independently represent a linear or branched, saturated or unsaturated, unsubstituted, monosubstituted or polysubstituted aliphatic $C_{1-6}$ group, or a saturated or unsaturated, unsubstituted, monosubstituted or polysubstituted five-membered, six-membered or seven-membered cycloaliphatic group optionally including one or more heteroatoms as ring members and optionally bonded via an unsubstituted, monosubstituted or polysubstituted $C_{1-6}$ alkylene group, $C_{2-6}$ alkenylene group or $C_{2-6}$ alkynylene group, which groups optionally include one or more heteroatoms or optionally one or more carbonyl groups (C=O) as links, which cycloaliphatic group can be condensed with an unsubstituted, monosubstituted or polysubstituted, monocyclic or polycyclic ring system, or an unsubstituted, monosubstituted or polysubstituted five-membered or six-membered aryl group or heteroaryl group optionally bonded via an unsubstituted, monosubstituted or polysubstituted $C_{1-6}$ alkylene, $C_{2-6}$ alkenylene or $C_{2-6}$ alkynylene group, which groups optionally include one or more heteroatoms as links, which aryl or heteroaryl group can be condensed with an unsubstituted, monosubstituted or polysubstituted, monocyclic or polycyclic ring system.

16. A compound according to claim 15, wherein:

X represents a hydrogen atom or a methyl group;

R$^8$ represents:

a C$_{1-3}$ alkyl group optionally substituted by a di-(C$_{1-3}$ alkyl)amino group, or for an unsubstituted, monosubstituted or polysubstituted phenyl group, or for an unsubstituted, monosubstituted or polysubstituted naphthyl group, or for an unsubstituted, monosubstituted or polysubstituted pyridynyl group, or for an unsubstituted, monosubstituted or polysubstituted furanyl group, or an unsubstituted, monosubstituted or polysubstituted thiophenyl group, or for an unsubstituted, monosubstituted or polysubstituted pyrroldynyl group, or for an unsubstituted, monosubstituted or polysubstituted benzo[1,3]dioxolyl group, or for an unsubstituted, monosubstituted or polysubstituted benzofuranyl group, which cyclic groups can be independently bonded via a C$_{1-3}$ alkylene group, or a C$_{2-3}$ alkenylene group, which groups optionally include a carbonyl group (C=O) as link and/or may be monosubstituted or polysubstituted by the same or different substituents selected from the group consisting of —(C=O)—C$_{1-3}$ alkyl, C$_{1-3}$ alkoxy, C$_{1-3}$ alkyl, F, Cl, Br, —CN, CF$_3$, CF$_2$H, and CFH$_2$;

R$^9$ represents a linear or branched C$_{1-3}$ alkyl group, and

R$^{10}$ represents a pyrrolidynyl group bonded via a C$_{1-2}$ alkylene group.

17. A compound according to claim 1, wherein:

R$^1$ represents a group —NR$^3$R$^4$ or a group —NR$^5$R$^6$;

R$^2$ represents a linear or branched C$_{1-5}$ alkyl group, or a linear or branched C$_{2-5}$ alkenyl group, or a cyclohexyl group optionally bonded via a —(CH$_2$) group, or a 1-naphthyl group or 2-naphthyl group optionally bonded via a —(CH$_2$) group or —(CH=CH) group, or a 2-furanyl group or 3-furanyl group optionally bonded via a —(CH$_2$) group or —(CH=CH) group, or a 2-thienyl group or 3-thienyl group optionally bonded via a —(CH$_2$)group or —(CH=CH) group, or an unsubstituted or at least monosubstituted phenyl group optionally bonded via a —(CH$_2$) group, —(CH$_2$)$_2$ group, —C(H)—(CH$_3$) group or —(CH$_2$)—O group, wherein any substituents are independently selected from the group consisting of —F, —Cl, —Br, —OCH$_3$, —OC$_2$H$_5$, CH$_3$, and C$_2$H$_5$;

R$^3$ represents a hydrogen atom or a methyl group;

R$^4$ represents:

a linear or branched, unsubstituted, monosubstituted or polysubstituted (C$_{1-3}$ alkyl group, or a cycloaliphatic group bonded via a C$_{1-3}$ alkylene group selected from the group consisting of

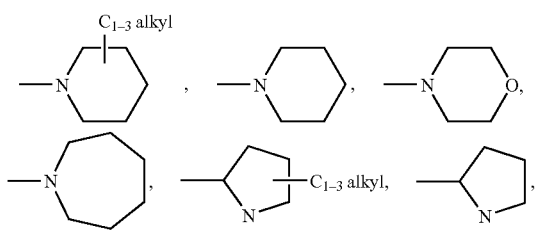

-continued

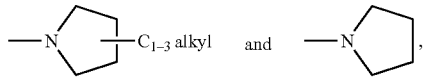

a cycloaliphatic group corresponding to the formula

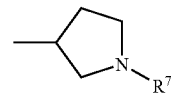

wherein R$^7$ represents a phenyl group or benzofuranyl group bonded via a methylene group and optionally independently monosubstituted or polysubstituted by the same or different substituents selected from the group consisting of F, Cl, Br, CF$_3$, CHF$_2$, CH$_2$F, phenoxy, benzyloxy, phenyl, C$_{1-4}$ alkoxy and C$_{1-4}$ alkylthio, or a phenyl group optionally bonded via a methylene group, which phenyl group can be monosubstituted or polysubstituted by the same or different substituent selected from the group consisting of di-(C$_{1-3}$)alkylamino, C$_{1-3}$ methoxy, and morpholinyl;

R$^5$ and R$^6$ together with the nitrogen atom to which they are bonded form a group selected from the group consisting of:

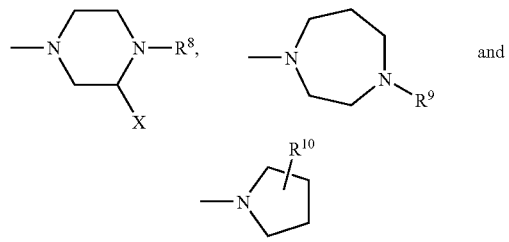

wherein

X represents a hydrogen atom or a methyl group;

R$^8$ represents a linear or branched C$_{1-3}$ alkyl group optionally substituted by a dimethylamino group, or an unsubstituted, monosubstituted or polysubstituted cyclic group selected from the group consisting of phenyl, naphthyl, pyridynyl, furanyl, thiophenyl, pyrroldynyl, benzo[1,3]dioxolyl and benzofuranyl; said cyclic group being independently bonded via a C$_{1-3}$ alkylene group or a C$_{2-3}$ alkenylene group, which groups optionally include a carbonyl group (C=O) as link and/or can be monosubstituted or polysubstituted by the same or different substituents selected from the group consisting of —(C=O)C$_{1-3}$ alkyl, C$_{1-3}$ alkoxy, F, Cl, Br, —CN, CF$_3$, CF$_2$H, and CFH$_2$;

R$^9$ represents a methyl group or ethyl group, and

R$^{10}$ represents a pyrrolidynyl group bonded via a —(CH$_2$) group.

18. A compound according to claim 1, wherein:

R$^1$ represents a group —NR$^3$R$^4$ or a group —NR$^5$R$^6$; R$^2$ represents:

a linear or branched, saturated or unsaturated, optionally substituted C$_{1-10}$ aliphatic group; or an unsaturated or saturated, optionally substituted 3-membered, 4-membered, 5-membered, 6-membered, 7-membered, 8-membered, or 9-membered cycloaliphatic group, which can be bonded via a linear or branched, optionally substituted $C_{1-5}$ alkylene group, $C_{2-5}$ alkenylene group or $C_{2-5}$ alkynylene group, each of these groups optionally including 1 or 2 heteroatom(s) as link(s); or an optionally substituted 5-membered to 14-membered aryl group or heteroaryl group, which can be bonded via a linear or branched, optionally substituted $C_{1-5}$ alkylene group, $C_{2-5}$ alkenylene group, or $C_{2-5}$ alkynylene group, which groups optionally include 1 or 2 heteroatom(s) as link(s);

$R_3$ represents:

a hydrogen atom or a linear or branched, saturated or unsaturated, optionally substituted $C_{1-10}$ aliphatic group; or an unsaturated or saturated, optionally substituted three-membered, four-membered, five-membered, six-membered, seven-membered, eight-membered, or nine-membered cycloaliphatic group, which can be bonded via a linear or branched, optionally substituted $C_{1-5}$ alkylene group, $C_{2-5}$ alkenylene group or $C_{2-5}$ alkynylene group which groups optionally include 1 or 2 heteroatom(s) as link(s); or an optionally substituted five-membered to fourteen-membered aryl group or heteroaryl group, which can be bonded via a linear or branched, optionally substituted $C_{1-5}$ alkylene group, $C_{2-5}$ alkenylene group or $C_{2-5}$ alkynylene group which groups optionally include 1 or 2 heteroatom(s) as link(s);

$R_5$ and $R_6$ together with the nitrogen atom to which they are bonded form a saturated or unsaturated, optionally substituted four-membered, five-membered, six-membered, seven-membered, eight-membered or nine-membered heterocycloaliphatic group, and each of said heterocycloaliphatic groups optionally being substituted by a group $R^8$ and optionally by a group X or a group $R^9$ or a group $R^{10}$, and optionally having 1, 2, or 3 further heteroatom(s) selected independently from the group consisting of oxygen, nitrogen, and sulfur as ring member(s);

wherein

X represents a linear or branched, saturated or unsaturated $C_{1-10}$ aliphatic group;

$R^8$, $R^9$, and $R^{10}$ each independently represent:

a linear or branched, saturated or unsaturated, optionally substituted $C_{1-10}$ aliphatic racial; or an unsaturated or saturated, optionally substituted three-membered, four-membered, five-membered, six-membered, seven-membered, eight-membered or nine-membered cycloaliphatic group, wherein said cycloaliphatic group optionally can be bonded via a linear or branched, optionally substituted $C_{1-5}$ alkylene group, $C_{2-5}$ alkenylene group or $C_{2-5}$ alkynylene group, which groups optionally include 1 or 2 heteroatom(s) or a carbonyl group (C=O) as link(s); said cycloaliphatic group optionally can be condensed with a saturated, unsaturated or aromatic, optionally substituted mono or polycyclic ring system; and said cycloaliphatic group optionally can include 1, 2, or 3 heteroatom(s) independently selected from the group consisting of oxygen, nitrogen, and sulfur; or an optionally substituted five-membered to fourteen-membered aryl group or heteroaryl group; wherein said aryl or heteroaryl group optionally can be bonded via a linear or branched, optionally substituted $C_{1-5}$ alkylene group, $C_{2-5}$ alkenylene group or $C_{2-5}$ alkynylene group, which groups optionally may include 1 or 2 heteroatom(s) or a carbonyl group (C=O) as link(s), and said aryl or heteroaryl group optionally can be condensed with a saturated or unsaturated, optionally substituted monocyclic or polycyclic ring system;

wherein:

any of said $C_{1-10}$ aliphatic groups optionally can be substituted by 1, 2, 3, 4, or 5 substituents independently selected from the group consisting of F, Cl, Br, —CN, —$NO_2$, hydroxy, $C_{1-6}$ alkoxy, —$NH_2$, —NH-($C_{1-3}$ alkyl), —N($C_{1-3}$ alkyl)-($C_{1-3}$ alkyl), —NH-phenyl, —N($C_{1-3}$ alkyl)-phenyl, and —N(phenyl)$_2$;

any of said said cycloaliphatic groups optionally can be substituted by 1, 2, 3, 4, or 5 substituents independently selected from the group consisting of F, Cl, Br, —CN, —$CF_3$, —$CHF_2$, —$CH_2F$, hydroxy, —$C_{1-6}$ alkoxy, —$NH_2$, —NH—($C_{1-3}$ alkyl), —N($C_{1-3}$ alkyl)-($C_{1-3}$ alkyl), —NH-phenyl, —N($C_{1-3}$ alkyl)-phenyl, —N(phenyl)$_2$, SH, —$C_{1-6}$ alkylthio, —$C_{1-6}$ alkyl, —($CH_2$)benzo[b]furanyl, phenoxy, benzyloxy, phenyl, and benzyl; wherein the cyclic moiety of the groups phenoxy, benzyloxy, phenyl, —($CH_2$)benzo[b]furanyl and benzyl optionally can be substituted by 1, 2, 3, 4, or 5 substituents independently selected from the group consisting of F, Cl, Br, —$C_{14}$ alkyl, —$CF_3$, —$CHF_2$, —$CH_2F$, —$C_{1-4}$ alkoxy, —$C_{1-4}$ alkylthio, phenoxy, phenyl, and benzyloxy;

any of said $C_{1-5}$ alkylene groups, $C_{2-5}$ alkenylene groups or $C_{2-5}$ alkynylene groups optionally can be substituted by 1, 2, 3, 4, or 5 substituents independently selected from the group consisting of F, Cl, Br, —CN, —$NO_2$, hydroxy, $C_{1-6}$ alkoxy, —$NH_2$, —NH—($C_{1-3}$ alkyl), —N($C_{1-3}$ alkyl)-($C_{1-3}$ alkyl), —NH-phenyl, —N($C_{1-3}$ alkyl)-phenyl, N(phenyl)$_2$, and phenyl, and said $C_{1-5}$ alkylene groups, $C_{2-5}$ alkenylene groups or $C_{2-5}$ alkynylene groups optionally can include 1 or 2 heteroatom(s) independently selected from the group consisting of oxygen, nitrogen, and sulfur;

any of said aryl or heteroaryl groups optionally can be substituted by 1, 2, 3, 4, or 5 substituents independently selected from the group consisting of F, Cl, Br, —CN, —$CF_3$, —$CHF_2$) —$CH_2F$, hydroxy, —$C_{1-6}$ alkoxy, —O—$CF_3$, —S—$CF_3$, SH, —$C_{1-6}$ alkylthio, —$C_{1-6}$ alkyl, —$NH_2$, —NH—($C_{1-3}$ alkyl), —N($C_{1-3}$ alkyl)-($C_{1-3}$ alkyl), —NH-phenyl, —N($C_{1-3}$ alkyl)-phenyl, N(phenyl)$_2$, phenoxy, benzyloxy, phenyl, benzyl, and morpholynyl; wherein the cyclic moiety of the groups phenoxy, benzyloxy, phenyl, and benzyl optionally can be substituted by 1, 2, 3, 4, or 5 substituents independently selected from the group consisting of F, Cl, Br, hydroxy, —$CF_3$, —$SF_5$, —CN, —$NO_2$, —$C_{1-6}$ alkoxy, —O—$CF_3$, —S—$CF_3$, phenyl, and benzyloxy;

any of said heteroaryl groups optionally can include as ring members 1, 2, 3, 4, or 5 heteroatom(s) independently selected from the group consisting of oxygen, nitrogen, and sulfur;

the rings of any of said monocyclic or polycyclic ring systems optionally can be substituted by 1, 2, 3, 4, or 5 substituents independently selected from the group consisting of F, Cl, Br, —CN, —$CF_3$, —$CHF_2$, —$CH_2F$, hydroxy, $C_{1-6}$ alkoxy, —O—$CF_3$, —S—$CF_3$, SH, —$C_{1-6}$ alkylthio, —$C_{1-6}$ alkyl, —$NH_2$, —NH-($C_{1-3}$ alkyl), —N($C_{1-3}$ alkyl)-($C_{1-3}$ alkyl), —NH-phenyl, —N($C_{1-3}$ alkyl)-phenyl, N(phenyl)$_2$, phenoxy, benzyloxy, phenyl, benzyl, and morpholynyl; wherein the cyclic moiety of the groups phenoxy, benzyloxy, phenyl, and benzyl optionally can be substituted by 1, 2, 3, 4, or 5 substituents independently selected from the group consisting of F, Cl, Br, hydroxy, —$CF_3$, —$SF_5$, —CN, —$NO_2$, —$C_{1-6}$ alkoxy, —O—$CF_3$, —S—$CF_3$, phenyl, and benzyloxy; and the rings of each of said monocyclic or polycyclic ring systems are five-membered, six-membered, or seven-membered rings and optionally can include as ring members 1, 2, 3, 4, or 5 heteroatom(s) independently selected from the group consisting of oxygen, nitrogen, and sulfur.

19. A compound according to claim 1, wherein $R^2$ represents:

an alkyl group selected from the group consisting of methyl, ethyl, n-propyl, isopropyl, n-butyl, sec-butyl, isobutyl, tert-butyl, n-pentyl, sec-pentyl, (1,1)-dimethylpropyl, and n-hexyl; said alkyl group optionally being substituted by 1, 2, 3, 4, or 5 substituents independently selected from the group consisting of F, Cl, Br, —CN, —$NO_2$, hydroxy, $C_{1-6}$ alkoxy, —$NH_2$, —NH—($C_{1-3}$ alkyl), —N($C_{1-3}$ alkyl)-($C_{1-3}$ alkyl), —NH-phenyl, —N($C_{1-3}$ alkyl)-phenyl, and —N(phenyl)$_2$; or an alkenyl group selected from the group consisting of vinyl, 1-propenyl, 2-propenyl, 1-butenyl, 2-butenyl, 3-butenyl, 1-pentenyl, 2-pentenyl, and pent-1,3-dienyl; said alkenyl group optionally being substituted by 1, 2, 3, 4, or 5 substituents independently selected from the group consisting of F, Cl, Br, —CN, —$NO_2$, hydroxy, $C_{1-6}$ alkoxy, —$NH_2$, —NH—($C_{1-3}$ alkyl), —N($C_{1-3}$ alkyl)-($C_{1-3}$ alkyl), —NH-phenyl, —N($C_{1-3}$ alkyl)-phenyl, and —N(phenyl)$_2$; or a (hetero)cycloaliphatic group selected from the group consisting of cyclopropyl, cyclobutyl, cyclopentyl, cyclohexyl, cycloheptyl, cyclopentenyl, cyclohexenyl, cycloheptenyl, imidazolidynyl, tetrahydrofuranyl, tetrahydrothiophenyl, pyrrolidynyl, piperidynyl, morpholynyl, piperazynyl, thiomorpholynyl, tetrahydropyranyl, azepanyl, diazepanyl, and dithiolanyl; said (hetero)cycloaliphatic group optionally being bonded via a linear or branched, unsubstituted $C_{1-5}$ alkylene group, and said (hetero)cycloaliphatic group optionally being substituted by 1, 2, 3, 4, or 5 substituents independently selected from the group consisting of F, Cl, Br, —CN, —$CF_3$, —$CHF_2$, —$CH_2F$, hydroxy, —$C_{1-6}$ alkoxy, —$NH_2$, —NH—($C_{1-3}$ alkyl), —N($C_{1-3}$ alkyl)-($C_{1-3}$ alkyl), —NH-phenyl, —N($C_{1-3}$ alkyl)-phenyl, —N(phenyl)$_2$, SH, —$C_{1-6}$ alkylthio, —$C_{1-6}$ alkyl, —($CH_2$)benzo[b]furanyl, phenoxy, benzyloxy, phenyl, and benzyl; wherein the cyclic moiety of the phenoxy, benzyloxy, phenyl, —($CH_2$)benzo[b]furanyl, and benzyl substituents optionally may be substituted by 1, 2, 3, 4, or 5 substituents independently selected from the group consisting of F, Cl, Br, —$C_{1-4}$ alkyl, —$CF_3$, —$CHF_2$, —$CH_2F$, —$C_{1-4}$ alkoxy, —$C_{1-4}$ alkylthio, phenoxy, phenyl, and benzyloxy; or a group selected from the group consisting of phenyl, naphthyl, thiophenyl, furanyl, pyrrolyl, pyrazolyl, pyrazynyl, pyranyl, triazolyl, pyridynyl, imidazolyl, indolyl, isoindolyl, benzo[b]furanyl, benzo[b]thiophenyl, thiazolyl, oxazolyl, isoxazolyl, pyridazynyl, pyrazynyl, pyrimidynyl, indazolyl, quinazolynyl, quinolynyl, and isoquinolynyl; said group optionally being bonded via a linear or branched, unsubstituted, $C_{1-5}$ alkylene group or $C_{2-5}$ alkenylene group, which groups optionally may include an oxygen atom as link, and said group optionally being substituted by 1, 2, 3, 4, or 5 substituents independently selected from the group consisting of F, Cl, Br, —CN, —$CF_3$, —$CHF_2$, —$CH_2F$, hydroxy, —$C_{1-6}$ alkoxy, —O—$CF_3$, —S—$CF_3$, SH, —$C_{1-6}$ alkylthio, —$C_{1-6}$ alkyl, —$NH_2$, —NH—($C_{1-3}$ alkyl), —N($C_{1-3}$ alkyl)-($C_{1-3}$ alkyl), —NH-phenyl, —N($C_{1-3}$ alkyl)-phenyl, N(phenyl)$_2$, phenoxy, benzyloxy, phenyl, benzyl, and morpholynyl; wherein the cyclic moiety of the phenoxy, benzyloxy, phenyl, and benzyl substituents optionally can be substituted by 1, 2, 3, 4, or 5 substituents independently selected from the group consisting of F, Cl, Br, hydroxy, —$CF_3$, —$SF_5$, —CN, —$NO_2$, —$C_{1-6}$ alkoxy, —O—$CF_3$, —S—$CF_3$, phenyl, and benzyloxy.

20. A compound according to claim 19, wherein $R^2$ represents:

an alkyl group selected from the group consisting of methyl, ethyl, n-propyl, isopropyl, n-butyl, sec-butyl, isobutyl, tert-butyl, n-pentyl, sec-pentyl, (1,1)-dimethylpropyl, and n-hexyl; or an alkenyl group selected from the group consisting of vinyl, 1-propenyl, 2-propenyl, 1-butenyl, 2-butenyl, 3-butenyl, 1-pentenyl, 2-pentenyl, and pent-1,3-dienyl; or a cycloaliphatic group selected from the group consisting of cyclopropyl, cyclobutyl, cyclopentyl, cyclohexyl, cycloheptyl, cyclopentenyl, cyclohexenyl, and cycloheptenyl; said cycloaliphatic group optionally being bonded via a —($CH_2$) group, —($CH_2$)$_2$ group, —CH($CH_3$) group, or —($CH_2$)$_3$ group, and said cycloaliphatic group optionally being substituted by 1, 2, 3, 4, or 5 substituents independently selected from the group consisting of F, Cl, Br, —CN, —$CF_3$, —$CHF_2$, —$CH_2F$, hydroxy, —O—$CH_3$, —O—$C_2H_5$, —O—$C_3H_7$, —$NH_2$, —NH—$CH_3$, —NH—$C_2H_5$, —N—($CH_3$)$_2$, —N($C_2H_5$)$_2$, —N($CH_3$)—($C_2H_5$), —NH-phenyl, —N($CH_3$)-phenyl, —N($C_2H_5$)-phenyl, —N(phenyl)$_2$, SH, —S—$CH_3$, —S—$C_2H_5$, —S—$C_3H_7$, —S—C($CH_3$)$_3$, methyl, ethyl, n-propyl, isopropyl, n-butyl, sec-butyl, and tert-butyl; or a group selected from the group consisting of phenyl, 1-naphthyl, 2-naphthyl, 2-furanyl, 3-furanyl, 2-thiophenyl, or 3-thiophenyl; said group optionally being bonded via a —($CH_2$) group, —($CH_2$)$_2$ group, —($CH_2$)—O group, —CH($CH_3$) group, —(CH=CH) group, or —($CH_2$)$_3$ group, and said group optionally being substituted by 1, 2, 3, 4, or 5 substituents independently selected from the group consisting of F, Cl, Br, —CN, —$CF_3$, —$CHF_2$, —$CH_2F$, hydroxy, —O—$CH_3$, —O—$C_2H_5$, —O—$C_3H_7$, —O—$CF_3$, —S—$CF_3$, —SH, —S—$CH_3$, —S—$C_2H_5$, —S—$C_3H_7$, —S—C($CH_3$)$_3$, methyl, ethyl, n-propyl, isopropyl, n-butyl, sec-butyl, tert-butyl, —$NH_2$, —NH—$CH_3$, —NH—$C_2H_5$, —N—($CH_3$)$_2$, —N($C_2H_5$)$_2$, —N($CH_3$)—($C_2H_5$), —NH-phenyl, —N($CH_3$)-phenyl, —N($C_2H_5$)-phenyl, —N(phenyl)$_2$, phenoxy, benzyloxy, phenyl, benzyl, and morpholynyl.

21. A compound according to claim 20, wherein $R^2$ represents:

an alkyl group selected from the group consisting of n-propyl, isopropyl, n-butyl, sec-butyl, isobutyl, tert-butyl, n-pentyl, sec-pentyl, and (1,1)-dimethylpropyl; or an alkenyl group selected from the group consisting of 1-pentenyl, 2-pentenyl and pent-1,3-dienyl; or a cycloaliphatic group selected from the group consisting of cyclopentyl, cyclohexyl, and cycloheptyl, which is bonded via a —($CH_2$) group; or a group selected from the group consisting of phenyl, 1-naphthyl, 2-naphthyl, 2-furanyl, 3-furanyl, 2-thiophenyl, and 3-thiophenyl; said group optionally being bonded via a —(CH$_2$) group, —(CH$_2$)$_2$ group, —(CH$_2$)—O group, —CH(CH$_3$) group, —(CH═CH) group, or —(CH$_2$)$_3$ group, and said group optionally being substituted by 1, 2, or 3 substituents independently selected from the group consisting of F, Cl, Br, —O—CH$_3$, —O—C$_2$H$_5$, methyl, ethyl, n-propyl, and isopropyl.

22. A compound according to claim 1, wherein R$^3$ represents:

a hydrogen atom, or an alkyl group selected from the group consisting of methyl, ethyl, n-propyl, isopropyl, n-butyl, sec-butyl, isobutyl, tert-butyl, n-pentyl, sec-pentyl, (1,1)-dimethylpropyl, and n-hexyl; said alkyl group optionally being substituted by 1, 2, 3, 4, or 5 substituents independently selected from the group consisting of F, Cl, Br, —CN, —NO$_2$, hydroxy, C$_{1-6}$ alkoxy, —NH$_2$, —NH—(C$_{1-3}$ alkyl), —N(C$_{1-3}$ alkyl)-(C$_{1-13}$ alkyl), —NH-phenyl, —N(C$_{1-3}$ alkyl)-phenyl, and —N(phenyl)$_2$; or a (hetero)cycloaliphatic group selected from the group consisting of cyclopropyl, cyclobutyl, cyclopentyl, cyclohexyl, cycloheptyl, cyclopentenyl, cyclohexenyl, cycloheptenyl, imidazolidynyl, tetrahydrofuranyl, tetrahydrothiophenyl, pyrrolidynyl, piperidynyl, morpholynyl, piperazynyl, thiomorpholynyl, tetrahydropyranyl, azepanyl, diazepanyl, and dithiolanyl; said (hetero)cycloaliphatic group optionally being bonded via a linear or branched, unsubstituted C$_{1-5}$ alkylene group, and said (hetero)cycloaliphatic group optionally being substituted by 1, 2, 3, 4, or 5 substituents independently selected from the group consisting of F, Cl, Br, —CN, —CF$_3$, —CHF$_2$, —CH$_2$F, hydroxy, —C$_{1-6}$ alkoxy, —NH$_2$, —NH—(C$_{1-3}$ alkyl), —N(C$_{1-3}$ alkyl)—(C$_{1-3}$ alkyl), —NH-phenyl, —N(C$_{1-3}$ alkyl)-phenyl, —N(phenyl)$_2$, —SH, —C$_{1-6}$ alkylthio, —C$_{1-6}$ alkyl, —(CH$_2$)benzo[b]furanyl, phenoxy, benzyloxy, phenyl, and benzyl; wherein the cyclic moiety of the phenoxy, benzyloxy, phenyl, —(CH$_2$)benzo[b]furanyl and benzyl substituents can be substituted by 1, 2, 3, 4, or 5 substituents independently selected from the group consisting of F, Cl, Br, —C$_{1-4}$ alkyl, —CF$_3$, —CHF$_2$, —CH$_2$F, —C$_{1-4}$ alkoxy, —C$_{1-4}$ alkylthio, phenoxy, phenyl, and benzyloxy; or a group selected from the group consisting of phenyl, naphthyl, thiophenyl, furanyl, pyrrolyl, pyrazolyl, pyrazynyl, pyranyl, triazolyl, pyridynyl, imidazolyl, indolyl, isoindolyl, benzo[b]furanyl, benzo[b]thiophenyl, thiazolyl, oxazolyl, isoxazolyl, pyridazynyl, pyrazynyl, pyrimidynyl, indazolyl, quinazolynyl, quinolynyl, and isoquinolynyl; said group optionally being bonded via a linear or branched, unsubstituted, C$_{1-5}$ alkylene group or C$_{2-5}$ alkenylene group, which groups optionally include an oxygen atom as link, and said group optionally being substituted by 1, 2, 3, 4, or 5 substituents independently selected from the group consisting of F, Cl, Br, —CN, —CF$_3$, —CHF$_2$, —CH$_2$F, hydroxy, —C$_{1-6}$ alkoxy, —O—CF$_3$, —S—CF$_3$, —SH, —C$_{1-6}$ alkylthio, —C$_{1-6}$ alkyl, —NH$_2$, —NH—(C$_{1-3}$ alkyl), —N(C$_{1-3}$ alkyl)-(C$_{1-3}$ alkyl), —NH-phenyl, —N(C$_{1-3}$ alkyl)-phenyl, N(phenyl)$_2$, phenoxy, benzyloxy, phenyl, benzyl, and morpholynyl; wherein the cyclic moiety of the phenoxy, benzyloxy, phenyl, and benzyl substituents optionally may be substituted by 1, 2, 3, 4, or 5 substituents independently selected from the group consisting of F, Cl, Br, hydroxy, —CF$_3$, —SF$_5$, —CN, —NO$_2$, —C$_{1-6}$ alkoxy, —O—CF$_3$, —S—CF$_3$) phenyl, and benzyloxy.

23. A compound according to claim 22, wherein R$^3$ represents:

a hydrogen atom, or an alkyl group selected from the group consisting of methyl, ethyl, n-propyl, n-butyl and n-pentyl; said alkyl group optionally being substituted by 1 or 2 substituents independently selected from the group consisting of NH$_2$, —NH—CH$_3$, —NH—C$_2$H$_5$, —N—(CH$_3$)$_2$, —N(C$_2$H$_5$)$_2$, —N(CH$_3$) (C$_2$H$_5$), —NH-phenyl, —N(CH$_3$)-phenyl, —N(C$_2$H$_5$)-phenyl, and —N(phenyl)$_2$; or a group selected from the group consisting of

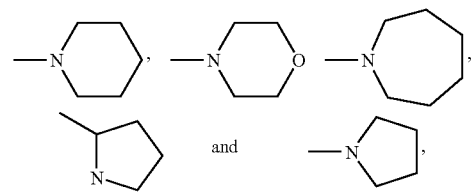

said group optionally being bonded via a —(CH$_2$) group, —(CH$_2$)$_2$ group, —(CH$_2$)—O group, —CH(CH3) group, —(CH═CH) group, or —(CH$_2$)$_3$ group, and said group optionally being substituted by 1, 2, or 3 substituents independently selected from the group consisting of methyl, ethyl, and n-propyl; or a group corresponding to the formula

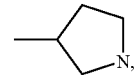

said group optionally being substituted on the nitrogen atom by a substituent selected from the group consisting of —(CH$_2$)benzo[b]furanyl and benzyl; wherein the cyclic moiety of the —(CH$_2$)benzo[b]furanyl and benzyl groups optionally may be substituted by 1, 2, 3, 4 or 5 substituents independently selected from the group consisting of F, Cl, Br, —C$_{1-4}$ alkyl, —CF$_3$, —CHF$_2$, —CH$_2$F, —C$_{1-4}$ alkoxy, —C$_{1-4}$ alkylthio, phenoxy, phenyl, and benzyloxy; or a group selected from the group consisting of phenyl and naphthyl, which group can in each case be bonded via a —(CH$_2$) group, —(CH$_2$)$_2$ group, or —(CH$_2$)$_3$ group and/or can be substituted by 1, 2, or 3 substituents independently selected from the group consisting of —C$_{1-6}$ alkoxy, —C$_{1-6}$ alkyl, —NH$_2$, —NH—(C$_{1-3}$ alkyl), —N(C$_{1-3}$ alkyl)-(C$_{1-3}$ alkyl), —NH-phenyl, —N(C$_{1-3}$ alkyl)-phenyl, N(phenyl)$_2$, and morpholynyl.

24. A compound according to claim 23, wherein R$^3$ represents:

a hydrogen atom, or a group selected from the group consisting of methyl, ethyl, n-propyl, —(CH$_2$)—N(CH$_3$)$_2$, —(CH$_2$)—(CH$_2$)—N(CH$_3$)$_2$, —(CH$_2$)—(CH$_2$)—(CH$_2$)—N(CH$_3$)$_2$, —(CH$_2$)—(CH$_2$)—N(C$_2$H$_5$)$_2$, —(CH$_2$)—(CH$_2$)—(CH$_2$)—N(C$_2$H$_5$)$_2$, —(CH$_2$)—(CH$_2$)—N(CH$_3$)-(phenyl), and —(CH$_2$)—(CH$_2$)—(CH$_2$)—N(CH$_3$)-(phenyl); or a group selected from the group consisting of

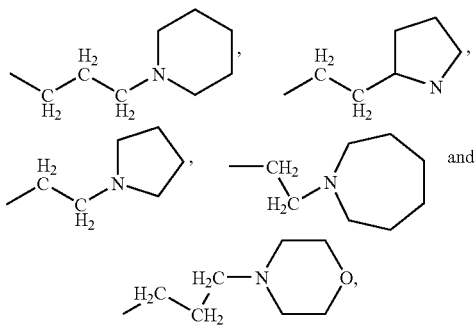

optionally substituted by a methyl group; or
a group corresponding to the formula

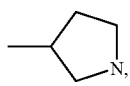

optionally substituted on the nitrogen atom by a substituent selected from the group consisting of —(CH$_2$)benzo[b]furanyl and benzyl; wherein the cyclic moiety of the —(CH$_2$)benzo[b]furanyl and benzyl substituents optionally may be substituted by 1, 2, or 3 substituents independently selected from the group consisting of F, Cl, Br, —O—CH$_3$, —O—C$_2$H$_5$, —O—C$_3$H$_7$, —S—CH$_3$, —S—C$_2$H$_5$, —S—C$_3$H$_7$, —S—C(CH$_3$)$_3$, methyl, ethyl, n-propyl, isopropyl, n-butyl, phenoxy and benzyloxy; or a group selected from the group consisting of phenyl and benzyl; wherein the cyclic moiety of the phenyl and benzyl groups can be substituted by 1, 2, or 3 substituents independently selected from the group consisting of —O—CH$_3$, —O—C$_2$H$_5$, —O—C$_3$H$_7$, —N—(CH$_3$)$_2$, —N(C$_2$H$_5$)$_2$ and morpholynyl.

25. A compound according to claim 24, wherein R$^3$ represents a hydrogen atom or a methyl group.

26. A compound according to claim 1, wherein R$^4$ represents:

a hydrogen atom, or an alkyl group selected from the group consisting of methyl, ethyl, n-propyl, isopropyl, n-butyl, sec-butyl, isobutyl, tert-butyl, n-pentyl, sec-pentyl, (1,1)-dimethylpropyl, and n-hexyl; said alkyl group optionally being substituted by 1, 2, 3, 4 or 5 substituents independently selected from the group consisting of F, Cl, Br, —CN, —NO$_2$, hydroxy, C$_{1-6}$ alkoxy, —NH$_2$, —NH—(C$_{1-3}$ alkyl), —N(C$_{1-3}$ alkyl)-(C$_{1-3}$ alkyl), —NH-phenyl, —N(C$_{1-3}$ alkyl)-phenyl, and —N(phenyl)$_2$; or an alkenyl group selected from the group consisting of vinyl, 1-propenyl, 2-propenyl, 1-butenyl, 2-butenyl, 3-butenyl, 1-pentenyl, 2-pentenyl, and pent-1,3-dienyl; said alkenyl group optionally being substituted by 1, 2, 3, 4, or 5 substituents independently selected from the group consisting of F, Cl, Br, —CN, —NO$_2$, hydroxy, C$_{1-6}$ alkoxy, —NH$_2$, —NH—(C$_{1-3}$ alkyl), —N(C$_{1-3}$ alkyl)-(C$_{1-3}$ alkyl), —NH-phenyl, —N(C$_{1-3}$ alkyl)phenyl, and —N(phenyl)$_2$; or a (hetero)cycloaliphatic group selected from the group consisting of cyclopropyl, cyclobutyl, cyclopentyl, cyclohexyl, cycloheptyl, cyclopentenyl, cyclohexenyl, cycloheptenyl, imidazolidynyl, tetrahydrofuranyl, tetrahydrothiophenyl, pyrrolidynyl, piperidynyl, morpholynyl, piperazynyl, thiomorpholynyl, tetrahydropyranyl, azepanyl, diazepanyl, and dithiolanyl; said (hetero)cycloaliphatic group optionally being bonded via a linear or branched, unsubstituted C$_{1-5}$ alkylene group, and said (hetero)cycloaliphatic group optionally being substituted by 1, 2, 3, 4, or 5 substituents independently selected from the group consisting of F, Cl, Br, —CN, —CF$_3$, —CHF$_2$, —CH$_2$F, hydroxy, —C$_{1-6}$ alkoxy, —NH$_2$, —NH—(C$_{1-3}$ alkyl), —N(C$_{1-3}$ alkyl)-(C$_{1-3}$ alkyl), —NH-phenyl, —N(C$_{1-3}$ alkyl), phenyl, —N(phenyl)$_2$, —SH, —C$_{1-6}$ alkylthio, —C$_{1-6}$ alkyl, —(CH$_2$)benzo[b]furanyl, phenoxy, benzyloxy, phenyl, and benzyl; wherein the cyclic moiety of the phenoxy, benzyloxy, phenyl, —(CH$_2$)benzo[b]furanyl, and benzyl substituents can be substituted by 1, 2, 3, 4, or 5 substituents independently selected from the group consisting of F, Cl, Br, —C$_{1-4}$ alkyl, —CF$_3$, —CHF$_2$, —CH$_2$F, —C$_{1-4}$ alkoxy, —C$_{1-4}$ alkylthio, phenoxy, phenyl, and benzyloxy; or a group selected from the group consisting of phenyl, naphthyl, thiophenyl, furanyl, pyrrolyl, pyrazolyl, pyrazynyl, pyranyl, triazolyl, pyridynyl, imidazolyl, indolyl, isoindolyl, benzo[b]furanyl, benzo[b]thiophenyl, thiazolyl, oxazolyl, isoxazolyl, pyridazynyl, pyrazynyl, pyrimidynyl, indazolyl, quinazolynyl, quinolynyl, and isoquinolynyl; said group optionally being bonded via a linear or branched, unsubstituted C$_{1-5}$ alkylene group or C$_{2-5}$ alkenylene, which groups optionally include an oxygen atom as link, and said group optionally being substituted by 1, 2, 3, 4, or 5 substituents independently selected from the group consisting of F, Cl, Br, —CN, —CF$_3$, —CHF$_2$, —CH$_2$F, hydroxy, —C$_{1-6}$ alkoxy, —O—CF$_3$, —S—CF$_3$, —SH, —C$_{1-6}$ alkylthio, —C$_{1-6}$ alkyl, —NH$_2$, —NH—(C$_{1-3}$ alkyl), —N(C$_{1-3}$ alkyl)-(C$_{1-3}$ alkyl), —NH-phenyl, —N(C$_{1-3}$ alkyl)-phenyl, N(phenyl)$_2$, phenoxy, benzyloxy, phenyl, benzyl, and morpholynyl; wherein the cyclic moiety of the phenoxy, benzyloxy, phenyl, and benzyl substituents can be substituted by 1, 2, 3, 4, or 5 substituents independently selected from the group consisting of F, Cl, Br, hydroxy, —CF$_3$, —SF$_5$, —CN, —NO$_2$, —C$_{1-6}$ alkoxy, —O—CF$_3$, —S—CF$_3$, phenyl, and benzyloxy.

27. A compound according to claim 26, wherein R$^4$ represents:

a hydrogen atom, or an alkyl group selected from the group consisting of methyl, ethyl, n-propyl, n-butyl, and n-pentyl; said alkyl group optionally being substituted by 1 or 2 substituents independently selected from the group consisting of NH$_2$, —NH—CH$_3$, —NH—C$_2$H$_5$, —N—(CH$_3$)$_2$, —N(C$_2$H$_5$)$_2$, —N(CH$_3$)(C$_2$H$_5$), —NH-phenyl, —N(CH$_3$)-phenyl, —N(C$_2$H$_5$)-phenyl, and —N(phenyl)$_2$; or a group selected from the group consisting of

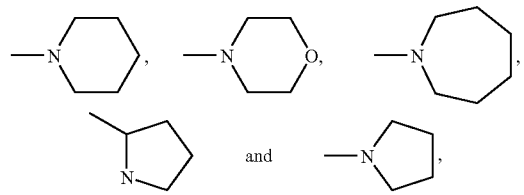

optionally bonded via a —(CH$_2$) group, —(CH$_2$)$_2$ group, —(CH$_2$)—O group, —CH(CH$_3$) group, —(CH═CH) group, or —(CH$_2$)$_3$ group, and optionally substituted by 1, 2, or 3 substituents independently selected from the group consisting of methyl, ethyl, and n-propyl; or a group corresponding to the formula

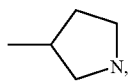

optionally substituted by a substituent selected from the group consisting of —(CH$_2$)benzo[b]furanyl and benzyl; wherein the cyclic moiety of the groups —(CH$_2$)benzo[b]furanyl and benzyl optionally can be substituted by 1, 2, 3, 4 or 5 substituents independently selected from the group consisting of F, Cl, Br, —C$_{1-4}$ alkyl, —CF$_3$, —CHF$_2$, —CH$_2$F, —C$_{1-4}$ alkoxy, —C$_{1-4}$ alkylthio, phenoxy, phenyl, and benzyloxy; or a group selected from the group consisting of phenyl and naphthyl; said group optionally being bonded via a —(CH$_2$) group, —(CH$_2$)$_2$ group, or —(CH$_2$)$_3$ group, and said group optionally being substituted by 1, 2, or 3 substituents independently selected from the group consisting of —C$_{1-6}$ alkoxy, —C$_{1-6}$ alkyl, —NH$_2$, —NH—(C$_{1-3}$ alkyl), —N(C$_{1-3}$ alkyl)-(C$_{1-3}$ alkyl), —NH-phenyl, —N(C$_{1-3}$ alkyl)-phenyl, N(phenyl)$_2$, and morpholynyl.

28. A compound according to claim 27, wherein R$^4$ represents:

a group selected from the group consisting of methyl, ethyl, n-propyl, —(CH$_2$)—N(CH$_3$)$_2$, —(CH$_2$)—(CH$_2$)—N(CH$_3$)$_2$—(CH$_2$)—(CH$_2$)—(CH$_2$)—N(CH$_3$)$_2$, —(CH$_2$)—(CH$_2$)—N(C$_2$H$_5$)$_2$, —(CH$_2$)—(CH$_2$)—(CH$_2$)—N(C$_2$H$_5$)$_2$, —(CH$_2$)—(CH$_2$)—N(CH$_3$)-(phenyl), and —(CH$_2$)—(CH$_2$)—(CH$_2$)—N(CH$_3$)-(phenyl); or a group selected from the group consisting of

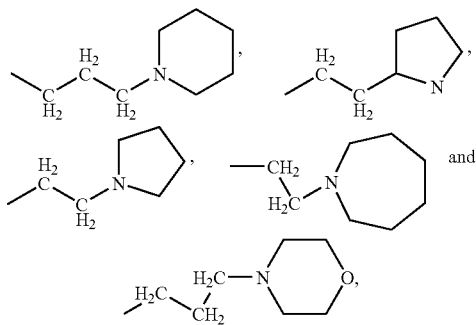

optionally substituted by a methyl group; or
a group corresponding to the formula

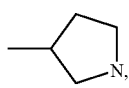

optionally substituted on the nitrogen atom by a substituent selected from the group consisting of —(CH$_2$)benzo[b]furanyl and benzyl; wherein the cyclic moiety of the —(CH$_2$)benzo[b]furanyl and benzyl groups optionally can be substituted by 1, 2, or 3 substituents independently selected from the group consisting of F, Cl, Br, —O—CH$_3$, —O—C$_2$H$_5$, —O—C$_3$H$_7$, —S—CH$_3$, —S—C$_2$H$_5$, —S—C$_3$H$_7$, —S—C(CH$_3$)$_3$, methyl, ethyl, n-propyl, isopropyl, n-butyl, phenoxy and benzyloxy; or a group selected from the group consisting of phenyl and benzyl; wherein the cyclic moiety of the phenyl and benzyl groups optionally can be substituted by 1, 2, or 3 substituents independently selected from the group consisting of —O—CH$_3$, —O—C$_2$H$_5$, —O—C$_3$H$_7$, —N—(CH$_3$)$_2$, —N(C$_2$H$_5$)$_2$, and morpholynyl.

29. A compound according to claim 1, wherein R$^5$ and R$^6$ together with the nitrogen atom to which they are attached form a heterocycloaliphatic group selected from the group consisting of piperazynyl, morpholynyl, thiomorpholynyl, pyrrolidynyl, azepanyl, diazepanyl, and piperidynyl; said heterocyclic group optionally being substituted by a group R$^8$, and optionally being substituted by a group X or a group R$^9$ or a group R$^{10}$.

30. A compound according to claim 29, wherein R$^5$ and R$^6$ together with the nitrogen atom to which they are attached form a group selected from the group consisting of:

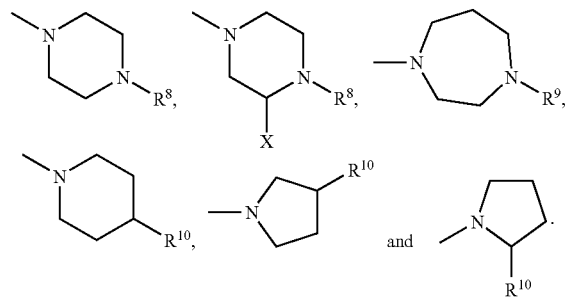

31. A compound according to claim 29, wherein X represents an alkyl group selected from the group consisting of methyl, ethyl, n-propyl, isopropyl, n-butyl, sec-butyl, isobutyl, tert-butyl, n-pentyl, sec-pentyl, (1,1)-dimethylpropyl, and n-hexyl.

32. A compound according to claim 29, wherein R$^8$, R$^9$, and R$^{10}$ each independently represent:

an alkyl group selected from the group consisting of methyl, ethyl, n-propyl, isopropyl, n-butyl, sec-butyl, isobutyl, tert-butyl, n-pentyl, sec-pentyl, (1,1)-dimethylpropyl, and n-hexyl; each said alkyl group optionally being substituted by 1, 2, 3, 4, or 5 substituents independently selected from the group consisting of F, Cl, Br, —CN, —NO$_2$, hydroxy, C$_{1-6}$ alkoxy, —NH$_2$, —NH—(C$_{1-3}$ alkyl), —N(C$_{1-3}$ alkyl)-(C$_{1-3}$ alkyl), —NH-phenyl, —N(C$_{1-3}$ alkyl)-phenyl, and —N(phenyl)$_2$; or an alkenyl group selected from the group consisting of vinyl, 1-propenyl, 2-propenyl, 1-butenyl, 2-butenyl, 3-butenyl, 1-pentenyl, 2-pentenyl, and pent-1,3-dienyl; each said alkenyl group optionally being substituted by 1, 2, 3, 4, or 5 substituents independently selected from the group consisting of F, Cl, Br, —CN, —NO$_2$, hydroxy, C$_{1-6}$ alkoxy, —NH$_2$, —NH—(C$_{1-3}$ alkyl), —N(C$_{1-3}$ alkyl)-(C$_{1-3}$ alkyl), —NH-phenyl, —N(C$_{1-3}$ alkyl)-phenyl, and —N(phenyl)$_2$; or a (hetero)cycloaliphatic group selected from the group consisting of cyclopropyl, cyclobutyl, cyclopentyl, cyclohexyl, cycloheptyl, cyclopentenyl, cyclohexenyl, cycloheptenyl, imidazolidynyl, tetrahydrofuranyl, tetrahydrothiophenyl, pyrrolidynyl, piperidynyl, morpholynyl, piperazynyl, thiomorpholynyl, tetrahydropyranyl, azepanyl, diazepanyl, and dithiolanyl; each said (hetero)cycloaliphatic group optionally being bonded via a linear or branched $C_{1-5}$ alkylene group optionally including a carbonyl group (C=O) as link, and each said (hetero)cycloaliphatic group optionally being substituted by 1, 2, 3, 4, or 5 substituents independently selected from the group consisting of F, Cl, Br, —CN, —$CF_3$, —$CHF_2$, —$CH_2F$, hydroxy, —$C_{1-6}$ alkoxy, —$NH_2$, —NH—($C_{1-3}$ alkyl), —N($C_{1-3}$ alkyl)-($C_{1-3}$ alkyl), —NH-phenyl, —N($C_{1-3}$ alkyl)-phenyl, —N(phenyl)$_2$, —SH, —$C_{1-6}$ alkylthio, —$C_{1-6}$ alkyl, —($CH_2$)benzo[b]furanyl, phenoxy, benzyloxy, phenyl, and benzyl; wherein the cyclic moiety of the groups phenoxy, benzyloxy, phenyl, —($CH_2$)benzo[b]furanyl, and benzyl optionally can be substituted by 1, 2, 3, 4, or 5 substituents independently selected from the group consisting of F, Cl, Br, —$C_{1-4}$ alkyl, —$CF_3$, —$CHF_2$, —$CH_2F$, —$C_{1-4}$ alkoxy, —$C_{1-4}$ alkylthio, phenoxy, phenyl, and benzyloxy; or a group selected from the group consisting of phenyl, naphthyl, (1,3)benzodioxolyl, (1,4)benzodioxanyl, thiophenyl, furanyl, pyrrolyl, pyrazolyl, pyrazinyl, pyranyl, triazolyl, pyridynyl, imidazolyl, indolyl, isoindolyl, benzo[b]furanyl, benzo[b]thiophenyl, thiazolyl, oxazolyl, isoxazolyl, pyridazynyl, pyrazynyl, pyrimidynyl, indazolyl, quinazolynyl, quinolynyl, and isoquinolynyl; each said group optionally being bonded via a linear or branched $C_{1-5}$ alkylene group or $C_{2-5}$ alkenylene group, optionally substituted by a phenyl group and optionally including a carbonyl group (C=O) as link; and each said group optionally being substituted by 1, 2, 3, 4, or 5 substituents independently selected from the group consisting of F, Cl, Br, —CN, —$CF_3$, —$CHF_2$, —$CH_2F$, hydroxy, —$C_{1-6}$ alkoxy, —O—$CF_3$, —S—$CF_3$, —SH, —$C_{1-6}$ alkylthio, —$C_{1-6}$ alkyl, —$NH_2$, —NH—($C_{1-3}$ alkyl), —N($C_{1-3}$ alkyl)-($C_{1-3}$ alkyl), —NH-phenyl, —N($C_{1-3}$ alkyl)-phenyl, N(phenyl)$_2$, phenoxy, benzyloxy, phenyl, benzyl, and morpholynyl; wherein the cyclic moiety of the groups phenoxy, benzyloxy, phenyl, and benzyl optionally can be substituted by 1, 2, 3, 4, or 5 substituents independently selected from the group consisting of F, Cl, Br, hydroxy, —$CF_3$, —$SF_5$, —CN, —$NO_2$, —$C_{1-6}$ alkoxy, —O—$CF_3$, —S—$CF_3$, phenyl, and benzyloxy.

33. A compound according to claim 32, wherein:
$R^8$ represents:
an alkyl group selected from the group consisting of methyl, ethyl, n-propyl, isopropyl, n-butyl, tert-butyl, and n-pentyl; each said alkyl group optionally being substituted by 1 or 2 substituents independently selected from the group consisting of $NH_2$, —NH—$CH_3$, —NH—$C_2H_5$, —N—$(CH_3)_2$, —N($C_2H_5$)$_2$, —N($CH_3$)($C_2H_5$), —NH-phenyl, —N($CH_3$)-phenyl, —N($C_2H_5$)-phenyl, and —N(phenyl)$_2$; or a cycloaliphatic group selected from the group consisting of pyrrolidynyl and piperidynyl; said cycloaliphatic group optionally being bonded via a —(C=O) group or a —($CH_2$)—(C=O) group; and said cycloaliphatic group optionally being substituted by 1, 2, 3, 4, or 5 substituents independently selected from the group consisting of F, Cl, Br, —CN, —$CF_3$, —$CHF_2$, —$CH_2F$, hydroxy, —O—$CH_3$, —O—$C_2H_5$, —O—$C_3H_7$, —$NH_2$, —NH—$CH_3$, —NH—$C_2H_5$, —N—$(CH_3)_2$, —N($C_2H_5$)$_2$, —N($CH_3$)($C_2H_5$), —NH-phenyl, —N($CH_3$)-phenyl, —N($C_2H_5$)-phenyl, —N(phenyl)$_2$, —SH, —S—$CH_3$, —S—$C_2H_5$, —S—$C_3H_7$, —S—C($CH_3$)$_3$, methyl, ethyl, n-propyl, isopropyl, n-butyl, sec-butyl, and tert-butyl; or a group selected from the group consisting of phenyl, 1-naphthyl, 2-naphthyl, 2-furanyl, 3-furanyl, 2-thiophenyl, 3-thiophenyl, 1-pyridynyl, 2-pyridynyl, 3-pyridynyl, benzo[b]furanyl, (1,3)benzodioxolyl, and (1,4)benzodioxanyl, which group can be bonded via a —(C=O) group, —($CH_2$) group, —($CH_2$)$_2$ group, —CH($CH_3$) group, —(CH=CH) group, —($CH_2$)—(C=O) group, —($CH_2$)—(CH=CH) group, or —($CH_2$)$_3$ group and/or can be substituted by 1, 2, 3, 4, or 5 substituents independently selected from the group consisting of F, Cl, Br, —CN, —$CF_3$, —$CHF_2$, —$CH_2F$, hydroxy, —O—$CH_3$, —O—$C_2H_5$, —O—$C_3H_7$, —O—$CF_3$, —S—$CF_3$, —SH, —S—$CH_3$, —S—$C_2H_5$, —S—$C_3H_7$, —S—C($CH_3$)$_3$, methyl, ethyl, n-propyl, isopropyl, n-butyl, sec-butyl, tert-butyl, —$NH_2$, —NH—$CH_3$, —NH—$C_2H_5$, —N—$(CH_3)_2$, —N($C_2H_5$)$_2$, —N($CH_3$)—($C_2H_5$), —NH-phenyl, —N($CH_3$)-phenyl, —N($C_2H_5$)-phenyl, —N(phenyl)$_2$, phenoxy, benzyloxy, phenyl, benzyl, and morpholynyl;

$R^9$ represents an alkyl group selected from the group consisting of methyl, ethyl, n-propyl, isopropyl, n-butyl, sec-butyl, isobutyl, tert-butyl, n-pentyl, sec-pentyl, (1,1)-dimethylpropyl, and n-hexyl; and $R^{10}$ represents
a cycloaliphatic group selected from the group consisting of pyrrolidynyl and piperidynyl, said cycloaliphatic group optionally being bonded via a —($CH_2$) group, —($CH_2$)$_2$ group, —CH($CH_3$) group, or —($CH_2$)$_3$ group, and said cycloaliphatic group optionally being substituted by 1, 2, 3, 4, or 5 substituents independently selected from the group consisting of F, Cl, Br, —CN, —$CF_3$, —$CHF_2$, —$CH_2F$, hydroxy, —O—$CH_3$, —O—$C_2H_5$, —O—$C_3H_7$, —$NH_2$, —NH—$CH_3$, —NH—$C_2H_5$, —N—$(CH_3)_2$, —N($C_2H_5$)$_2$, —N($CH_3$)—($C_2H_5$), —NH-phenyl, —N($CH_3$)phenyl, —N($C_2H_5$)phenyl, —N(phenyl)$_2$, —SH, —S—$CH_3$, —S—$C_2H_5$, —S—$C_3H_7$, —S—C($CH_3$)$_3$, methyl, ethyl, n-propyl, isopropyl, n-butyl, sec-butyl, and tert-butyl; or a group selected from the group consisting of phenyl, 1-naphthyl, and 2-naphthyl; said group optionally being bonded via a —($CH_2$) group, —[(CH)phenyl] group, —($CH_2$)$_2$ group, or —($CH_2$)$_3$ group, and said group optionally being substituted by 1, 2, 3, 4, or 5 substituents independently selected from the group consisting of F, Cl, Br, —CN, —$CF_3$, —$CHF_2$, —$CH_2F$, hydroxy, —O—$CH_3$, —O—$C_2H_5$, —O—$C_3H_7$, —O—$CF_3$, —S—$CF_3$, —SH, —S—$CH_3$, —S—$C_2H_5$, —S—$C_3H_7$, —S—C($CH_3$)$_3$, methyl, ethyl, n-propyl, isopropyl, n-butyl, sec-butyl, tert-butyl, —$NH_2$, —NH—$CH_3$, —NH—$C_2H_5$, —N—$(CH_3)_2$, —N($C_2H_5$)$_2$, —N($CH_3$)($C_2H_5$), —NH-phenyl, —N($CH_3$)-phenyl, —N($C_2H_5$)-phenyl, —N(phenyl)$_2$, phenoxy, benzyloxy, phenyl, benzyl, and morpholynyl.

34. A compound according to claim 33, wherein
R$^8$ represents:
  a group selected from the group consisting of methyl, ethyl, n-propyl, isopropyl, and —(CH$_2$)—(CH$_2$)—N (CH$_3$)$_2$; or a pyrrolidynyl group which is bonded via a —(CH$_2$)—(C=O) group; or
  a group selected from the group consisting of phenyl, 1-naphthyl, 2-naphthyl, 2-thiophenyl, 3-thiophenyl, 1-pyridynyl, 2-pyridynyl, 3-pyridynyl, benzo[b]furanyl, (1,3)benzodioxolyl, and (1,4)benzodioxanyl; each said group optionally being bonded via a —(C=O) group, —(CH$_2$) group, —(CH$_2$)$_2$ group, —CH(CH$_3$) group, —(CH=CH) group, —(CH$_2$)—(C=O) group, —(CH$_2$)—(CH=CH) group, or —(CH$_2$)$_3$ group, and each said group optionally being substituted by 1, 2, or 3 substituents independently selected from the group consisting of F, Cl, Br, —CN, —CF$_3$, —CHF$_2$, —CH$_2$F, —O—CH$_3$, and —O—C$_2$H$_5$;
R$^9$ represents a methyl group or ethyl group, and
R$^{10}$ represents a benzyhydryl group, or a pyrrolidynyl group which is bonded via a —(CH$_2$) group.

35. A compound according to claim 1, wherein:
R$^1$ represents a group —NR$^3$R$^4$ or a group —NR$^5$R$^6$;
R$^2$ represents:
  an alkyl group selected from the group consisting of n-propyl, isopropyl, n-butyl, sec-butyl, isobutyl, tert-butyl, n-pentyl, sec-pentyl, and (1,1)-dimethylpropyl; or an alkenyl group selected from the group consisting of 1-pentenyl, 2-pentenyl and pent-1,3-dienyl; or a cycloaliphatic group selected from the group consisting of cyclopentyl, cyclohexyl, and cycloheptyl, and bonded via a —(CH$_2$) group; or
  a group selected from the group consisting of phenyl, 1-naphthyl, 2-naphthyl, 2-furanyl, 3-furanyl, 2-thiophenyl, and 3-thiophenyl; said group optionally being bonded via a —(CH$_2$) group, —(CH$_2$)$_2$ group, —(CH$_2$)—O group, —CH(CH$_3$) group, —(CH=CH) group, or —(CH$_2$)$_3$ group, and said group optionally being substituted by 1, 2, or 3 substituents independently selected from the group consisting of F, Cl, Br, —O—CH$_3$, —O—C$_2$H$_5$, methyl, ethyl, n-propyl, and isopropyl;
R$^3$ represents a hydrogen atom or a methyl group;
R$^4$ represents:
  a group selected from the group consisting of methyl, ethyl, n-propyl, —(CH$_2$)—N(CH$_3$)$_2$, —(CH$_2$)—(CH$_2$)—N(CH$_3$)$_2$, —(CH$_2$)—(CH$_2$)—(CH$_2$)—N(CH$_3$)$_2$, —(CH$_2$)—(CH$_2$)—N(C$_2$H$_5$)$_2$, —(CH$_2$)—(CH$_2$)—(CH$_2$)—N(C$_2$H$_5$)$_2$, —(CH$_2$)—(CH$_2$)—N(CH$_3$)-(phenyl), and —(CH$_2$)—(CH$_2$)—(CH$_2$)—N(CH$_3$)-(phenyl); or
  a group selected from the group consisting of

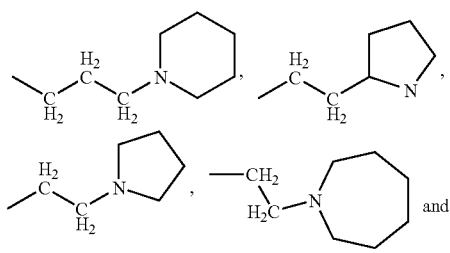

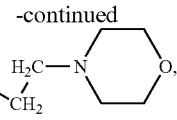

optionally substituted by a methyl group; or
a group corresponding to the formula

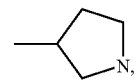

optionally substituted on the nitrogen atom by a substituent selected from the group consisting of —(CH$_2$)benzo[b]furanyl and benzyl; wherein the cyclic moiety of the groups —(CH$_2$)benzo[b]furanyl and benzyl optionally can be substituted by 1, 2, or 3 substituents independently selected from the group consisting of F, Cl, Br, —O—CH$_3$, —O—C$_2$H$_5$, —O—C$_3$H$_7$, —S—CH$_3$, —S—C$_2$H$_5$, —S—C$_3$H$_7$, —S—C(CH$_3$)$_3$, methyl, ethyl, n-propyl, isopropyl, n-butyl, phenoxy, and benzyloxy; or
  a group selected from the group consisting of phenyl and benzyl; wherein the cyclic moiety of the groups phenyl and benzyl optionally can be substituted by 1, 2, or 3 substituents independently selected from the group consisting of —O—CH$_3$, —O—C$_2$H$_5$, —O—C$_3$H$_7$, —N—(CH$_3$)$_2$, —N(C$_2$H$_5$)$_2$, and morpholynyl;
R$^5$ and R$^6$ together with the nitrogen atom to which they are attached form a group selected from the group consisting of:

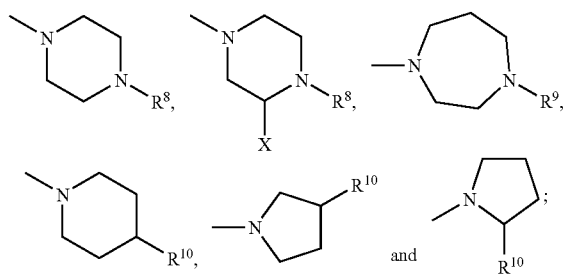

wherein:
X represents a methyl group;
R$^8$ represents:
  a group selected from the group consisting of methyl, ethyl, n-propyl, isopropyl, and —(CH$_2$)—(CH$_2$)—N(CH$_3$)$_2$; or a pyrrolidynyl group bonded via a —(CH$_2$)—(C=O) group; or
  a group selected from the group consisting of phenyl, 1-naphthyl, 2-naphthyl, 2-thiophenyl, 3-thiophenyl, 1-pyridynyl, 2-pyridynyl, 3-pyridynyl, benzo[b]furanyl, (1,3)benzodioxolyl, and (1,4)benzodioxanyl; said group optionally being bonded via a —(C=O) group, —(CH$_2$) group, —(CH$_2$)$_2$ group, —CH(CH$_3$) group, —(CH=CH) group, —(CH$_2$)—(C=O) group, —(CH$_2$)—(CH=CH) group, or —(CH$_2$)$_3$ group, and said group optionally being substituted by 1, 2, or 3 substituents independently selected from the group consisting of F, Cl, Br, —CN, —CF$_3$, —CHF$_2$, —CH$_2$F, —O—CH$_3$, and —O—C$_2$H$_5$;

R$^9$ represents a methyl group or ethyl group; and

R$^{10}$ represents a benzyhydryl group, or a pyrrolidynyl group bonded via a —(CH$_2$) group.

36. A compound according to claim 1, selected from the group consisting of:

2-cyclohexyl-N-{4-[4-(2-dimethylaminoethyl)piperazin-1-carbonyl]-4,5,6,7-tetrahydrobenzthiazol-2-yl)-acetamide, N-[4-(4-methyl[1, 4]diazepam-1-carbonyl)-4,5,6,7-tetrahydrobenzthiazol-2-yl]-2-phenoxyacetamide, 2-(2-phenylpropionylamino)-4,5,6,7-tetrahydrobenzthiazol-4-carboxylic acid (3-dimethylaminopropyl)amide, naphthalene-2-carboxylic acid[4-(4-methylpiperazin-1-carbonyl)-4,5,6,7-tetrahydrobenzthiazol-2-yl]amide, N-[4-(2-pyrrolidin-1-yl-methylpyrrolidin-1-carbonyl)-4,5,6,7-tetrahydrobenzthiazol-2-yl]-2-thiophen-2-yl-acetamide, N-{4-[4-(7-methoxybenzo[1, 3]dioxol-5-ylmethyl)piperazin-1-carbonyl]-4,5,6,7-tetrahydrobenzthiazol-2-yl}-2-(2-methoxyphenyl)acetamide, N-{4-[4-(4-methoxyphenyl)-3-methylpiperazin-1-carbonyl]-4,5,6,7-tetrahydrobenzthiazol-2-yl}benzamide, furan-2-carboxylic acid{4-[4-(4-acetylphenyl)piperazin-1-carbonyl]-4,5,6,7-tetrahydrobenzthiazol-2-yl}amide, 2-[(furan-2-carbonyl)amino]-4,5,6,7-tetrahydrobenzthiazol-4-carboxylic acid[1-(2,4,6-trimethoxybenzyl)pyrrolidin-3-yl]amide, N-[4-(4-isopropylpiperazin-1-carbonyl)-4,5,6,7-tetrahydrobenzthiazol-2-yl]-2-phenylpropionamide, 3-furan-2-yl-N-[4-(4-thiophen-3-ylmethylpiperazin-1-carbonyl)-4,5,6,7-tetrahydrobenzthiazol-2-yl]acrylamide, 2-(4-methoxybenzoylamino)-4,5,6,7-tetrahydrobenzthiazol-4-carboxylic acid[1-(2-chloro-6-fluorobenzyl)pyrrolidin-3-yl]methylamide, hexanoic acid[4-(4-pyridin-4-ylpiperazin-1-carbonyl)-4,5,6,7-tetrahydrobenzthiazol-2-yl]amide, 2-(2-thiophen-2-ylacetylamino)-4,5,6,7-tetrahydrobenzthiazol-4-carboxylic acid (3-morpholin-4-ylpropyl)amide, 2-(2-phenylpropionylamino)-4,5,6,7-tetrahydrobenzthiazol-4-carboxylic acid[1-(4-phenoxybenzyl)pyrrolidin-3-yl]amide, 2-[(furan-3-carbonyl)amino]-4,5,6,7-tetrahydrobenzthiazol-4-carboxylic acid (2-azepan-1-ylethyl)amide, furan-3-carboxylic acid[4-(4-benzofuran-2-ylmethylpiperazin-1-carbonyl)-4,5,6,7-tetrahydrobenzthiazol-2-yl]amide, 2-hexanylamino-4,5,6,7-tetrahydrobenzthiazol-4-carboxylic acid[3-(2-methylpiperidin-1-yl)propyl]amide, 2-(2-phenylpropionylamino)-4,5,6,7-tetrahydrobenzthiazol-4-carboxylic acid (2-dimethylamino-ethyl)amide, 2-ethoxy-N-[4-(4-phenethylpiperazin-1-carbonyl)-4,5,6,7-tetrahydrobenzthiazol-2-yl]benzamide, 2-(4-fluorophenoxy)-N-[4-(4-phenylpiperazin-1-carbonyl)-4,5,6,7-tetrahydrobenzthiazol-2-yl]acetamide, 2-(2-phenylpropionylamino)-4,5,6,7-tetrahydrobenzthiazol-4-carboxylic acid[2-(1-methylpyrrolidin-2-yl)ethyl]amide, 2-(3-furan-2-ylacryloylamino)-4,5,6,7-tetrahydrobenzthiazol-4-carboxylic acid [3-(2-methylpiperidin-1-yl)propyl]amide, 2-(3,3-dimethylbutyrylamino)-4,5,6,7-tetrahydrobenzthiazol-4-carboxylic acid (3-dimethylaminopropyl)amide, N-{4-[4-(4-chlorobenzyl)piperazin-1-carbonyl]-4,5,6,7-tetrahydrobenzthiazol-2-yl}-4-methoxybenzamide, naphthalene-2-carboxylic acid[4-(2-pyrrolidin-1-ylmethylpyrrolidin-1-carbonyl)-4,5,6,7-tetrahydrobenzthiazol-2-yl]amide, N-[4-(4-benzofuran-2-ylmethylpiperazin-1-carbonyl)-4,5,6,7-tetrahydrobenzthiazol-2-yl]butyramide, N-{4-[4-(3-methoxyphenyl)piperazin-1-carbonyl]-4,5,6,7-tetrahydrobenzthiazol-2-yl}benzamide, 2-butyrylamino-4,5,6,7-tetrahydrobenzthiazol-4-carboxylic acid (1-biphenyl-4-ylmethylpyrrolidin-3-yl)methylamide, 2-(2-phenoxyacetylamino)-4,5,6,7-tetrahydrobenzthiazol-4-carboxylic acid (2-dimethylamino-ethyl)amide, 2-ethoxy-N-[4-(2-pyrrolidin-1-ylmethylpyrrolidin-1-carbonyl)-4,5,6,7-tetrahydrobenzthiazol-2-yl]benzamide, naphthalene-2-carboxylic acid{4-[4-(2-oxo-2-pyrrolidin-1-ylethyl)piperazin-1-carbonyl]-4,5,6,7-tetrahydrobenzthiazol-2-yl}amide, 2-(2-phenylpropionylamino)-4,5,6,7-tetrahydrobenzthiazol-4-carboxylic acid[1-(2-brom-4,5-dimethoxybenzyl)pyrrolidin-3-yl]amide, hexanoic acid{4-[4-(2,4,6-trimethoxybenzyl)piperazin-1-carbonyl]-4,5,6,7-tetrahydrobenzthiazol-2-yl}amide, 2-(3,5-dimethylbenzoylamino)-4,5,6,7-tetrahydrobenzthiazol-4-carboxylic acid [1-(2-tert-butylsulfanylbenzyl)pyrrolidin-3-yl]amide, 2-(2-phenylpropionylamino)-4,5,6,7-tetrahydrobenzthiazol-4-carboxylic acid[1-(2-benzyloxybenzyl)pyrrolidin-3-yl]methylamide, 2-hexa-2,4-dienoylamino-4,5,6,7-tetrahydrobenzthiazol-4-carboxylic acid (1-biphenyl-4-ylmethylpyrrolidin-3-yl)methylamide, 2-(3-phenylpropionylamino)-4,5,6,7-tetrahydrobenzthiazol-4-carboxylic acid (2-diethylamino-ethyl)amide, 2-(2-thiophen-2-ylacetylamino)-4,5,6,7-tetrahydrobenzthiazol-4-carboxylic acid (2-azepan-1-ylethyl)amide, 2-(2-thiophen-2-ylacetylamino)-4,5,6,7-tetrahydrobenzthiazol-4-carboxylic acid [1-(2-ethoxybenzyl)pyrrolidin-3-yl]methylamide, 2-hexanylamino-4,5,6,7-tetrahydrobenzthiazol-4-carboxylic acid (1-benzofuran-2-ylmethylpyrrolidin-3-yl)methylamide, 2-(2-phenoxyacetylamino)-4,5,6,7-tetrahydrobenzthiazol-4-carboxylic acid[3-(2-methylpiperidin-1-yl)propyl]amide, 2-[(naphthalene-2-carbonyl)amino]-4,5,6,7-tetrahydrobenzthiazol-4-carboxylic acid (2-pyrrolidin-1-ylethyl)amide, 2-[2-(3,5-difluorophenyl)acetylamino]-4,5,6,7-tetrahydrobenzthiazol-4-carboxylic acid[1-(2-ethoxybenzyl)pyrrolidin-3-yl]methylamide, 2-[(naphthalene-2-carbonyl)amino]-4,5,6,7-tetrahydrobenzthiazol-4-carboxylic acid 4-dimethylaminobenzylamide, 2-[2-(4-fluorophenoxy)acetylamino]-4,5,6,7-tetrahydrobenzthiazol-4-carboxylic acid[2-(1-methylpyrrolidin-3-yl)ethyl]amide, furan-2-carboxylic acid{4-[4-(2-cyano-phenyl)piperazin-1-carbonyl]-4,5,6,7-tetrahydrobenzthiazol-2-yl}amide, 2-(3-phenylpropionylamino)-4,5,6,7-tetrahydrobenzthiazol-4-carboxylic acid (1-benzofuran-2-ylmethylpyrrolidin-3-yl)methylamide, 2-hexa-2,4-dienoylamino-4,5,6,7-tetrahydrobenzthiazol-4-carboxylic acid[1-(2,6-dichlorobenzyl)pyrrolidin-3-yl]methylamide,
2-[(furan-2-carbonyl)amino]-4,5,6,7-tetrahydrobenzthiazol-4-carboxylic acid[1-(5-bromo-2-ethoxybenzyl)pyrrolidin-3-yl]amide,
2-(2-phenoxyacetylamino)-4,5,6,7-tetrahydrobenzthiazol-4-carboxylic acid[1-(2-ethoxybenzyl)pyrrolidin-3-yl]methylamide,
hexanoic acid{4-[4-(2-fluorophenyl)piperazin-1-carbonyl]-4,5,6,7-tetrahydrobenzthiazol-2-yl}amide,
naphthalene-2-carboxylic acid{4-[4-(2-fluorobenzyl)piperazin-1-carbonyl]-4,5,6,7-tetrahydrobenzthiazol-2-yl}amide,
2-(2-phenoxyacetylamino)-4,5,6,7-tetrahydrobenzthiazol-4-carboxylic acid methyl-[1-(2-trifluoromethylbenzyl)pyrrolidin-3-yl]amide,
2-(3-phenylpropionylamino)-4,5,6,7-tetrahydrobenzthiazol-4-carboxylic acid (1-biphenyl-4-ylmethylpyrrolidin-3-yl)methylamide,
2-[2-(2-methoxyphenyl)acetylamino]-4,5,6,7-tetrahydrobenzthiazol-4-carboxylic acid (1-benzofuran-2-ylmethylpyrrolidin-3-yl)methylamide,
2-(3,5-difluorophenyl)-N-[4-(2-pyrrolidin-1-ylmethylpyrrolidin-1-carbonyl)-4,5,6,7-tetrahydrobenzthiazol-2-yl]acetamide,
2-[(furan-2-carbonyl)amino]-4,5,6,7-tetrahydrobenzthiazol-4-carboxylic acid 4-dimethylamino-benzylamide,
hexanoic acid{4-[4-(3-fluoro-4-methoxybenzyl)piperazin-1-carbonyl]-4,5,6,7-tetrahydrobenzthiazol-2-yl}amide,
N-{4-[4-(4-methoxyphenyl)-3-methylpiperazin-1-carbonyl]-4,5,6,7-tetrahydrobenzthiazol-2-yl}-2-phenylpropionamide,
2-hexa-2,4-dienoylamino-4,5,6,7-tetrahydrobenzthiazol-4-carboxylic acid [1-(2-chloro-6-fluorobenzyl)pyrrolidin-3-yl]methylamide,
2-[2-(3,5-difluorophenyl)acetylamino]-4,5,6,7-tetrahydrobenzthiazol-4-carboxylic acid[1-(2,6-dichlorobenzyl)pyrrolidin-3-yl]methylamide,
2-[2-(4-fluorophenoxy)acetylamino]-4,5,6,7-tetrahydrobenzthiazol-4-carboxylic acid[1-(2-ethoxybenzyl)pyrrolidin-3-yl]methylamide,
furan-3-carboxylic acid[4-(4-pyridin-2-ylpiperazin-1-carbonyl)-4,5,6,7-tetrahydrobenzthiazol-2-yl]amide,
hexanoic acid[4-(4-benzofuran-2-ylmethylpiperazin-1-carbonyl)-4,5,6,7-tetrahydrobenzthiazol-2-yl]amide,
2-phenoxy-N-{4-[4-(1-phenylethyl)piperazin-1-carbonyl]-4,5,6,7-tetrahydrobenzthiazol-2-yl}acetamide,
2-(2-cyclohexylacetylamino)-4,5,6,7-tetrahydrobenzthiazol-4-carboxylic acid[1-(2,6-dichlorobenzyl)pyrrolidin-3-yl]methylamide,
2-(2-cyclohexylacetylamino)-4,5,6,7-tetrahydrobenzthiazol-4-carboxylic acid[3-(methylphenyl-amino)propyl]amide,
2-(2-ethoxybenzoylamino)-4,5,6,7-tetrahydrobenzthiazol-4-carboxylic acid[3-(methylphenylamino)propyl]amide,
3-phenyl-N-{4-[4-(5-trifluoromethylpyridin-2-yl)piperazin-1-carbonyl]-4,5,6,7-tetrahydrobenzthiazol-2-yl}propionamide,
furan-3-carboxylic acid[4-(4-phenethylpiperazin-1-carbonyl)-4,5,6,7-tetrahydrobenzthiazol-2-yl]amide,
3-phenyl-N-{4-[4-(3-trifluoromethylphenyl)piperazin-1-carbonyl]-4,5,6,7-tetrahydrobenzthiazol-2-yl}propionamide,
2-(3,3-dimethylbutyrylamino)-4,5,6,7-tetrahydrobenzthiazol-4-carboxylic acid [1-(2-benzyloxybenzyl)pyrrolidin-3-yl]amide,
2-(3,5-difluorophenyl)-N-{4-[4-(3-trifluoromethylphenyl)piperazin-1-carbonyl]-4,5,6,7-tetrahydrobenzthiazol-2-yl}acetamide,
2-ethoxy-N-{4-[4-(1-phenylethyl)piperazin-1-carbonyl]-4,5,6,7-tetrahydrobenzthiazol-2-yl}benzamide,
3-furan-2-yl-N-{4-[4-(3-trifluoromethylphenyl)piperazin-1-carbonyl]-4,5,6,7-tetrahydrobenzthiazol-2-yl}acrylamide,
N-{4-[4-(2-cyano-phenyl)piperazin-1-carbonyl]-4,5,6,7-tetrahydrobenzthiazol-2-yl}-3-phenylpropionamide,
2-(2-cyclohexylacetylamino)-4,5,6,7-tetrahydrobenzthiazol-4-carboxylic acid[1-(2-chloro-6-fluorobenzyl)pyrrolidin-3-yl]methylamide,
N-(4-[4-(2-methoxynaphthalene-1-ylmethyl)piperazin-1-carbonyl]-4,5,6,7-tetrahydrobenzthiazol-2-yl}-3,3-dimethylbutyramid,
2-(3,3-dimethylbutyrylamino)-4,5,6,7-tetrahydrobenzthiazol-4-carboxylic acid (2,5-diethoxy-4-morpholin-4-ylphenyl)amide,
N-{4-[4-(2-chlorophenyl)piperazin-1-carbonyl]-4,5,6,7-tetrahydrobenzthiazol-2-yl}-2-(4-fluorophenyl)acetamide,
N-[4-(4-benzylpiperazin-1-carbonyl)-4,5,6,7-tetrahydrobenzthiazol-2-yl]-3,3-dimethylbutyramide,
N-[4-(4-benzhydrylpiperazin-1-carbonyl)-4,5,6,7-tetrahydrobenzthiazol-2-yl]-2-(3,5-difluorophenyl)acetamide,
N-[4-(4-benzhydrylpiperazin-1-carbonyl)-4,5,6,7-tetrahydrobenzthiazol-2-yl]-2-thiophen-2-ylacetamide,
N-{4-[4-(2-chlorophenyl)piperazin-1-carbonyl]-4,5,6,7-tetrahydrobenzthiazol-2-yl}-2-ethoxybenzamide,
3,3-dimethyl-N-{4-[4-(5-trifluoromethylpyridin-2-yl)piperazin-1-carbonyl]-4,5,6,7-tetrahydrobenzthiazol-2-yl]-butyramide,
3,3-dimethyl-N-{4-[4-(3-phenylallyl)piperazin-1-carbonyl]-4,5,6,7-tetrahydrobenzthiazol-2-yl}butyramide
N-[4-(4-benzhydrylpiperazin-1-carbonyl)-4,5,6,7-tetrahydrobenzthiazol-2-yl]-2-cyclohexylacetamide, and
furan-2-carboxylic acid[4-(4-phenylpiperazin-1-carbonyl)-4,5,6,7-tetrahydrobenzthiazol-2-yl]amide; or a physiologically acceptable salt or solvate thereof.

37. A process for preparing a compound according to claim 1, said process comprising reacting a compound corresponding to formula II

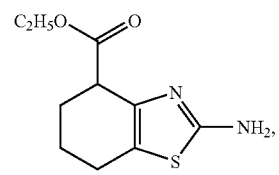

or a salt thereof with an acylation agent corresponding to formula III,

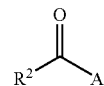

wherein

R² has the meaning given in claim 1, and

A represents a group capable of dissociation from the acyl group R²—(C=O)—, to obtain an ester corresponding to formula IV,

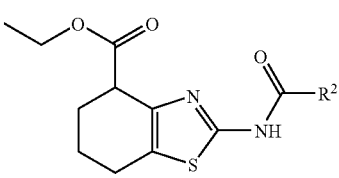
IV and optionally hydrolyzing the ester of formula IV to obtain an acid corresponding to formula V

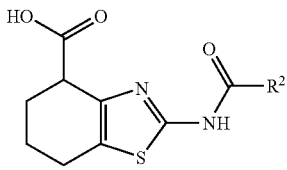
V and reacting the ester of formula IV or the acid of formula V with a compound corresponding the the formula

R¹—H wherein R¹ has the meaning given in claim 1,
to obtain a compound corresponding to formula I, and
optionally isolating or purifying the compound of formula I, and
optionally converting the compound of formula I to a physiologically acceptable salt or converting a salt of a compound of formula I to a free base of formula I.

38. A method according to claim 37, wherein A represents —OH, —Cl, or —O—(C=O)—R².

39. A pharmaceutical composition comprising a compound according to claim 1, and at least one pharmaceutically acceptable auxiliary.

* * * * *